United States Patent
Kortagere et al.

(10) Patent No.: US 11,266,612 B2
(45) Date of Patent: Mar. 8, 2022

(54) D3 DOPAMINE RECEPTOR AGONISTS TO TREAT DYSKINESIA IN PARKINSON'S DISEASE

(71) Applicants: DREXEL UNIVERSITY, Philadelphia, PA (US); RUTGERS, THE STATE UNIVERSITY OF NEW JERSEY, New Brunswick, NJ (US)

(72) Inventors: Sandhya Kortagere, Newtown, PA (US); Eldo V. Kuzhikandahil, Chester, NJ (US)

(73) Assignees: Drexel University, Philadelphia, PA (US); Rutgers, The State University of New Jersey, New Brunswick, NJ (US)

(*) Notice: Subject to any disclaimer, the term of this patent is extended or adjusted under 35 U.S.C. 154(b) by 0 days.

(21) Appl. No.: 16/752,119

(22) Filed: Jan. 24, 2020

(65) Prior Publication Data
US 2020/0390728 A1 Dec. 17, 2020

Related U.S. Application Data

(60) Continuation of application No. 15/497,287, filed on Apr. 26, 2017, now Pat. No. 10,543,180, which is a continuation-in-part of application No. 13/957,861, filed on Aug. 2, 2013, now Pat. No. 9,675,565, which is a division of application No. 13/764,623, filed as application No. PCT/US2011/047263 on Aug. 10, 2011, now Pat. No. 9,289,400.

(60) Provisional application No. 61/372,733, filed on Aug. 11, 2010.

(51) Int. Cl.
| | |
|---|---|
| A61K 31/137 | (2006.01) |
| A61K 45/06 | (2006.01) |
| A61K 31/198 | (2006.01) |
| A61K 31/4045 | (2006.01) |
| A61K 31/428 | (2006.01) |
| A61K 31/473 | (2006.01) |
| A61K 31/48 | (2006.01) |
| A61K 31/506 | (2006.01) |
| A61K 31/519 | (2006.01) |
| A61K 31/5513 | (2006.01) |
| A61K 31/4184 | (2006.01) |
| C07C 211/29 | (2006.01) |
| C07C 215/08 | (2006.01) |
| C07D 209/14 | (2006.01) |
| C07D 471/04 | (2006.01) |
| C07C 215/54 | (2006.01) |
| C07C 217/62 | (2006.01) |
| C07D 235/16 | (2006.01) |

(52) U.S. Cl.
CPC .......... *A61K 31/137* (2013.01); *A61K 31/198* (2013.01); *A61K 31/4045* (2013.01); *A61K 31/4184* (2013.01); *A61K 31/428* (2013.01); *A61K 31/473* (2013.01); *A61K 31/48* (2013.01); *A61K 31/506* (2013.01); *A61K 31/519* (2013.01); *A61K 31/5513* (2013.01); *A61K 45/06* (2013.01); *C07C 211/29* (2013.01); *C07C 215/08* (2013.01); *C07C 215/54* (2013.01); *C07C 217/62* (2013.01); *C07D 209/14* (2013.01); *C07D 235/16* (2013.01); *C07D 471/04* (2013.01)

(58) Field of Classification Search
CPC ... C07C 211/29; C07C 215/08; C07C 215/54; C07C 217/62; C07D 209/14; C07D 235/16; C07D 471/04; A61K 45/06; A61K 31/4045; A61K 31/428; A61K 31/473; A61K 31/519; A61K 31/4184; A61P 43/00; A61P 25/16; A61P 25/14
See application file for complete search history.

(56) References Cited

U.S. PATENT DOCUMENTS

| | | |
|---|---|---|
| 2,407,167 A | 9/1946 | Kulz |
| 5,332,719 A | 7/1994 | Findeisen et al. |
| 5,352,688 A | 10/1994 | Kaminski |
| 6,031,003 A | 2/2000 | Nemeth et al. |
| 6,057,371 A | 5/2000 | Glennon |
| 2004/0053925 A1 | 3/2004 | Deprez et al. |
| 2008/0058356 A1 | 3/2008 | Crespo Crespo et al. |

(Continued)

FOREIGN PATENT DOCUMENTS

| | | |
|---|---|---|
| CA | 2824106 A1 | 3/2005 |
| CN | 1953975 A | 4/2007 |
| DE | 102011015842 A1 | 11/2012 |

(Continued)

OTHER PUBLICATIONS

Patent Examination Report No. 1, dated Feb. 5, 2014, Australian Government.

(Continued)

*Primary Examiner* — Sahar Javanmard
(74) *Attorney, Agent, or Firm* — Saul Ewing Arnstein & Lehr LLP; Kathryn Doyle; Domingos J. Silva

(57) ABSTRACT

The present invention provides a method of inhibiting, suppressing or preventing levodopa-induced dyskinesia in a patient suffering from Parkinson's Disease, comprising the step of administering to the patient a pharmaceutical composition comprising at least one compound of the invention. The present invention further provides a method of inhibiting, suppressing or preventing Parkinson's Disease in a patient, comprising the step of administering to the patient a pharmaceutical composition comprising at least one compound of the invention.

11 Claims, 35 Drawing Sheets

Specification includes a Sequence Listing.

(56) References Cited

U.S. PATENT DOCUMENTS

| | | |
|---|---|---|
| 2009/0281149 A1 | 11/2009 | Scott et al. |
| 2010/0143322 A1 | 6/2010 | Wolf et al. |

FOREIGN PATENT DOCUMENTS

| | | |
|---|---|---|
| EP | 0009702 A1 | 4/1980 |
| EP | 1138666 B1 | 3/2004 |
| EP | 1 977 746 B1 * | 2/2008 |
| EP | 2170805 A2 | 4/2010 |
| GB | 2059770 A | 4/1981 |
| GB | 2276161 A | 9/1994 |
| JP | S34-3365 | 5/1959 |
| JP | H05112538 A | 5/1993 |
| JP | H10504519 A | 5/1998 |
| JP | 2004535365 A | 11/2004 |
| JP | 6245983 B2 | 11/2017 |
| WO | 9323035 A2 | 11/1993 |
| WO | 9529147 A1 | 11/1995 |
| WO | 9943678 A1 | 9/1999 |
| WO | 2004071445 A2 | 8/2004 |
| WO | 2004113391 A2 | 12/2004 |
| WO | 2005020882 A2 | 3/2005 |
| WO | 2005034928 A1 | 4/2005 |
| WO | 2005058883 A1 | 6/2005 |
| WO | 2006020879 A1 | 2/2006 |
| WO | 2006078239 A1 | 7/2006 |
| WO | 2006083692 A2 | 8/2006 |
| WO | 2006085149 A2 | 8/2006 |
| WO | 2006097744 A2 | 9/2006 |
| WO | 2007002516 A2 | 1/2007 |
| WO | 2007022415 A2 | 2/2007 |
| WO | 2007133772 A2 | 11/2007 |
| WO | 2008052953 A1 | 5/2008 |
| WO | 2008107335 A1 | 9/2008 |
| WO | 2008113364 A2 | 9/2008 |
| WO | 2008130464 A1 | 10/2008 |
| WO | 2009035684 A1 | 3/2009 |
| WO | 2009136175 A1 | 11/2009 |
| WO | 2009140204 A2 | 11/2009 |
| WO | 2012021629 A2 | 2/2012 |

OTHER PUBLICATIONS

PubChemSubstance Direct Submission ID 84973441, 2-[(2-chlorobenzyl)amino]butan-1-ol Substance Summary (Retrieved from the internet Mar. 28, 2013 <http://pubchem.ncbi.nih.gov/summary.cgi?sid=84973441>, 2009.

CAS RN 1183990-06-8; Benzenepropanamine, 2-chloro-N,α-dimethyl—(CA Index Name), STN Entry Date Sep. 14, 2009.

CAS RN 855397-31-8; Phenol, 2-(3-aminobutyl)—(CA Index Name), STN Entry Date Jul. 15, 2005.

CAS RN 51062-15-8; Benzenepropanamine, 4-methoxy-α-methyl—(CA Index Name), STN Entry Date Nov. 16, 1984.

CAS RN 1099621-82-5; Benzenepropanamine, 2-bromo-α-methyl—(CA Index Name), STN Entry Date Feb. 2, 2009.

CAS RN 943109-70-4; Benzenepropanamine, 2-methoxy-α-methyl—(CA Index Name), STN Entry Date Jul. 22, 2007.

CAS RN 878684-94-7; Benzenepropanamine, 3,4-diethoxy—(CA Index Name), STN Entry Date Mar. 31, 2006.

CAS RN 1092924-49-6; Benzenepropanamine, 2-fluoro-α-methyl—(CA Index Name), STN Entry Date Jan. 7, 2009.

Aldous, et al., "Structure-activity relationships in psychotomimetic phenylalkylamines", J Med Chem. 17(10), Oct. 1974, 1100-1111.

Ask, et al., "Selective inhibition of monoamine oxidase by p-aminosubstituted phenylalkylamines in catecholaminergic neurones", Neuropharmacology.25(1), 1986, 33-40.

Boeckler, et al., "CoMFA and CoMSIA investigations revealing novel insights into the binding modes of dopamine D3 receptor agonists", J Med Chem. 48(7), 2005, 2493-2508.

Clarke, et al., "Cabergoline versus bromocriptine for levodopa-induced complications in Parkinson's disease", Cochrane Database Syst Rev. (1), 2001, CD001519.

Costall, et al., "Dyskinetic phenomena caused by the intrastriatal injection of phenylethylamine, phenylpiperazine, tetrahydroisoquinoline and tetrahydronaphthalene derivatives in the guinea pig", Eur J Pharmacol. 31(1), 1975, 94-109.

Dukat, et al., "Structure-activity relationships for the binding of arylpiperazines and arylbiguanides at 5-HT3 serotonin receptors", J Med Chem. 39(20), Sep. 27, 1996, 4017-4026.

Fuller, et al., "Effects of some homologues of 4-chloroamphetamine on brain serotonin metabolism", Neuropharmacology. 13(7), 1974, 609-614.

Fuller, et al., "Inhibition of phenylethanolamine N-methyltransferase by benzylamines. 1. Structure-activity relationships", J Med Chem. 16(2), 1973, 101-106.

Giles, et al., "The synthesis of NPPB and NPBB by reductive amination and the effects of these compounds on K+ channels of the alga Nitella hookeri", Bioorg Med Chem Lett. 13(2), Jan. 2003, 293-295.

Goodwin, et al., "Metabolism of dopamine analogues in rat", Xenobiotica. 24(2), 1994, 129-141.

Grundt, et al., "Heterocyclic analogues of N-(4-(4-(2,3-dichlorophenyl)piperazin-1-yl)butyl)arylcarboxamides with functionalized linking chains as novel dopamine D3 receptor ligands: potential substance abuse therapeutic agents", J Med Chem. 50(17), 2007, 4135-4146.

Hajipour, et al., "Synthesis and characterization of N,N-dialkyl and N-alkyl-N-aralkyl fenpropimorph-derived compounds as high affinity ligands for sigma receptors", Bioorg Med Chem. 18(12), 2010, 4397-4404.

Klein, et al., "Synthesis of chiral 1,4-disubstituted-1,2,3-triazole derivatives from amino acids", Molecules. 14(12), Dec. 9, 2009, 5124-5143.

Lin, "Zwitterionic rhodium complex catalyzed hdroaminomethylation of arylethylenes", Tetrahedron Letters 42, 2001, 2423-2425.

Mahmoudian, "QSAR of inhibition of monoamine oxidase by substituted phenylalkylamines in vitro and in various neurons in vivo", Acta Pharm Suec. 25(3), 1988, 151-162.

Martin, et al., "Structural relationships in the inhibition of [3H]tryptamine binding to rat brain membranes in vitro by phenylalkylamines", Eur J Pharmacol. 132(1), 1986, 53-55.

Newman, et al., "N-(4-(4-(2,3-dichloro- or 2-methoxyphenyl)piperazin-1-yl)butyl)heterobiarylcarboxamides with functionalized linking chains as high affinity and enantioselective D3 receptor antagonists", J Med Chem. 52(8), 2009, 2559-2570.

Palacios, et al., "Preparation of fluoroalkyl imines, amines, enamines, ketones, alpha-amino carbonyls, and alpha-amino acids from primary enamine phosphonates.", J Org Chem. 69(25), Dec. 2004, 8767-8774.

Pindell, et al., "Autonomic effects of a series of phenylalkylamine derivatives", J Med Pharm Chem. 3, Jan. 1961, 167-182.

Rybczyńska, et al., "Pharmacological activity of calcimimetic NPS R-568 administered intravenously in rats: dose dependency", Pharmacol Rep. 58(4), Jul.-Aug. 2006, 533-539.

Schapira, "Present and future drug treatment for Parkinson's disease", J Neurol Neurosurg Psychiatry. 76(11), Nov. 2005, 1472-1478.

Wang, et al., "Suppression of Levodopa-Induced Dyskinesia in Parkinson's Disease", Chinese Journal of Clinical Neurosciences 9(2), 2001, 215-216 (Abstract Only).

Westrich, et al., "Development of tolerance in D3 dopamine receptor signaling is accompanied by distinct changes in receptor conformation", Biochem Pharmacol. 79(6), 2010, 897-907.

Yraola, et al., "New efficient substrates for semicarbazide-sensitive amine oxidase/VAP-1 enzyme: analysis by SARs and computational docking", J Med Chem. 49(21), Oct. 19, 2006, 6197-6208.

* cited by examiner

Fig. 4

```
DRD3   ----MASLSQLSSHLNYTCGAENSTG----ASQARPHAYYA---LSYCALILAIVFGNGL
2RH1   DYKDDDAMGQPGNGSAFLLAPNRSHAPDHDVTQQRDEVWVVGMGIVMSLIVLAIVFGNVL
           ::_*  __     :    __:_*  _    _:* *  __:  _    :   _ ::******  *

DRD3   VCMAVLKERALQTTTNYLVVSLAVADLLVATLVMPWVVYLEVTGGVWNFSRICCDVFVTL
2RH1   VITAIAKFERLQTVTNYFITSLACADLVMGLAVVPFGAAHILMK-MWTFGNFWCEFWTSI
        *  *: * _ ***_***::_*** ***::_  *:*: _   :  :*_*_: *:_:_::

DRD3   DVMMCTASILNLCAISIDRYTAVVMPVHYQHGTGQSSCRRVALMITAVWVLAFAVSCPLL
2RH1   DVLCVTASIETLCVIAVDRYFAITSPFKYQSLLTKNKARVIILMVWIVSGLTSFLPIQMH
       **:  ****_**_*::*** *:_ *_:**    :___* : **: * *:  :_   :

DRD3   FG-------FNTTGDPTVCS-ISNPDFVIYSSVVSFYLPFGVTVLVYARIYVVLK-----
2RH1   WYRATHQEAINCYAEETCCDFFTNQAYAIASSIVSFYVPLVIMVFVYSRVFQEAKRQLNI
       :          :*  .:  * *_ ::*   :_* **:****:*: : *:**:*::   *

DRD3   ------------------------------------------QRRRKRILTRQNS
2RH1   FEMLRIDEGLRLKIYKDTEGYYTIGIGHLLTKSPSLNAAKSELDKAIGRNTNGVITKDEA
                                                 *_ : ::*::::

DRD3   Q-------CNSVRPGFPQQTLSPDPAHLELKR----YYSICQDTALGGPGFQERGGELKR
2RH1   EKLFNQDVDAAVRGILRNAKLKPVYDSLDAVRRAALINMVFQMGETGVAGFTNSLRMLQ-
       :       :**   :  :  _*_*    *: *      : *    *  _**  :    *:

DRD3   EEKTRNSLSPTIAPKLSLEVRKLSNGRLSTSLKLGPLQPRGVPLREKKATQMVAIVLGAF
2RH1   -QKRWDEAAVNLAKSRWYNQTPNRAKRVITTFRTGTWDAYKFCLKEHKALKTLGIIMGTF
        :*   :_  :  _:*  _     :    *: *:::  *_  :_  _ *:*:**  :  :_*::*:*

DRD3   IVCWLPFFLTHVLNTHCQTCHVSPELYSATTWLGYUNSALNPVIYTTFNIEFRKAFLKIL
2RH1   TLCWLPFFIVNIVH-VIQDNLIRKEVYILLNWIGYVNSGFNPLIYCRS-PDFRIAFQELL
        :******:_::::   *   : *:*  _*:***** _:**:**    :** ** ::*

DRD3   SC--------------------
2RH1   CLRRSSLKAYGNGYSSNGNTGEQSG
                                -
```

|         | hSERT | hNET    | hDAT   |
|---------|-------|---------|--------|
| LogIC50 | 1.555 | -0.5326 | 0.9306 |
| IC50    | 35.85 | 0.2933  | 8.523  |

D3 DOPAMINE RECEPTOR AGONISTS TO TREAT DYSKINESIA IN PARKINSON'S DISEASE

CROSS-REFERENCE TO RELATED APPLICATIONS

The present application is a continuation of and claims priority to U.S. patent application Ser. No. 15/497,287, filed Apr. 26, 2017, now issued as U.S. Pat. No. 10,543,180, which is a continuation of and claims priority to U.S. patent application Ser. No. 13/957,861, filed Aug. 2, 2013, now issued as U.S. Pat. No. 9,675,565, which is a divisional of and claims priority to U.S. patent application Ser. No. 13/764,623, filed Feb. 11, 2013, now issued as U.S. Pat. No. 9,289,400, which is a 35 U.S.C. § 371 national phase application from, and claims priority to International Application No. PCT/US2011/047263, filed Aug. 10, 2011, and published under PCT Article 21(2) in English, which claims priority under 35 U.S.C. § 119(e) to U.S. Provisional Application No. 61/372,733, filed Aug. 11, 2010, all of which applications are hereby incorporated by reference in their entireties herein.

SEQUENCE LISTING

The instant application contains a Sequence Listing which has been submitted in ASCII format via EFS-Web and is hereby incorporated by reference in its entirety. Said ASCII copy, created on Apr. 25, 2017, is named 046528-6035US4_SequenceListing_ST25.txt and is 8.13 kilobytes in size.

BACKGROUND OF THE INVENTION

The family of G-protein coupled receptors (GPCRs) is one of the most important classes of proteins from both functional and structural standpoints. The human genome contains nearly 950 genes coding for GPCRs, of which nearly 450 genes have been implicated as therapeutic targets. Ligand binding to GPCRs induces multiple receptor conformations and different ligands may stabilize different receptor conformations (Kenakin & Miller, 2010, Pharmacol. Rev. 62(2):265-304). The concept of functional selectivity is based on the hypothesis that different receptor conformations recruit different signaling proteins which leads to preferential activation of one signaling pathway over another (Mailman, 2007, Trends Pharmacol. Sci. 28(8): 390-396). In addition to selecting the signaling pathways, agonist-induced receptor conformations can also potentially affect receptor signaling properties.

Among the GPCRs, the subfamily of dopamine receptors has attracted attention from biologists and pharmacologists. In the central nervous system, dopamine receptors are widely expressed and involved in the control of locomotion, cognition, emotion and neuroendocrine secretion. In the peripheral system, dopamine receptors are present more prominently in kidney, vasculature and pituitary, where they affect mainly sodium homeostasis, vascular tone, and hormone secretion. While there are numerous examples of functionally-selective ligands, which preferentially activates one signaling cascade but not others, functionally-selective ligands that alter receptor signaling properties are rare and have not been described for dopamine receptors.

The neurotransmitter dopamine controls a wide variety of physiological and behavioral functions in mammals via five major subtypes of dopamine receptors. They are broadly classified into the "$D_1$ like" and "$D_2$ like" dopamine receptors based on pharmacology and function. The $D_1$-like consists of $D_1$ and $D_5$ receptors, while the $D_2$-like consists of $D_2$, $D_3$, and $D_4$ receptors. The $D_3$ receptor primarily couples to the pertussis toxin-sensitive G$\alpha$-proteins (Gi/Go) (Ahlgren-Beckendorf & Levant, 2004, J. Recept. Signal Transduct. Res. 24(3):117-130). When transfected into different cell lines, the $D_3$ receptor couples to adenylyl cyclase V isoform (Robinson & Caron, 1997, Mol. Pharmacol. 52:508-514) and initiates signaling events including phosphorylation of mitogen-activated protein (MAP) kinases (Cussac et al., 1999, Mol. Pharmacol. 56(5):1025-103). $D_2$ and $D_3$ dopamine receptors also modulate potassium and calcium channel function (Seabrook et al., 1994, Br. J. Pharmacol. 111:391-393; Werner et al., 1996, Mol. Pharmacol. 49:656-661). Transfected $D_3$ receptors couple robustly to natively expressed G-protein coupled inward rectifier potassium (GIRK) and voltage-gated P/Q type calcium channels, and inhibit firing of spontaneous action potentials and secretory activity in the AtT-20 neuroendocrine cell line (Kuzhikandathil & Oxford, 1999, J. Neurosci. 19(5):1698-1707; Kuzhikandathil & Oxford, 2000, J. Gen. Physiol. 115:697-706; Kuzhikandathil et al., 1998, Mol. Cell Neurosci. 12:390-402). The $D_3$ receptor further couples to natively expressed adenylyl cyclase V (Kuzhikandathil & Bartoszyk, 2006, Neuropharm. 51:873-884), MAP kinases (Westrich & Kuzhikandathil, 2007, Biochim. Biophys. Acta-MCR 1773: 1747-1758) and ion channels (Kuzhikandathil & Oxford, 1999, J. Neurosci. 19(5):1698-1707; Kuzhikandathil & Oxford, 2000, J. Gen. Physiol. 115:697-706; Kuzhikandathil et al., 1998, Mol. Cell Neurosci. 12:390-402; Kuzhikandathil et al., 2004, Mol. Cell Neurosci. 26:144-155) in AtT-20 cells.

The expression of $D_3$ dopamine receptor is altered under many pathological conditions and following chronic treatment. In Parkinson's disease, levodopa-induced dyskinesias are associated with a specific up regulation of $D_{3R}$ expression in putamen and globus pallidus internal segment, regions that normally express the $D_2$ receptor (Bezard et al., 2003, Nat. Med. 9(6):762-767; Guigoni et al., 2005, Parkinsonism Related Disorders 11 Suppl 1, S25-29). In rodent models, the behavioral sensitization associated with levodopa treatment is mediated by upregulated $D_3$ receptors (Guillin et al., 2001, Nature 411(6833):86-89). In schizophrenia, $D_3$ receptor expression levels are increased two fold in the basal ganglia. Antipsychotic treatment has also been reported to change the expression of $D_3$ receptor. The density of $D_3$ receptor is increased in chronic cocaine users in striatum and substantia nigra, as well as in the nucleus accumbens. Stress and depression-induced down regulation of $D_3$ receptor expression is reversed following chronic antidepressant treatment.

Dopamine receptors are targets for the treatment of various neurological and psychiatric disorders, such as Parkinson's disease, schizophrenia, drug addiction, depression, bipolar disorder, attention deficit hyperactivity syndrome, Tourette's syndrome, Huntington's disease and migraine.

Parkinson's disease (also known as Parkinson disease) is a degenerative disorder of the central nervous system that often impairs the sufferer's motor skills, speech, and other functions (Jankovic, 2008, J. Neurol. Neurosurg. Psychiatr. 79(4):368-76). Parkinson's Disease is characterized by muscle rigidity, tremor, a slowing of physical movement (bradykinesia) and a loss of physical movement (akinesia) in extreme cases. The primary symptoms of Parkinson's Disease are the results of decreased stimulation of the motor cortex by the basal ganglia, normally caused by insufficient formation and action of dopamine, which is produced in the dopaminergic neurons of the brain (specifically the substantia nigra). Secondary symptoms may include high level cognitive dysfunction and subtle language problems. Parkinson's Disease is both chronic and progressive. At present, there is no cure for Parkinson's Disease, but medications may provide relief from the symptoms.

The most widely used form of treatment is L-dopa (levodopa). Levodopa is transformed into dopamine by L-aromatic amino acid decarboxylase (also known as dopa-decarboxylase) in the dopaminergic neurons. However, only 1-5% of levodopa enters the dopaminergic neurons. The remaining levodopa is often metabolized to dopamine elsewhere, causing a wide variety of side effects ("Symptomatic pharmacological therapy in Parkinson's disease". Parkinson's Disease. London: Royal College of Physicians, 2006, pp. 59-100). Due to feedback inhibition, levodopa administration results in a reduction of the endogenous formation of levodopa, and so eventually becomes counterproductive. Levodopa may also be co-administered with carbidopa ((2S)-3-(3,4-dihydroxyphenyl)-2-hydrazino-2-methylpropanoic acid), which prevents levodopa metabolism elsewhere in the body. The dopamine agonists bromocriptine, pergolide, pramipexole, ropinirole, piribedil, cabergoline, apomorphine, and lisuride have been found to be moderately effective.

Levodopa-induced dyskinesia (LID) is a particularly serious side effect of the long-term use of levodopa. These motor fluctuations occur in more than half of Parkinson's Disease patients after 5-10 years of levodopa treatment, with the percentage of affected patients increasing over time, and LID is thought to be potentially irreversible. Dyskinesia most commonly occurs at the time of peak levodopa plasma concentrations and is thus referred to as peak-dose dyskinesia. As patients advance, they may evidence diphasic dyskinesia, which occurs when the drug concentration rises or falls. Attempts to moderate dyskinesia by the use of other treatments, such as bromocriptine (Parlodel™), appear to be ineffective. In order to avoid dyskinesia, patients with the young-onset form of the disease are often hesitant to commence levodopa therapy until absolutely necessary for fear of suffering severe dyskinesia later on. Currently, there is no pharmacotherapeutic means of treating LID in patients suffering from Parkinson's Disease.

Interestingly, there is an alteration of dopamine receptor expression in most disorders associated with the dopaminergic system, such as Parkinson's Disease. Changes in dopamine receptor expression are also observed following chronic treatment of these neurological and psychiatric disorders. In the case of $D_3$ dopamine receptor, changes in expression have been reported in Parkinson's disease, schizophrenia, depression, and drug addiction. Following chronic drug treatment, studies have reported an upregulation of $D_3$ receptor in LID in Parkinson's disease and antipsychotic-induced tardive dyskinesia in schizophrenia.

The ability of using levodopa as a therapeutic agent in the treatment of Parkinson's Disease is severely hampered by the likelihood that levodopa-induced dyskinesia (LID) will eventually develop. There is a need in the art for novel therapeutic agents that treat, ameliorate or prevent levodopa-induced dyskinesia in patients suffering from Parkinson's Disease. The present invention fulfills this need.

BRIEF SUMMARY OF THE INVENTION

The invention includes a pharmaceutical composition comprising at least one pharmaceutically acceptable carrier and at least one compound selected from the group consisting of:

a compound of formula (I):

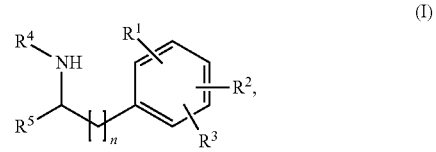

wherein in formula (I):
$R^1$, $R^2$ and $R^3$ are independently selected from the group consisting of H, cyano, hydroxyl, amino, acetamido, halo, alkoxy, nitro, $C_{1-6}$ alkyl, substituted $C_{1-6}$ alkyl, heteroalkyl, heterocyclyl, substituted heterocyclyl, aryl, substituted aryl, aryl-($C_{1-3}$)alkyl, substituted aryl-($C_{1-3}$)alkyl, carboxy, alkylcarboxy, formyl, alkyl-carbonyl, aryl-carbonyl, and heteroaryl-carbonyl;
$R^4$ and $R^5$ are independently selected from the group consisting of H, $C_{1-6}$ alkyl, substituted $C_{1-6}$ alkyl, heteroalkyl, heterocyclyl, substituted heterocyclyl, aryl, substituted aryl, aryl-($C_{1-3}$)alkyl, and substituted aryl-($C_{1-3}$)alkyl; and,
n is 2, 3, 4 or 5;

a compound of formula (IIa) or (IIb):

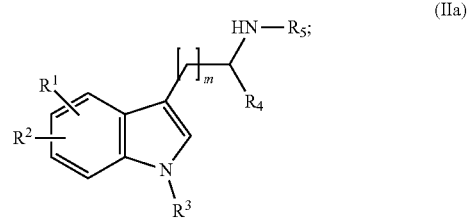

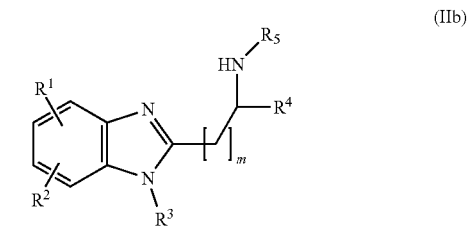

wherein in formula (IIa) or (IIb):
$R^1$ and $R^2$ are independently selected from the group consisting of H, cyano, hydroxyl, amino, acetamido, halo, alkoxy, nitro, $C_{1-6}$ alkyl, substituted $C_{1-6}$ alkyl, heteroalkyl, heterocyclyl, substituted heterocyclyl, aryl, substituted aryl, aryl-($C_{1-3}$)alkyl, substituted aryl-($C_{1-3}$)alkyl, carboxy, alkylcarboxy, formyl, alkyl-carbonyl, aryl-carbonyl, and heteroaryl-carbonyl;
$R^3$ and $R^4$ are independently selected from the group consisting of H, $C_{1-6}$ alkyl, aryl, heteroaryl, and substituted $C_{1-6}$ alkyl;
$R^5$ is selected from the group consisting of H, $C_{1-6}$ alkyl, substituted $C_{1-6}$ alkyl, heteroalkyl, heterocyclyl, substituted heterocyclyl, aryl, substituted aryl, aryl-($C_{1-3}$) alkyl, and substituted aryl-($C_{1-3}$)alkyl; and,
m is 1, 2, 3 or 4;
2,7-diamino-5-(4-fluorophenyl)-4-oxo-3,4,5,6-tetrahydro-pyrido[2,3-d]pyrimidine-6-carbonitrile; (Z)-2-(1H-benzo[d]imidazol-2-yl)-N'-hydroxy-3-(4-methoxyphenyl)propanimidamide; mixtures thereof, or a pharmaceutically acceptable salt thereof.

In one embodiment, in formula (I) $R^1$, $R^2$ and $R^3$ are independently selected from the group consisting of H, cyano, halo, alkoxy, nitro, $C_{1-6}$ alkyl, and carboxy. In another embodiment, in formula (I) $R^4$ and $R^5$ are independently selected from the group consisting of H, $C_{1-6}$ alkyl, and substituted $C_{1-6}$ alkyl. In yet another embodiment, in formula (I) n is 2. In yet another embodiment, in formula (IIa) or (IIb) m is 1 or 2.

In one embodiment, the at least one compound is selected from the group consisting of 2-amino-4-(2-chlorophenyl) butan-1-ol; 2-(3-aminohexyl)phenol; 4-(2-chlorophenyl)-2-methylamino-butane (also known as 4-(2-chlorophenyl)-N-methylbutan-2-amine); 4-(2-chlorophenyl)-butan-2-amine; 4-(2-fluorophenyl)butan-2-amine; 4-(2-bromophenyl)butan-2-amine; 4-(2-iodophenyl)butan-2-amine; 4-(2-methoxyphenyl)butan-2-amine; 2-(3-aminobutyl)phenol; 3-(3,4-diethoxyphenyl)propan-1-amine; 4-(4-chlorophenyl)butan-2-amine; 4-(4-methoxyphenyl)butan-2-amine; 2-(5-chloro-1-methyl-1H-indol-3-yl)ethanamine; 1-(5-fluoro-1-methyl-1H-indol-3-yl)propan-2-amine; 1-(5-methoxy-1-methyl-1H-indol-3-yl)propan-2-amine; 2,7-diamino-5-(4-fluorophenyl)-4-oxo-3,4,5,6-tetrahydropyrido[2,3-d]pyrimidine-6-carbonitrile; (Z)-2-(1H-benzo[d]imidazol-2-yl)-N'-hydroxy-3-(4-methoxyphenyl)propanimidamide; mixtures thereof, or a pharmaceutically acceptable salt thereof.

The invention also includes a method of treating, ameliorating or preventing levodopa-induced dyskinesia in a patient suffering from Parkinson's Disease. The method comprises administering to the patient a pharmaceutical composition comprising a therapeutically effective amount of at least one compound selected from the group consisting of: a compound of formula (I):

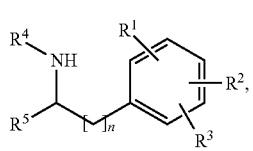

(I)

wherein in formula (I):
$R^1$, $R^2$ and $R^3$ are independently selected from the group consisting of H, cyano, hydroxyl, amino, acetamido, halo, alkoxy, nitro, $C_{1-6}$ alkyl, substituted $C_{1-6}$ alkyl, heteroalkyl, heterocyclyl, substituted heterocyclyl, aryl, substituted aryl, aryl-($C_{1-3}$)alkyl, substituted aryl-($C_{1-3}$)alkyl, carboxy, alkylcarboxy, formyl, alkyl-carbonyl, aryl-carbonyl, and heteroaryl-carbonyl;
$R^4$ and $R^5$ are independently selected from the group consisting of H, $C_{1-6}$ alkyl, substituted $C_{1-6}$ alkyl, heteroalkyl, heterocyclyl, substituted heterocyclyl, aryl, substituted aryl, aryl-($C_{1-3}$)alkyl, and substituted aryl-($C_{1-3}$)alkyl; and,
n is 2, 3, 4 or 5;
a compound of formula (IIa) or (IIb):

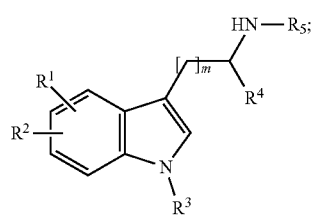

(IIa)

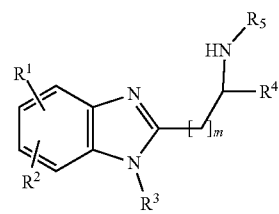

(IIb)

wherein in formula (IIa) or (IIb):
$R^1$ and $R^2$ are independently selected from the group consisting of H, cyano, hydroxyl, amino, acetamido, halo, alkoxy, nitro, $C_{1-6}$ alkyl, substituted $C_{1-6}$ alkyl, heteroalkyl, heterocyclyl, substituted heterocyclyl, aryl, substituted aryl, aryl-($C_{1-3}$)alkyl, substituted aryl-($C_{1-3}$)alkyl, carboxy, alkylcarboxy, formyl, alkyl-carbonyl, aryl-carbonyl, and heteroaryl-carbonyl;
$R^3$ and $R^4$ are independently selected from the group consisting of H, $C_{1-6}$ alkyl, aryl, heteroaryl, and substituted $C_{1-6}$ alkyl;
$R^5$ is selected from the group consisting of H, $C_{1-6}$ alkyl, substituted $C_{1-6}$ alkyl, heteroalkyl, heterocyclyl, substituted heterocyclyl, aryl, substituted aryl, aryl-($C_{1-3}$) alkyl, and substituted aryl-($C_{1-3}$)alkyl; and,
m is 1, 2, 3 or 4;
2,7-diamino-5-(4-fluorophenyl)-4-oxo-3,4,5,6-tetrahydropyrido[2,3-d]pyrimidine-6-carbonitrile; (Z)-2-(1H-benzo[d]imidazol-2-yl)-N'-hydroxy-3-(4-methoxyphenyl)propanimidamide; mixtures thereof, or a pharmaceutically acceptable salt thereof.

In one embodiment, in formula (I) $R^1$, $R^2$ and $R^3$ are independently selected from the group consisting of H, cyano, halo, alkoxy, nitro, $C_{1-6}$ alkyl, and carboxy. In another embodiment, in formula (I) $R^4$ and $R^5$ are independently selected from the group consisting of H, $C_{1-6}$ alkyl, and substituted $C_{1-6}$ alkyl. In yet another embodiment, in formula (I) n is 2. In yet another embodiment, in formula (IIa) or (IIb) m is 1 or 2.

In one embodiment, the at least one compound is selected from the group consisting of: 2-amino-4-(2-chlorophenyl) butan-1-ol; 2-(3-aminohexyl)phenol; 4-(2-chlorophenyl)-butan-2-amine; 4-(2-chlorophenyl)-2-methylamino-butane; 4-(2-fluorophenyl)butan-2-amine; 4-(2-bromophenyl)butan-2-amine; 4-(2-iodophenyl)butan-2-amine; 4-(2-methoxyphenyl)butan-2-amine; 2-(3-aminobutyl)phenol; 3-(3,4-diethoxyphenyl)propan-1-amine; 4-(4-chlorophenyl)butan-2-amine; 4-(4-methoxyphenyl)butan-2-amine; 2-(5-chloro-1-methyl-1H-indol-3-yl)ethanamine; 1-(5-fluoro-1-methyl-1H-indol-3-yl)propan-2-amine; 1-(5-methoxy-1-methyl-1H-indol-3-yl)propan-2-amine; 2,7-diamino-5-(4-fluorophenyl)-4-oxo-3,4,5,6-tetrahydropyrido[2,3-d]pyrimidine-6-carbonitrile; (Z)-2-(1H-benzo[d]imidazol-2-yl)-N'-hydroxy-3-(4-methoxyphenyl)propanimidamide; mixtures thereof, or a pharmaceutically acceptable salt thereof.

In one embodiment, the composition further comprises a drug selected from the group consisting of levodopa, clozapine, bromocriptine, pergolide, pramipexole, ropinirole, piribedil, cabergoline, apomorphine, and lisuride, a salt thereof and mixtures thereof.

In one embodiment, the pharmaceutical composition is co-administered to the patient with a second pharmaceutical composition comprising levodopa.

In one embodiment, the pharmaceutical composition is administered to the patient a given period of time before a second pharmaceutical composition comprising levodopa is administered to the patient.

In one embodiment, the given period of time varies from about 2 minutes to about 24 hours.

In one embodiment, the patient is human.

The invention further includes a method of treating, ameliorating or preventing Parkinson's Disease in a patient. The method comprises administering to the patient a pharmaceutical composition comprising a therapeutically effective amount of at least one compound selected from the group consisting of:

a compound of formula (I):

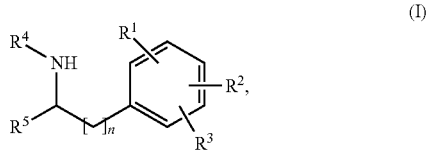

wherein in formula (I):

$R^1$, $R^2$ and $R^3$ are independently selected from the group consisting of H, cyano, hydroxyl, amino, acetamido, halo, alkoxy, nitro, $C_{1-6}$ alkyl, substituted $C_{1-6}$ alkyl, heteroalkyl, heterocyclyl, substituted heterocyclyl, aryl, substituted aryl, aryl-($C_{1-3}$)alkyl, substituted aryl-($C_{1-3}$)alkyl, carboxy, alkylcarboxy, formyl, alkyl-carbonyl, aryl-carbonyl, and heteroaryl-carbonyl;

$R^4$ and $R^5$ are independently selected from the group consisting of H, $C_{1-6}$ alkyl, substituted $C_{1-6}$ alkyl, heteroalkyl, heterocyclyl, substituted heterocyclyl, aryl, substituted aryl, aryl-($C_{1-3}$)alkyl, and substituted aryl-($C_{1-3}$)alkyl; and, n is 2, 3, 4 or 5;

a compound of formula (IIa) or (IIb):

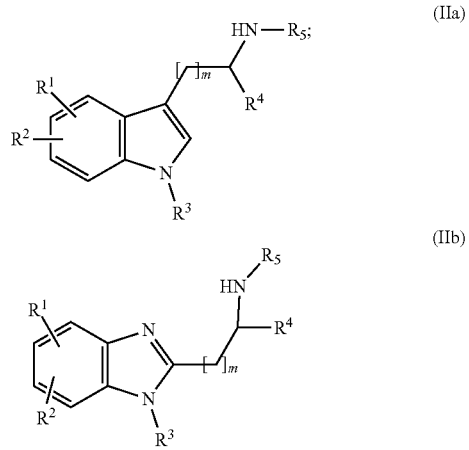

wherein in formula (IIa) or (IIb):

$R^1$ and $R^2$ are independently selected from the group consisting of H, cyano, hydroxyl, amino, acetamido, halo, alkoxy, nitro, $C_{1-6}$ alkyl, substituted $C_{1-6}$ alkyl, heteroalkyl, heterocyclyl, substituted heterocyclyl, aryl, substituted aryl, aryl-($C_{1-3}$)alkyl, substituted aryl-($C_{1-3}$)alkyl, carboxy, alkylcarboxy, formyl, alkyl-carbonyl, aryl-carbonyl, and heteroaryl-carbonyl;

$R^3$ and $R^4$ are independently selected from the group consisting of H, $C_{1-6}$ alkyl, aryl, heteroaryl, and substituted $C_{1-6}$ alkyl;

$R^5$ is selected from the group consisting of H, $C_{1-6}$ alkyl, substituted $C_{1-6}$ alkyl, heteroalkyl, heterocyclyl, substituted heterocyclyl, aryl, substituted aryl, aryl-($C_{1-3}$) alkyl, and substituted aryl-($C_{1-3}$)alkyl; and, m is 1, 2, 3 or 4;

2,7-diamino-5-(4-fluorophenyl)-4-oxo-3,4,5,6-tetrahydropyrido[2,3-d]pyrimidine-6-carbonitrile; (Z)-2-(1H-benzo[d]imidazol-2-yl)-N'-hydroxy-3-(4-methoxyphenyl)propanimidamide; mixtures thereof, or a pharmaceutically acceptable salt thereof.

In one embodiment, the at least one compound is selected from the group consisting of 2-amino-4-(2-chlorophenyl) butan-1-ol; 2-(3-aminohexyl)phenol; 4-(2-chlorophenyl)-2-methylamino-butane; 4-(2-chlorophenyl)-butan-2-amine; 4-(2-fluorophenyl)butan-2-amine; 4-(2-bromophenyl)butan-2-amine; 4-(2-iodophenyl)butan-2-amine; 4-(2-methoxyphenyl)butan-2-amine; 2-(3-aminobutyl)phenol; 3-(3,4-diethoxyphenyl)propan-1-amine; 4-(4-chlorophenyl)butan-2-amine; 4-(4-methoxyphenyl)butan-2-amine; 2-(5-chloro-1-methyl-1H-indol-3-yl)ethanamine; 1-(5-fluoro-1-methyl-1H-indol-3-yl)propan-2-amine; 1-(5-methoxy-1-methyl-1H-indol-3-yl)propan-2-amine; 2,7-diamino-5-(4-fluorophenyl)-4-oxo-3,4,5,6-tetrahydropyrido[2,3-d]pyrimidine-6-carbonitrile; (Z)-2-(1H-benzo[d]imidazol-2-yl)-N'-hydroxy-3-(4-methoxyphenyl)propanimidamide; mixtures thereof, or a pharmaceutically acceptable salt thereof.

In one embodiment, the composition further comprises at least one drug selected from the group consisting of levodopa, clozapine, bromocriptine, pergolide, pramipexole, ropinirole, piribedil, cabergoline, apomorphine, and lisuride, a salt thereof and mixtures thereof.

In one embodiment, the patient is further administered a second pharmaceutical composition comprising at least one drug selected from the group consisting of levodopa, clozapine, bromocriptine, pergolide, pramipexole, ropinirole, piribedil, cabergoline, apomorphine, and lisuride, a salt thereof and mixtures thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 4 illustrates the primary amino acid sequence alignment of $D_3$ receptor (SEQ ID NO:1) with β2AR (pdb code 2RH1—coded as BADRE-2RH1; SEQ ID NO:2). Residues that form the TM helices are shown underlined. Identical residues are indicated by "*" and similarity is indicated by ":" and ".".

FIG. 7A illustrates the structural super positioning of $D_3$ receptor bound to PD128907, PBZI and ES609, with the receptor represented in cartoon format. The transmembrane helices are numbered 1 through 7 and the extra and intracellular loops are labeled EC1-EC3 and IC1-IC3 respectively. FIG. 7B illustrates a molecular model of dopamine $D_3$ receptor with 4-(2-chlorophenyl)-butan-2-amine (ES609) docked. The receptor is depicted as ribbons, and the ligand is rendered in a space filled model.

FIG. 9A illustrates a representative voltage clamp recording of $D_3$ receptor-induced GIRK response upon two sequential 100 nM dopamine (DA) treatment. The DA was dissolved in extracellular solution with 30 mM potassium (to enhance GIRK currents). Duration of agonist application is ~60 seconds. The ratio of second to first GIRK response is a quantitative measure of tolerance. FIG. 9B is a graph bar that indicates that $D_3$ receptor tolerance is elicited by 100 nM dopamine (DA), quinpirole (QP), and PD128907; but not by PBZI or 4-(2-chlorophenyl)-butan-2-amine (ES609). FIG. 9C is a graph bar illustrating that tolerance property of $D_3$ receptor is agonist-dependent. Cumulative data showed the ratio of $2^{nd}$ to $1^{st}$ agonist-induced GIRK response in AtT-20 cells stably expressing the human D3 dopamine receptor. GIRK responses were elicited using saturating concentration of dopamine (DA, 100 nM, N=5), quinpirole (100 nM, N=5), PD128907 (100 nM, N=5), 7OH-DPAT (100 nM, N=4), 7OH-PIPAT (100 nM, N=4), sarizotan (100 nM, N=6), pramipexole (300 nM, N=4), rotigotine (100 nM, N=4), PBZI (300 nM, N=10), and FAUC 73 (300 nM, N=4). Error bars represent SEM. *, **, P<0.05, ANOVA, post-hoc Holm-Sidak test.

In FIG. 10A, 100 nM DA elicited $D_3$ receptor tolerance and SRT. In FIG. 10B, 1000 nM PBZI applied simultaneously with DA blocked the development of tolerance and SRT.

FIG. 11B) in two different functional assays. As illustrated in FIG. 11A, GIRK current response to PBZI in AtT-20 cells expressing D3 receptors was measured using whole cell voltage clamp recording. The current response was normalized for cell size (using membrane capacitance). FIG. 11B illustrates inhibition of 10 μM forskolin induced cAMP levels by activation of $D_3$ receptors in AtT-20 cells with various doses of 4-(2-chlorophenyl)-butan-2-amine. The cAMP levels were measured by using an ELISA kit from GE Healthcare. The triangle in FIG. 11B illustrates the inhibition elicited by 300 nM quinpirole.

As illustrated in FIG. 12A, PBZI induced a dose-dependent and monophasic inhibition of locomotion. The horizontal arrows indicate the hypoactivity induced by 10 mg/kg, sc PBZI (circles) plotted in 10 minute bins. The 1 mg/kg dose (triangles) had no significant effect. The locomotor activity induced by PBZI was normalized to locomotor activity in control vehicle (saline) injected mice. The data points indicated by the horizontal arrows shows statistically significant reductions in locomotor activity (p=0.002, Newman-Keuls multiple (α=0.05), n=4 mice per treatment group) that recovers to control levels by 80 minutes. As illustrated in FIG. 12B, in contrast to PBZI, Balb/c mice administered 0.4 mg/kg, sc PD128907 (circles, n=4) induces an initial hypoactivity (horizontal arrows) that is followed by hyperactivity (area indicated by hatched rectangle), which returns to levels exhibited by saline injected mice (n=4) by 120 minutes. A lower dose of PD128907 (0.05 mg/kg) elicited hypoactivity for a shorter duration (first 20 minutes) but elicited the same robust hyperactivity as the higher dose of PD128907. The PD128907-induced locomotor activity was normalized to locomotor activity in control vehicle (saline) injected mice.

As illustrated in FIG. 13B, integration of the area under the curves yields the total integrated AIMs score which is significantly reduced by the administration of PBZI (*P<0.05, ANOVA, post-hoc Holm's test).

FIG. 16A illustrates representative current clamp recording in an AtT-20 neuroendocrine cell stably expressing the human D3 dopamine receptor. Activation of the D3 receptor by 100 nM dopamine (black bar), dissolved in standard external solution with 5 mM potassium, hyperpolarized the cell and inhibited the spontaneous action potentials during the first application but not to second or third application. FIG. 16B illustrates that activation of the $D_3$ receptor by 300 nM PBZI (gray hatched bar), dissolved in standard external solution with 5 mM potassium, hyperpolarized the cell and inhibited the spontaneous action potentials during the first and second treatment.

In FIG. 17A, representative voltage clamp recording showed that 100 nM ES609 (cross hatched bar) induced GIRK currents that did not show tolerance and SRT in an AtT-20 cell stably expressing the human $D_3$ receptor. In contrast, in the same cell, 100 nM quinpirole (QP, black bar) elicited tolerance and SRT. In FIG. 17B, representative voltage clamp recording showed that neither 300 nM PBZI (hatched bar) nor 300 nM ES609 (cross hatched bar) induced GIRK currents in parental AtT-20 cells in the absence of exogenous $D_3$ receptor expression. In FIG. 17C, representative voltage clamp recording showed that 100 nM ES609 (cross hatched bar) and 100 nM quinpirole (black bar) induced GIRK currents in AtT-20 cell stably expressing the human $D_{2S}$ receptor. The ES609-induced GIRK current was significantly less than the quinpirole-induced current in D2S receptor expressing cells. The cells were held at −65 mV and the duration of agonist application was 60 seconds. FIG. 17D illustrates cumulative dose response of ES609-induced GIRK response in AtT-20 cells stably expressing the human D3 receptor. The black filled circle is the GIRK response elicited by a saturating dose of quinpirole (QP, 300 nM) and showed that ES609 is a full agonist at the $D_3$ receptor. Error bars represent ±SEM. The GIRK currents were divided by cell capacitance to normalize for cell size. The data points were fit with a four parameter Hill equation.

DETAILED DESCRIPTION OF THE INVENTION

Figure 1A:
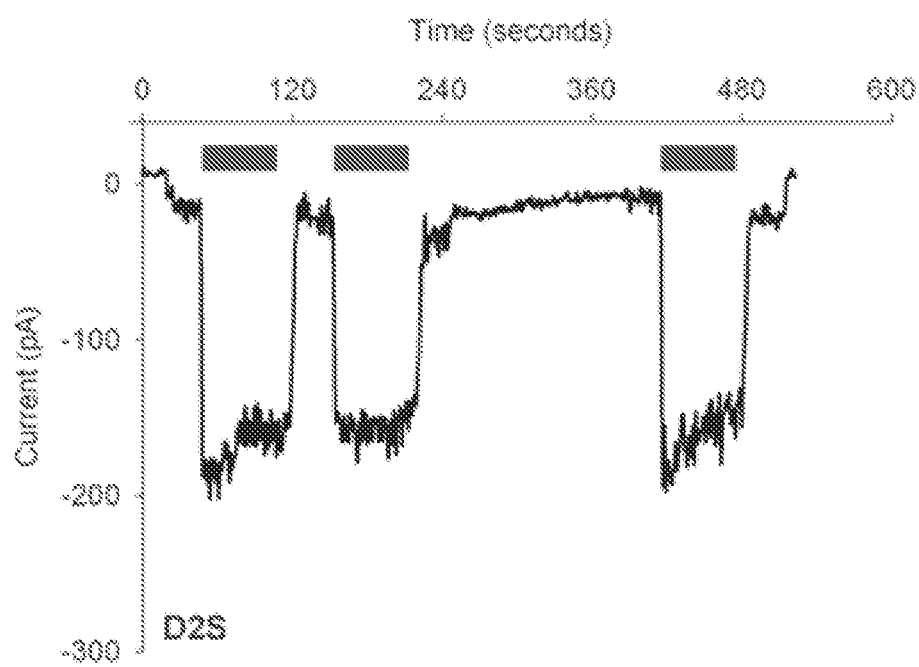
FIGS. 1A-1D illustrate representative voltage (FIGS. 1A and 1C) and current (FIGS. 1B and 1D) clamp recording in AtT-20 cells stably expressing either human $D_{2S}$ (FIGS. 1A and 1B) or $D_3$ (FIGS. 1C and 1D). For voltage clamp recording (FIGS. 1A and 1C), the cells were held at −65 mV and 100 nM dopamine (black bar) applied for 1 minute. For current clamp recording (FIGS. 1B and 1D), the spontaneous action potentials were hyperpolarized by one minute application of 100 nM quinpirole (QP), which is an agonist for $D_2$-like receptors.
Figure 1B:
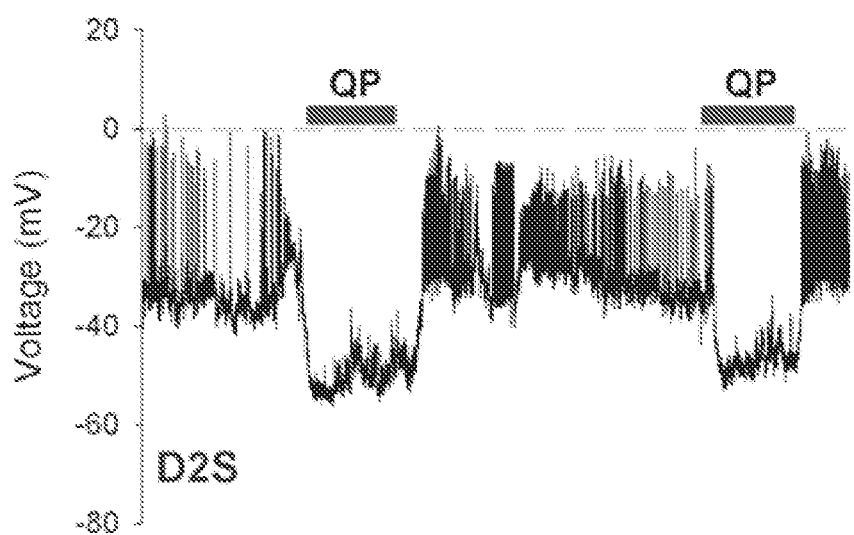
Figure 1C:
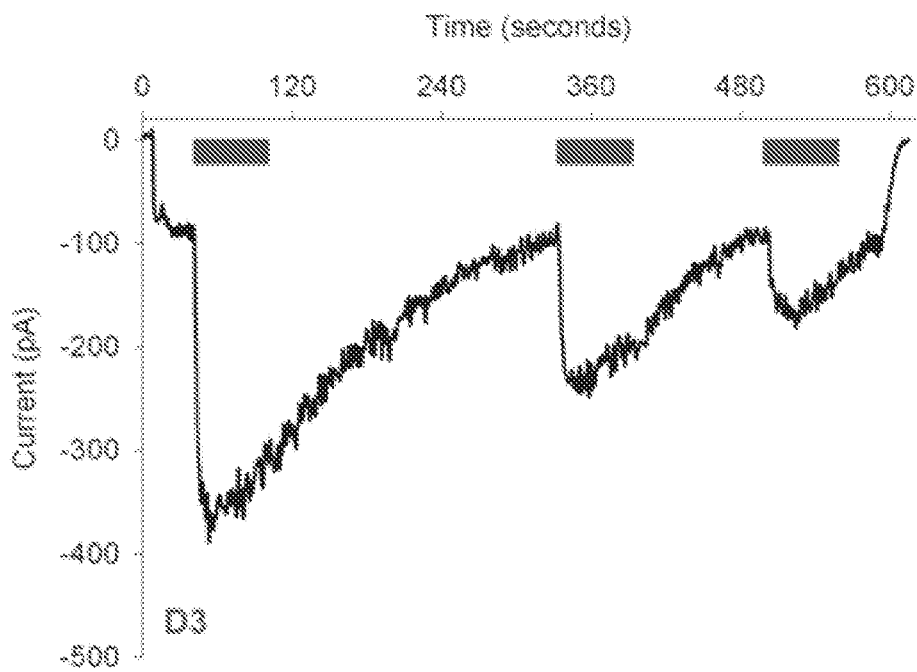
Figure 1D:
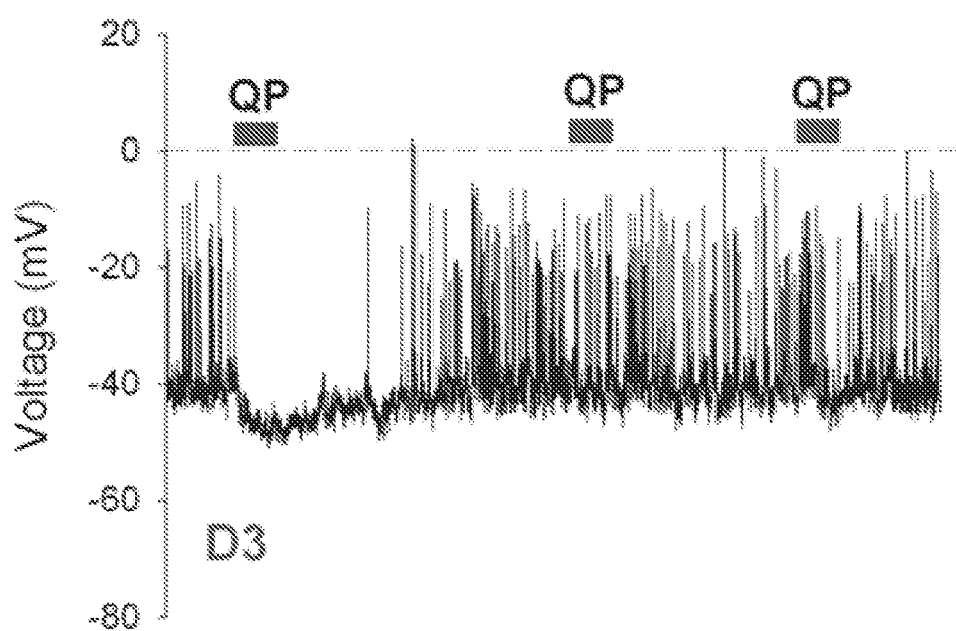

The present invention relates to the discovery that signal transduction pathways for the $D_3$ dopamine receptor (amino acid sequence of SEQ ID NO:1) have specific tolerance and slow response termination (SRT) properties. In a neurological disorder that exhibits altered $D_3$ dopamine receptor expression, the tolerance and slow response termination (SRT) properties are aberrantly expressed and might contribute to the pathology.

In a non-limiting aspect, agonist-induced tolerance in $D_3$ receptors is associated with a unique conformational state of the receptor. This association suggested that the tolerance and SRT properties of the $D_3$ receptor are ligand-dependent and that functionally-selective agonists that altered the tolerance-specific conformation would abolish the tolerance and SRT properties. Screening known $D_3$ receptor agonists and determining their ability to abolish the tolerance and SRT properties allowed the identification of two agonists, cis-8-OH-PBZI (PBZI) and FAUC 73, which while being full agonists at $D_3$ receptors, completely abolished the receptors' tolerance and SRT properties. In order to distinguish these new $D_3$ receptor agonists from classical tolerance- and SRT-inducing agonists, they were collectively named atypical D3 receptor agonists. A pharmacophore model based on the interactions of PBZI with the $D_3$ receptor was designed as an input to the Hybrid Structure Based (HSB) in silico screening method, allowing the identification of an additional novel agonist, ES 609, which also abolished $D_3$ receptor tolerance and SRT properties.

The present invention thus further relates to the discovery of novel functionally-selective $D_3$ dopamine receptor agonists that do not elicit the tolerance and slow response termination properties of $D_3$ receptors. In one aspect, these agonists, rather than preferentially activating signaling pathways, modify the signaling properties of the receptor. In another aspect, this new class of atypical $D_3$ receptor agonists pharmacologically converts the $D_3$ receptor to the functional equivalent of a $D_2$ receptor.

The functional properties of this novel class of atypical $D_3$ receptor agonists was characterized by studying their ability to activate the $D_3$ receptor-adenylyl cyclase and G-protein coupled inward rectifier potassium channel signaling pathways. This novel family of $D_3$ agonists may be used to treat, ameliorate or prevent levodopa-induced dyskinesia (LID) in patients suffering from Parkinson's Disease, or neurological disorders in which there is ectopic overexpression of $D_3$ receptors.

DEFINITIONS

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used.

As used herein, the term "L-DOPA" refers to levodopa, also known as L-3,4-dihydroxyphenylalanine or a salt thereof.

As used herein, the term "quinpirole" or "QP" refers to (4aR,8aR)-5-propyl-4,4a,5,6,7,8,8a,9-octahydro-1H-pyrazolo[3,4-g]quinolone or a salt thereof.

As used herein, the term "GR218231" refers to (+)-(2R)-1,2,3,4-tetrahydro-6-[[(4-methoxyphenyl)sulfonyl] methyl]-N,N-dipropyl-2-naphthalenamine or a salt thereof.

As used herein, the term "PBZI" refers to (3aS, 9bR)-3-propyl-1,2,3a,4,5,9b-hexahydrobenzo[e]indol-8-ol or a salt thereof.

As used herein, the term "clozapine" refers to 8-chloro-11-(4-methylpiperazin-1-yl)-5H-dibenzo[b,e][1,4]diazepine or a salt thereof.

As used herein, the term "WST-1" refers to 2-(4-iodophenyl)-3-(4-nitrophenyl)-5-(2,4-disulfophenyl)-2H-tetrazolium, monosodium salt or a salt thereof.

As used herein, the term "PD128907" refers to (4aR, 10bR)-3,4a,4,10b-tetrahydro-4-propyl-2H,5H-[1]benzopyrano-[4,3-b]-1,4-oxazin-9-ol hydrochloride or a salt thereof.

As used herein, the term "7OH-DPAT" refers to 7-hydroxy-N,N-dipropyl-2-aminotetralin or a salt thereof.

As used herein, the term "6-OHDA" refers to 6-hydroxydopamine or a salt thereof.

As used herein, the term "pramipexole" refers to (S)—$N^6$-propyl-4,5,6,7-tetrahydro-1,3-benzothiazole-2,6-diamine or a salt thereof.

As used herein, the term "rotigotine" refers to (S)-6-[propyl(2-thiophen-2-ylethyl)amino]-5,6,7,8-tetrahydronaphthalen-1-ol or a salt thereof.

As used herein, the term "ES609" or "ES0609" refers to 4-(2-chlorophenyl)-butan-2-amine or a salt thereof.

As used herein, the term "sarizotan" refers to 1-[(2R)-3,4-dihydro-2H-chromen-2-yl]-N-([5-(4-fluorophenyl)pyridin-3-yl]methyl)methanamine or a salt thereof.

As used herein, the term "FAUC73" refers to (4-ethynyl-cyclohex-3-enyl) dipropylamine or a salt thereof.

As used herein, the term "eticlopride" refers to 3-chloro-5-ethyl-N-{[(2S)-1-ethylpyrrolidin-2-yl] methyl}-6-hydroxy-2-methoxybenzamide or a salt thereof As used herein, the term "LID" refers to levodopa-induced dyskinesia.

As used herein, the term "tolerance property" as applying to the $D_3$ receptor refers to the progressive decrease in receptor signaling function upon repeated stimulation by classical agonists, including dopamine.

As used herein, the term "SRT property" or "slow response termination" as applying to the $D_3$ receptor refers to the increase in time taken to terminate the signaling function of the $D_3$ receptor, after removal of the agonist.

As used herein, the term "polypeptide" refers to a polymer composed of amino acid residues, related naturally occurring structural variants, and synthetic non-naturally occurring analogs thereof linked via peptide bonds. Synthetic polypeptides may be synthesized, for example, using an automated polypeptide synthesizer. As used herein, the term "protein" typically refers to large polypeptides. As used herein, the term "peptide" typically refers to short polypeptides. Conventional notation is used herein to represent polypeptide sequences: the left-hand end of a polypeptide sequence is the amino-terminus, and the right-hand end of a polypeptide sequence is the carboxyl-terminus.

As used herein, amino acids are represented by the full name thereof, by the three letter code corresponding thereto, or by the one-letter code corresponding thereto, as indicated below:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

As used herein, the term "treatment" or "treating," is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has LID, a symptom of LID or the potential to develop LID, with the purpose to cure, heal, alleviate, relieve, alter, remedy, ameliorate, improve or affect LID, the symptoms of LID or the potential to develop LID. The term "treatment" or "treating" is also defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has Parkinson's Disease, a symptom of Parkinson's Disease or the potential to develop Parkinson's Disease, with the purpose to cure, heal, alleviate, relieve, alter, remedy, ameliorate, improve or affect Parkinson's Disease, the symptoms of Parkinson's Disease or the potential to develop Parkinson's Disease. Such treatments may be specifically tailored or modified, based on knowledge obtained from the field of pharmacogenomics.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient" or "subject" refers to a human or a non-human mammal. Non-human mammals include, for example, livestock and pets, such as ovine, bovine, porcine, canine, feline and murine mammals. Preferably, the patient or subject is human.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, and phosphoric. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like.

As used herein, the term "composition" or "pharmaceutical composition" refers to a mixture of at least one compound useful within the invention with a pharmaceutically acceptable carrier. The pharmaceutical composition facilitates administration of the compound to a patient. Multiple techniques of administering a compound exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is $(C_1-C_6)$alkyl, particularly ethyl, methyl, isopropyl, isobutyl, n-pentyl, n-hexyl and cyclopropylmethyl.

As used herein, the term "substituted alkyl" means alkyl, as defined above, substituted by one, two or three substituents selected from the group consisting of halogen, —OH, alkoxy, —$NH_2$, —$N(CH_3)_2$, —$C(=O)OH$, trifluoromethyl, —C≡N, —$C(=O)O(C_1-C_4)$alkyl, —$C(=O)NH_2$, —$SO_2NH_2$, —$C(=NH)NH_2$, and —$NO_2$, preferably containing one or two substituents selected from halogen, —OH, alkoxy, —$NH_2$, trifluoromethyl, —$N(CH_3)_2$, and —$C(=O)OH$, more preferably selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are $(C_1-C_3)$ alkoxy, particularly ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$ As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "aryl-($C_1$-$C_3$)alkyl" means a functional group wherein a one to three carbon alkylene chain is attached to an aryl group, e.g., —$CH_2CH_2$-phenyl. Preferred is aryl-$CH_2$- and aryl-$CH(CH_3)$—. The term "substituted aryl-($C_1$-$C_3$)alkyl" means an aryl-($C_1$-$C_3$)alkyl functional group in which the aryl group is substituted. Preferred is substituted aryl($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$)alkyl" means a heteroaryl-($C_1$-$C_3$)alkyl functional group in which the heteroaryl group is substituted. Preferred is substituted heteroaryl-($CH_2$)—.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_{1-6}$ alkyl, —OH, $C_{1-6}$ alkoxy, halo, amino, acetamido and nitro. In yet another embodiment, the substituents are independently selected from the group consisting of $C_{1-6}$ alkyl, $C_{1-6}$ alkoxy, halo, acetamido, and nitro. As used herein, where a substituent is an alkyl or alkoxy group, the carbon chain may be branched, straight or cyclic, with straight being preferred.

"Instructional material," as that term is used herein, includes a publication, a recording, a diagram, or any other medium of expression that may be used to communicate the usefulness of the compounds of the invention. In some instances, the instructional material may be part of a kit useful for effecting alleviating or treating the various diseases or disorders recited herein. Optionally, or alternately, the instructional material may describe one or more methods of alleviating the diseases or disorders in a cell or a tissue of a mammal. The instructional material of the kit may, for example, be affixed to a container that contains the compounds of the invention or be shipped together with a container that contains the compounds. Alternatively, the instructional material may be shipped separately from the container with the intention that the recipient uses the instructional material and the compound cooperatively. For example, the instructional material is for use of a kit; instructions for use of the compound; or instructions for use of a formulation of the compound.

Compounds of the Invention

The compounds useful within the invention may be synthesized using techniques well-known in the art of organic synthesis.

In one aspect, the compound useful within the invention has the formula (I):

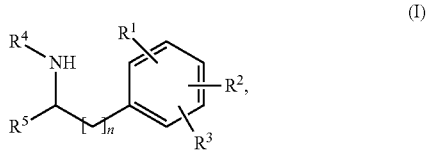

(I)

wherein in formula (I):

- $R^1$, $R^2$ and $R^3$ are independently selected from the group consisting of H, cyano, hydroxyl, amino, acetamido, halo, alkoxy, nitro, $C_{1-6}$ alkyl, substituted $C_{1-6}$ alkyl, heteroalkyl, heterocyclyl, substituted heterocyclyl, aryl, substituted aryl, aryl-($C_{1-3}$)alkyl, substituted aryl-($C_{1-3}$)alkyl, carboxy, alkylcarboxy, formyl, alkyl-carbonyl, aryl-carbonyl, and heteroaryl-carbonyl;
- $R^4$ and $R^5$ are independently selected from the group consisting of H, $C_{1-6}$ alkyl, substituted $C_{1-6}$ alkyl, heteroalkyl, heterocyclyl, substituted heterocyclyl, aryl, substituted aryl, aryl-($C_{1-3}$)alkyl, and substituted aryl-($C_{1-3}$)alkyl; and,
- n is 2, 3, 4 or 5;

or a pharmaceutically acceptable salt thereof.

In one embodiment, $R^1$, $R^2$ and $R^3$ are independently selected from the group consisting of H, cyano, hydroxyl, amino, acetamido, halo, alkoxy, nitro, $C_{1-6}$ alkyl, substituted $C_{1-6}$ alkyl, heteroalkyl, heterocyclyl, substituted heterocyclyl, carboxy, alkylcarboxy, formyl, alkyl-carbonyl, aryl-carbonyl, and heteroaryl-carbonyl. In another embodiment, $R^1$, $R^2$ and $R^3$ are independently selected from the group consisting of H, cyano, hydroxyl, amino, acetamido, halo, alkoxy, nitro, $C_{1-6}$ alkyl, substituted $C_{1-6}$ alkyl, heteroalkyl, carboxy, alkylcarboxy, formyl, and alkyl-carbonyl. In yet another embodiment, $R^1$, $R^2$ and $R^3$ are independently selected from the group consisting of H, cyano, hydroxyl, amino, acetamido, halo, alkoxy, nitro, $C_{1-6}$ alkyl, substituted $C_{1-6}$ alkyl, heteroalkyl, and carboxy. In yet another embodiment, $R^1$, $R^2$ and $R^3$ are independently selected from the group consisting of H, cyano, hydroxyl, amino, acetamido, halo, alkoxy, nitro, $C_{1-6}$ alkyl, and carboxy. In yet another embodiment, $R^1$, $R^2$ and $R^3$ are independently selected from the group consisting of H, cyano, halo, alkoxy, nitro, $C_{1-6}$ alkyl, and carboxy. In yet another embodiment, $R^1$ and $R^2$ are H, and $R^3$ is chloro. In yet another embodiment, $R^1$, $R^2$ and $R^3$ are independently selected from the group consisting of H, fluoro, chloro, bromo, iodo, methoxy, ethoxy, hydroxyl, methyl, ethyl or other $C_{1-6}$ alkyl.

In one embodiment, n is 2, 3 or 4. In another embodiment, n is 2 or 3. In yet another embodiment, n is 2.

In one embodiment, $R^4$ and $R^5$ are independently selected from the group consisting of H, $C_{1-6}$ alkyl, substituted $C_{1-6}$ alkyl, heteroalkyl, heterocyclyl, substituted heterocyclyl, aryl, and substituted aryl. In another embodiment, $R^4$ and $R^5$ are independently selected from the group consisting of H, $C_{1-6}$ alkyl, substituted $C_{1-6}$ alkyl, heteroalkyl, heterocyclyl, and substituted heterocyclyl. In yet another embodiment, $R^4$ and $R^5$ are independently selected from the group consisting of H, $C_{1-6}$ alkyl, substituted $C_{1-6}$ alkyl, and heteroalkyl. In yet another embodiment, $R^4$ and $R^5$ are independently selected from the group consisting of H, $C_{1-6}$ alkyl, and substituted $C_{1-6}$ alkyl. In yet another embodiment, $R^4$ and $R^5$ are methyl. In yet another embodiment, $R^5$ is H, methyl, ethyl, prop-1-yl, prop-2-yl, hydroxymethyl, 1-hydroxyethyl, 2-hydroxy-ethyl, 1-hydroxy-prop-1-yl, 2-hydroxy-prop-1-yl, 3-hydroxy-prop-1-yl, 1-hydroxy-prop-2-yl or 2-hydroxy-prop-2-yl.

In one embodiment, the compound useful within the invention is selected from the group consisting of:

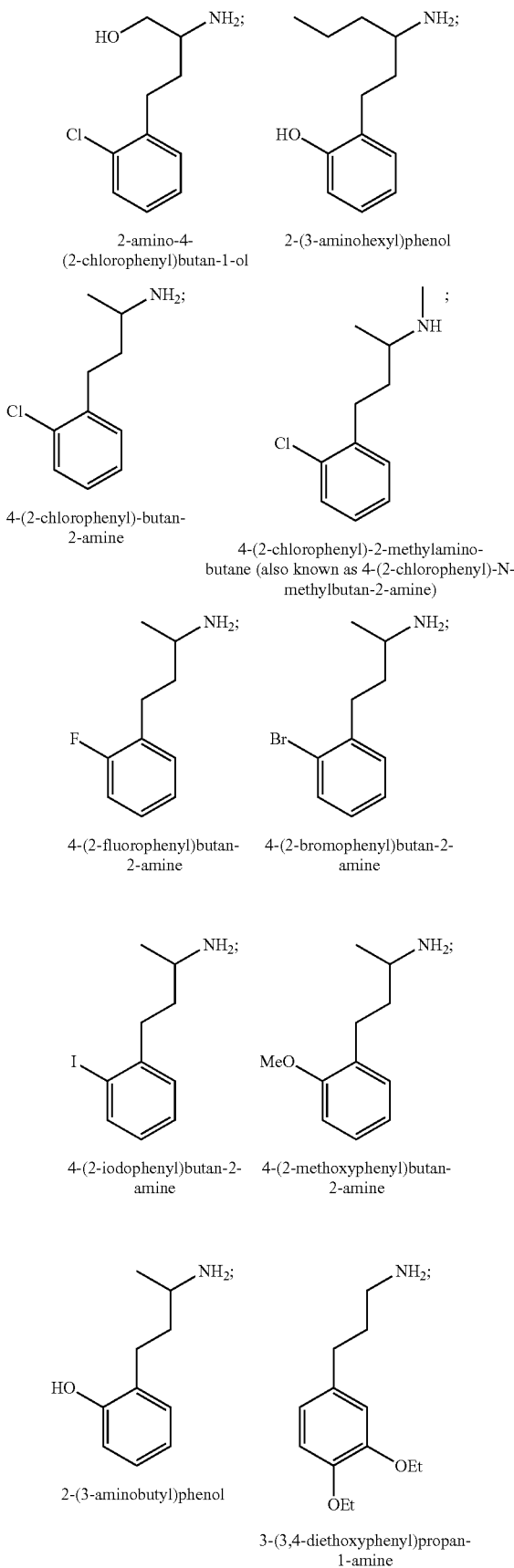

2-amino-4-(2-chlorophenyl)butan-1-ol 2-(3-aminohexyl)phenol 4-(2-chlorophenyl)-butan-2-amine 4-(2-chlorophenyl)-2-methylamino-butane (also known as 4-(2-chlorophenyl)-N-methylbutan-2-amine)

4-(2-fluorophenyl)butan-2-amine 4-(2-bromophenyl)butan-2-amine 4-(2-iodophenyl)butan-2-amine 4-(2-methoxyphenyl)butan-2-amine 2-(3-aminobutyl)phenol 3-(3,4-diethoxyphenyl)propan-1-amine -continued

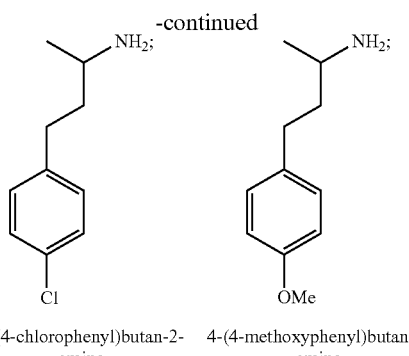

4-(4-chlorophenyl)butan-2-amine    4-(4-methoxyphenyl)butan-2-amine mixtures thereof, or a pharmaceutically acceptable salt thereof.

In another aspect, the compound useful within the invention has the formula (IIa) or (IIb):

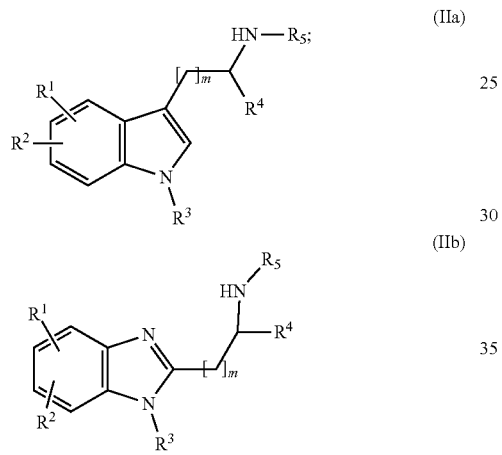

wherein in formula (IIa) or (IIb):
- $R^1$ and $R^2$ are independently selected from the group consisting of H, cyano, hydroxyl, amino, acetamido, halo, alkoxy, nitro, $C_{1-6}$ alkyl, substituted $C_{1-6}$ alkyl, heteroalkyl, heterocyclyl, substituted heterocyclyl, aryl, substituted aryl, aryl-($C_{1-3}$)alkyl, substituted aryl-($C_{1-3}$)alkyl, carboxy, alkylcarboxy, formyl, alkyl-carbonyl, aryl-carbonyl, and heteroaryl-carbonyl;
- $R^3$ and $R^4$ are independently selected from the group consisting of H, $C_{1-6}$ alkyl, aryl, heteroaryl, and substituted $C_{1-6}$ alkyl;
- $R^5$ is selected from the group consisting of H, $C_{1-6}$ alkyl, substituted $C_{1-6}$ alkyl, heteroalkyl, heterocyclyl, substituted heterocyclyl, aryl, substituted aryl, aryl-($C_{1-3}$) alkyl, and substituted aryl-($C_{1-3}$)alkyl; and,
- m is 1, 2, 3 or 4;

or a pharmaceutically acceptable salt thereof.

In one embodiment, $R^1$ and $R^2$ are independently selected from the group consisting of H, cyano, hydroxyl, amino, acetamido, halo, alkoxy, nitro, $C_{1-6}$ alkyl, substituted $C_{1-6}$ alkyl, carboxy, alkylcarboxy, formyl, alkyl-carbonyl, aryl-carbonyl, and heteroaryl-carbonyl. In another embodiment, $R^1$ and $R^2$ are independently selected from the group consisting of H, cyano, hydroxyl, halo, and alkoxy, $C_{1-6}$ alkyl, and substituted $C_{1-6}$ alkyl.

In one embodiment, $R^3$ and $R^4$ are independently selected from the group consisting of H, and $C_{1-6}$ alkyl.

In one embodiment, $R^5$ is selected from the group consisting of H, $C_{1-6}$ alkyl, and substituted $C_{1-6}$ alkyl.

In one embodiment, m is 1, 2 or 3.

In one embodiment, the compound useful within the invention is selected from the group consisting of

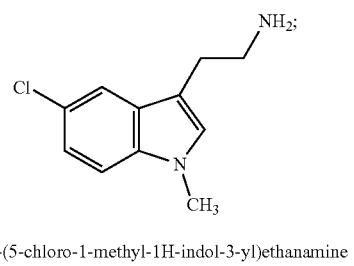

2-(5-chloro-1-methyl-1H-indol-3-yl)ethanamine

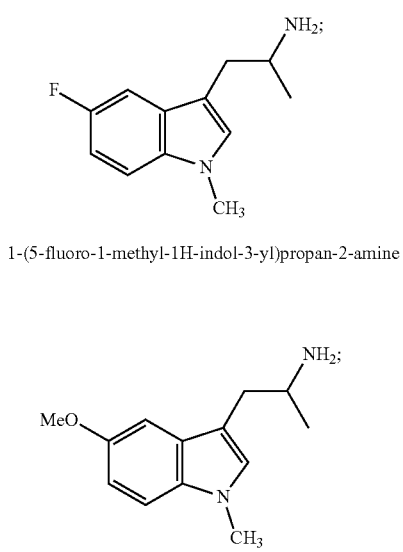

1-(5-fluoro-1-methyl-1H-indol-3-yl)propan-2-amine 1-(5-methoxy-1-methyl-1H-indol-3-yl)propan-2-amine mixtures thereof, or a pharmaceutically acceptable salt thereof.

In yet another aspect, the compound useful within the invention is selected from the group consisting of:

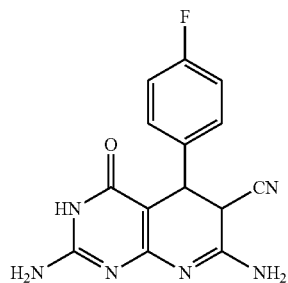

2,7-diamino-5-(4-fluorophenyl)-4-oxo-3,4,5,6-tetrahydropyrido[2,3-d]pyrimidine-6-carbonitrile

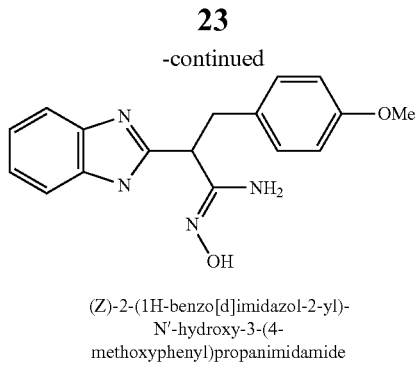

(Z)-2-(1H-benzo[d]imidazol-2-yl)-
N'-hydroxy-3-(4-
methoxyphenyl)propanimidamide mixtures thereof, or a pharmaceutically acceptable salt thereof.

Methods of the Invention

In one aspect, the invention includes a method of treating, ameliorating or preventing levodopa-induced dyskinesia in a patient suffering from Parkinson's Disease. The method comprises administering to the patient a pharmaceutical composition comprising a therapeutically effective amount of at least one compound selected from the group consisting of:

a compound of formula (I):

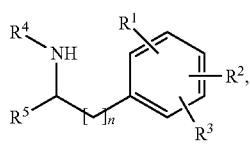

(I)

wherein in formula (I):

$R^1$, $R^2$ and $R^3$ are independently selected from the group consisting of H, cyano, hydroxyl, amino, acetamido, halo, alkoxy, nitro, $C_{1-6}$ alkyl, substituted $C_{1-6}$ alkyl, heteroalkyl, heterocyclyl, substituted heterocyclyl, aryl, substituted aryl, aryl-($C_{1-3}$)alkyl, substituted aryl-($C_{1-3}$)alkyl, carboxy, alkylcarboxy, formyl, alkyl-carbonyl, aryl-carbonyl, and heteroaryl-carbonyl;

$R^4$ and $R^5$ are independently selected from the group consisting of H, $C_{1-6}$ alkyl, substituted $C_{1-6}$ alkyl, heteroalkyl, heterocyclyl, substituted heterocyclyl, aryl, substituted aryl, aryl-($C_{1-3}$)alkyl, and substituted aryl-($C_{1-3}$)alkyl; and, n is 2, 3, 4 or 5;

a compound of formula (IIa) or (IIb):

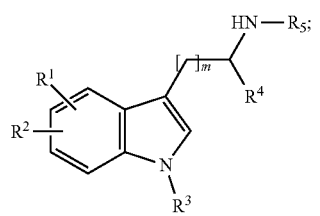

(IIa)

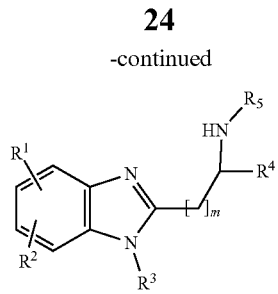

(IIb)

wherein in formula (IIa) or (IIb):

$R^1$ and $R^2$ are independently selected from the group consisting of H, cyano, hydroxyl, amino, acetamido, halo, alkoxy, nitro, $C_{1-6}$ alkyl, substituted $C_{1-6}$ alkyl, heteroalkyl, heterocyclyl, substituted heterocyclyl, aryl, substituted aryl, aryl-($C_{1-3}$)alkyl, substituted aryl-($C_{1-3}$)alkyl, carboxy, alkylcarboxy, formyl, alkyl-carbonyl, aryl-carbonyl, and heteroaryl-carbonyl;

$R^3$ and $R^4$ are independently selected from the group consisting of H, $C_{1-6}$ alkyl, aryl, heteroaryl, and substituted $C_{1-6}$ alkyl;

$R^5$ is selected from the group consisting of H, $C_{1-6}$ alkyl, substituted $C_{1-6}$ alkyl, heteroalkyl, heterocyclyl, substituted heterocyclyl, aryl, substituted aryl, aryl-($C_{1-3}$) alkyl, and substituted aryl-($C_{1-3}$)alkyl; and, m is 1, 2, 3 or 4;

2,7-diamino-5-(4-fluorophenyl)-4-oxo-3,4,5,6-tetrahydro-pyrido[2,3-d]pyrimidine-6-carbonitrile; (Z)-2-(1H-benzo[d]imidazol-2-yl)-N'-hydroxy-3-(4-methoxyphenyl)propanimidamide; mixtures thereof, or a pharmaceutically acceptable salt thereof.

In one embodiment, $R^1$, $R^2$ and $R^3$ are independently selected from the group consisting of H, cyano, hydroxyl, amino, acetamido, halo, alkoxy, nitro, $C_{1-6}$ alkyl, substituted $C_{1-6}$ alkyl, heteroalkyl, heterocyclyl, substituted heterocyclyl, carboxy, alkylcarboxy, formyl, alkyl-carbonyl, aryl-carbonyl, and heteroaryl-carbonyl. In another embodiment, $R^1$, $R^2$ and $R^3$ are independently selected from the group consisting of H, cyano, hydroxyl, amino, acetamido, halo, alkoxy, nitro, $C_{1-6}$ alkyl, substituted $C_{1-6}$ alkyl, heteroalkyl, carboxy, alkylcarboxy, formyl, and alkyl-carbonyl. In yet another embodiment, $R^1$, $R^2$ and $R^3$ are independently selected from the group consisting of H, cyano, hydroxyl, amino, acetamido, halo, alkoxy, nitro, $C_{1-6}$ alkyl, substituted $C_{1-6}$ alkyl, heteroalkyl, and carboxy. In yet another embodiment, $R^1$, $R^2$ and $R^3$ are independently selected from the group consisting of H, cyano, hydroxyl, amino, acetamido, halo, alkoxy, nitro, $C_{1-6}$ alkyl, and carboxy. In yet another embodiment, $R^1$, $R^2$ and $R^3$ are independently selected from the group consisting of H, cyano, halo, alkoxy, nitro, $C_{1-6}$ alkyl, and carboxy. In yet another embodiment, $R^1$ and $R^2$ are H, and $R^3$ is chloro. In yet another embodiment, $R^1$, $R^2$ and $R^3$ are independently selected from the group consisting of H, fluoro, chloro, bromo, iodo, methoxy, and ethoxy.

In one embodiment, $R^1$ and $R^2$ are independently selected from the group consisting of H, cyano, hydroxyl, amino, acetamido, halo, alkoxy, nitro, $C_{1-6}$ alkyl, substituted $C_{1-6}$ alkyl, carboxy, alkylcarboxy, formyl, alkyl-carbonyl, aryl-carbonyl, and heteroaryl-carbonyl. In another embodiment, $R^1$ and $R^2$ are independently selected from the group consisting of H, cyano, hydroxyl, halo, and alkoxy, $C_{1-6}$ alkyl, and substituted $C_{1-6}$ alkyl.

In one embodiment, n is 2, 3 or 4. In another embodiment, n is 2 or 3. In yet another embodiment, n is 2.

In one embodiment, $R^4$ and $R^5$ are independently selected from the group consisting of H, $C_{1-6}$ alkyl, substituted $C_{1-6}$ alkyl, heteroalkyl, heterocyclyl, substituted heterocyclyl, aryl, and substituted aryl. In another embodiment, $R^4$ and $R^5$ are independently selected from the group consisting of H, $C_{1-6}$ alkyl, substituted $C_{1-6}$ alkyl, heteroalkyl, heterocyclyl, and substituted heterocyclyl. In yet another embodiment, $R^4$ and $R^5$ are independently selected from the group consisting of H, $C_{1-6}$ alkyl, substituted $C_{1-6}$ alkyl, and heteroalkyl. In yet another embodiment, $R^4$ and $R^5$ are independently selected from the group consisting of H, $C_{1-6}$ alkyl, and substituted $C_{1-6}$ alkyl. In yet another embodiment, $R^4$ and $R^5$ are methyl. In yet another embodiment, $R^5$ is H, methyl, ethyl, prop-1-yl, prop-2-yl, hydroxymethyl, 1-hydroxy-ethyl, 2-hydroxy-ethyl, 1-hydroxy-prop-1-yl, 2-hydroxy-prop-1-yl, 3-hydroxy-prop-1-yl, 1-hydroxy-prop-2-yl or 2-hydroxy-prop-2-yl.

In one embodiment, $R^3$ and $R^4$ are independently selected from the group consisting of H, and $C_{1-6}$ alkyl.

In one embodiment, $R^5$ is selected from the group consisting of H, $C_{1-6}$ alkyl, and substituted $C_{1-6}$ alkyl.

In one embodiment, m is 1, 2 or 3.

In one embodiment, the compound useful within the invention is selected from the group consisting of: 2-amino-4-(2-chlorophenyl)butan-1-ol; 2-(3-aminohexyl)phenol; 4-(2-chlorophenyl)-butan-2-amine; 4-(2-chlorophenyl)-2-methylamino-butane; 4-(2-fluorophenyl)butan-2-amine; 4-(2-bromophenyl)butan-2-amine; 4-(2-iodophenyl)butan-2-amine; 4-(2-methoxyphenyl)butan-2-amine; 2-(3-aminobutyl)phenol; 3-(3,4-diethoxyphenyl)propan-1-amine; 4-(4-chlorophenyl)butan-2-amine; 4-(4-methoxyphenyl)butan-2-amine; 2-(5-chloro-1-methyl-1H-indol-3-yl)ethanamine; 1-(5-fluoro-1-methyl-1H-indol-3-yl)propan-2-amine; 1-(5-methoxy-1-methyl-1H-indol-3-yl)propan-2-amine; 2,7-diamino-5-(4-fluorophenyl)-4-oxo-3,4,5,6-tetrahydropyrido[2,3-d]pyrimidine-6-carbonitrile; (Z)-2-(1H-benzo[d]imidazol-2-yl)-N'-hydroxy-3-(4-methoxyphenyl)propanimidamide;

mixtures thereof, or a pharmaceutically acceptable salt thereof.

In one embodiment, the composition further comprises a drug selected from the group consisting of levodopa, clozapine, bromocriptine, pergolide, pramipexole, ropinirole, piribedil, cabergoline, apomorphine, and lisuride, a salt thereof and mixtures thereof. In another embodiment, the pharmaceutical composition is co-administered to the patient with a second pharmaceutical composition comprising levodopa. In yet another embodiment, the pharmaceutical composition is administered to the patient a given period of time before a second pharmaceutical composition comprising levodopa is administered to the patient. In yet another embodiment, the given period of time varies from about 2 minutes to about 24 hours. In yet another embodiment, the patient is human.

In another aspect, the invention includes a method of treating, ameliorating or preventing Parkinson's Disease in a patient. The method comprises administering to the patient a pharmaceutical composition comprising a therapeutically effective amount of at least one compound selected from the group consisting of:

a compound of formula (I):

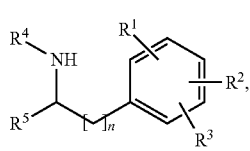

(I)

wherein in formula (I):
$R^1$, $R^2$ and $R^3$ are independently selected from the group consisting of H, cyano, hydroxyl, amino, acetamido, halo, alkoxy, nitro, $C_{1-6}$ alkyl, substituted $C_{1-6}$ alkyl, heteroalkyl, heterocyclyl, substituted heterocyclyl, aryl, substituted aryl, aryl-($C_{1-3}$)alkyl, substituted aryl-($C_{1-3}$)alkyl, carboxy, alkylcarboxy, formyl, alkyl-carbonyl, aryl-carbonyl, and heteroaryl-carbonyl;

$R^4$ and $R^5$ are independently selected from the group consisting of H, $C_{1-6}$ alkyl, substituted $C_{1-6}$ alkyl, heteroalkyl, heterocyclyl, substituted heterocyclyl, aryl, substituted aryl, aryl-($C_{1-3}$)alkyl, and substituted aryl-($C_{1-3}$)alkyl; and, n is 2, 3, 4 or 5;

a compound of formula (IIa) or (IIb):

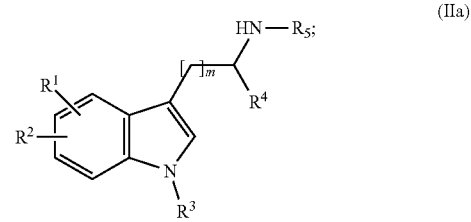

(IIa)

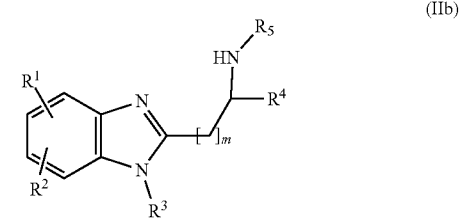

(IIb)

wherein in formula (IIa) or (IIb):
$R^1$ and $R^2$ are independently selected from the group consisting of H, cyano, hydroxyl, amino, acetamido, halo, alkoxy, nitro, $C_{1-6}$ alkyl, substituted $C_{1-6}$ alkyl, heteroalkyl, heterocyclyl, substituted heterocyclyl, aryl, substituted aryl, aryl-($C_{1-3}$)alkyl, substituted aryl-($C_{1-3}$)alkyl, carboxy, alkylcarboxy, formyl, alkyl-carbonyl, aryl-carbonyl, and heteroaryl-carbonyl;

$R^3$ and $R^4$ are independently selected from the group consisting of H, $C_{1-6}$ alkyl, aryl, heteroaryl, and substituted $C_{1-6}$ alkyl;

$R^5$ is selected from the group consisting of H, $C_{1-6}$ alkyl, substituted $C_{1-6}$ alkyl, heteroalkyl, heterocyclyl, substituted heterocyclyl, aryl, substituted aryl, aryl-($C_{1-3}$)alkyl, and substituted aryl-($C_{1-3}$)alkyl; and, m is 1, 2, 3 or 4;

2,7-diamino-5-(4-fluorophenyl)-4-oxo-3,4,5,6-tetrahydropyrido[2,3-d]pyrimidine-6-carbonitrile; (Z)-2-(1H-benzo[d]imidazol-2-yl)-N'-hydroxy-3-(4-methoxyphenyl)propanimidamide; mixtures thereof, or a pharmaceutically acceptable salt thereof.

In one embodiment, $R^1$, $R^2$ and $R^3$ are independently selected from the group consisting of H, cyano, hydroxyl, amino, acetamido, halo, alkoxy, nitro, $C_{1-6}$ alkyl, substituted $C_{1-6}$ alkyl, heteroalkyl, heterocyclyl, substituted heterocyclyl, carboxy, alkylcarboxy, formyl, alkyl-carbonyl, aryl-carbonyl, and heteroaryl-carbonyl. In another embodiment, $R^1$, $R^2$ and $R^3$ are independently selected from the group consisting of H, cyano, hydroxyl, amino, acetamido, halo, alkoxy, nitro, $C_{1-6}$ alkyl, substituted $C_{1-6}$ alkyl, heteroalkyl, carboxy, alkylcarboxy, formyl, and alkyl-carbonyl. In yet another embodiment, $R^1$, $R^2$ and $R^3$ are independently selected from the group consisting of H, cyano, hydroxyl, amino, acetamido, halo, alkoxy, nitro, $C_{1-6}$ alkyl, substituted $C_{1-6}$ alkyl, heteroalkyl, and carboxy. In yet another embodiment, $R^1$, $R^2$ and $R^3$ are independently selected from the group consisting of H, cyano, hydroxyl, amino, acetamido, halo, alkoxy, nitro, $C_{1-6}$ alkyl, and carboxy. In yet another embodiment, $R^1$, $R^2$ and $R^3$ are independently selected from the group consisting of H, cyano, halo, alkoxy, nitro, $C_{1-6}$ alkyl, and carboxy. In yet another embodiment, $R^1$ and $R^2$ are H, and $R^3$ is chloro. In yet another embodiment, $R^1$, $R^2$ and $R^3$ are independently selected from the group consisting of H, fluoro, chloro, bromo, iodo, methoxy, and ethoxy.

In one embodiment, $R^1$ and $R^2$ are independently selected from the group consisting of H, cyano, hydroxyl, amino, acetamido, halo, alkoxy, nitro, $C_{1-6}$ alkyl, substituted $C_{1-6}$ alkyl, carboxy, alkylcarboxy, formyl, alkyl-carbonyl, aryl-carbonyl, and heteroaryl-carbonyl. In another embodiment, $R^1$ and $R^2$ are independently selected from the group consisting of H, cyano, hydroxyl, halo, and alkoxy, $C_{1-6}$ alkyl, and substituted $C_{1-6}$ alkyl.

In one embodiment, n is 2, 3 or 4. In another embodiment, n is 2 or 3. In yet another embodiment, n is 2.

In one embodiment, $R^4$ and $R^5$ are independently selected from the group consisting of H, $C_{1-6}$ alkyl, substituted $C_{1-6}$ alkyl, heteroalkyl, heterocyclyl, substituted heterocyclyl, aryl, and substituted aryl. In another embodiment, $R^4$ and $R^5$ are independently selected from the group consisting of H, $C_{1-6}$ alkyl, substituted $C_{1-6}$ alkyl, heteroalkyl, heterocyclyl, and substituted heterocyclyl. In yet another embodiment, $R^4$ and $R^5$ are independently selected from the group consisting of H, $C_{1-6}$ alkyl, substituted $C_{1-6}$ alkyl, and heteroalkyl. In yet another embodiment, $R^4$ and $R^5$ are independently selected from the group consisting of H, $C_{1-6}$ alkyl, and substituted $C_{1-6}$ alkyl. In yet another embodiment, $R^4$ and $R^5$ are methyl. In yet another embodiment, $R^5$ is H, methyl, ethyl, prop-1-yl, prop-2-yl, hydroxymethyl, 1-hydroxy-ethyl, 2-hydroxy-ethyl, 1-hydroxy-prop-1-yl, 2-hydroxy-prop-1-yl, 3-hydroxy-prop-1-yl, 1-hydroxy-prop-2-yl or 2-hydroxy-prop-2-yl.

In one embodiment, $R^3$ and $R^4$ are independently selected from the group consisting of H, and $C_{1-6}$ alkyl.

In one embodiment, $R^5$ is selected from the group consisting of H, $C_{1-6}$ alkyl, and substituted $C_{1-6}$ alkyl.

In one embodiment, m is 1, 2 or 3.

In one embodiment, the compound useful within the invention is selected from the group consisting of: 2-amino-4-(2-chlorophenyl)butan-1-ol; 2-(3-aminohexyl)phenol; 4-(2-chlorophenyl)-butan-2-amine; 4-(2-chlorophenyl)-2-methylamino-butane; 4-(2-fluorophenyl)butan-2-amine; 4-(2-bromophenyl)butan-2-amine; 4-(2-iodophenyl)butan-2-amine; 4-(2-methoxyphenyl)butan-2-amine; 2-(3-aminobutyl)phenol; 3-(3,4-diethoxyphenyl)propan-1-amine; 4-(4-chlorophenyl)butan-2-amine; 4-(4-methoxyphenyl)butan-2-amine; 2-(5-chloro-1-methyl-1H-indol-3-yl)ethanamine; 1-(5-fluoro-1-methyl-1H-indol-3-yl)propan-2-amine; 1-(5-methoxy-1-methyl-1H-indol-3-yl)propan-2-amine; 2,7-diamino-5-(4-fluorophenyl)-4-oxo-3,4,5,6-tetrahydropyrido[2,3-d]pyrimidine-6-carbonitrile; (Z)-2-(1H-benzo[d]imidazol-2-yl)-N'-hydroxy-3-(4-methoxyphenyl)propanimidamide; mixtures thereof, or a pharmaceutically acceptable salt thereof.

In one embodiment, the composition further comprises a drug selected from the group consisting of levodopa, clozapine, bromocriptine, pergolide, pramipexole, ropinirole, piribedil, cabergoline, apomorphine, and lisuride, a salt thereof and mixtures thereof. In another embodiment, the patient is further administered a composition comprising a drug selected from the group consisting of levodopa, clozapine, bromocriptine, pergolide, pramipexole, ropinirole, piribedil, cabergoline, apomorphine, and lisuride, a salt thereof and mixtures thereof.

Molecular Basis of LID in Patients Suffering from Parkinson's Disease

The molecular mechanisms underlying the development of LID in patients suffering from Parkinson's Disease are still not well understood. Studies have shown that expression of a number of genes is altered in dyskinetic animals. In particular, in both rodents and primates, studies have reported a specific increase in the $D_3$ dopamine receptor expression in the basal ganglia of dyskinetic animals. The functional consequence of the increased $D_3$ receptor expression, in areas that normally express the $D_2$ dopamine receptor, is not known.

According to the concept of functional selectivity, ligands may differentially activate signaling pathways coupled to a single GPCR (Kenakin, 2003, Trends Pharmacol. Sci. 24(7): 346-354; Urban et al., 2007, J. Pharmacol. Exp. Ther. 320(1):1-13). Functional selectivity has been previously reported for $D_2$ receptors (Gay et al., 2004, Mol. Pharmacol. 66(1):97-105). Sarizotan, a ligand with affinity at $D_2$-like dopamine receptors, exhibits functional selectivity at $D_{2L}$ and $D_{4.2}$ dopamine receptors (Kuzhikandathil & Bartoszyk, 2006, Neuropharmacology 51:873-884). Sarizotan is a partial agonist for the $D_{2L}$- and $D_{4.2}$-GIRK channel signaling pathway but a full agonist at the $D_{2L}$- and $D_{4.2}$-adenylyl cyclase pathway (Kuzhikandathil & Bartoszyk, 2006, Neuropharmacology 51:873-884). Subsequent studies revealed that sarizotan induces tolerance and slow response termination (SRT) properties on $D_{2S}$ dopamine receptors. This suggests that, in addition to differentially activating signaling pathways, certain agonists could modulate intrinsic receptor properties such as the tolerance and slow response termination properties.

The $D_3$ dopamine receptor exhibits tolerance and slow response termination (SRT) properties that distinguish it from the $D_2$ dopamine receptors (FIGS. 1A-1D). The tolerance property of $D_3$ receptor describes the progressive decrease in receptor signaling function upon repeated stimulation by classical agonists, including dopamine. The SRT property describes the prolongation of time taken to terminate the signaling function of the $D_3$ receptor, after removal of the agonist.

$D_3$ receptor tolerance and SRT has been observed in cultured substantia nigra neurons, and with human and mouse $D_3$ receptors heterologously expressed in *Xenopus* oocytes, CHO-K1 cells and AtT-20 cells. Tolerance and SRT properties are elicited by the native agonist dopamine and by various synthetic agonists tested to date. The tolerance and SRT properties of $D_3$ receptors are elicited over a broad range of agonist concentrations, being observed at 10, 30, 100 and 1000 nM. The properties are manifest in $D_3$-GIRK, $D_3$-ACV and $D_3$-MAP kinase signaling pathways.

Differences in the properties of $D_2$ and $D_3$ receptors give rise to a differential modulation of neuronal firing (FIGS. 1A-1D). These results suggest a model in which aberrant expression of $D_3$ receptor tolerance and SRT properties could result in aberrant modulation of neuronal firing in the basal ganglia of the dyskinetic animals and contribute to the development of LID in Parkinson's Disease. According to this model, if $D_3$ receptor tolerance and SRT properties could be abolished, the modulation of neuronal firing by the over-expressed $D_3$ receptor in the basal ganglia of dyskinetic animals would be similar to the natively expressed $D_2$ receptors and potentially prevent the expression of dyskinesia.

Initial Studies on Dopamine D3 Agonists

To identify agonists that could abolish the $D_3$ dopamine receptor tolerance and SRT, synthetic $D_3$ receptor-preferring agonists were functionally screened. The functional activity of the compounds were tested by stimulating human $D_2$, $D_3$ and $D_4$ dopamine receptors individually expressed in the AtT-20 cell line. These dopamine receptors couple to and activate the G-protein coupled inward rectifier potassium (GIRK) channels and also inhibit the endogenous adenylyl cyclase in AtT-20 cells (Kuzhikandathil et al., 2004, Mol. Cell. Neurosci. 26:144-155; Westrich & Kuzhikandathil, 2007, Biochim. Biophys. Acta-Mol. Cell Res. 1773:1747-1758).

The activation of the GIRK channels was measured electrophysiologically using whole cell voltage clamp recording (Kuzhikandathil et al., 2004, Mol. Cell. Neurosci. 26:144-155). The GIRK channel responses elicited with new ligands were compared to quinpirole, a classical full agonist of $D_2$, $D_3$ and $D_4$ dopamine receptors. The adenylyl cyclase inhibition was determined using a commercially available ELISA assay (Westrich & Kuzhikandathil, 2007, Biochim. Biophys. Acta-Mol. Cell Res. 1773:1747-1758).

Figure 2A:
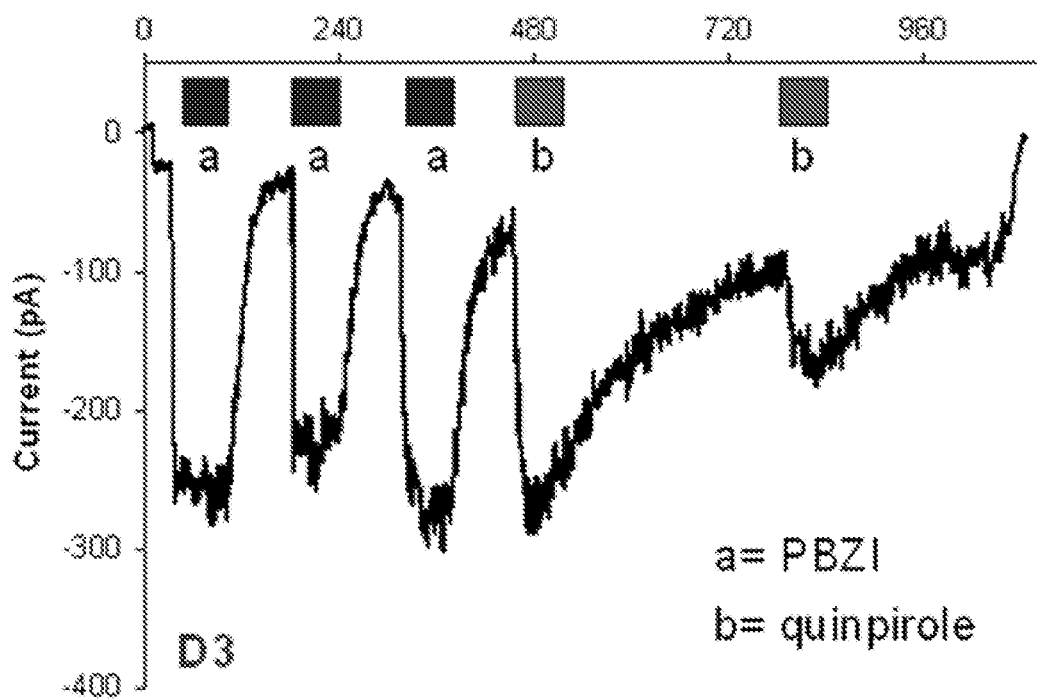
FIGS. 2A-2C illustrate agonist-induced modulation of $D_3$ receptor tolerance and SRT properties. Representative voltage clamp (FIG. 2A) and current clamp recording (FIG. 2B) from AtT-$D_3$ cells treated with 300 nM PBZI ((3aS, 9bR)-3-propyl-1,2,3a,4,5,9b-hexahydrobenzo[e]indol-8-ol) or 100 nM quinpirole ((4aR,8aR)-5-propyl-4,4a,5,6,7,8,8a,9-octahydro-1H-pyrazolo[3,4-g]quinoline) are illustrated. PBZI elicited 3 responses that did not show either tolerance or SRT properties; on the same cell, quinpirole elicited GIRK response with tolerance and SRT. Similarly, representative voltage clamp recordings illustrated in FIG. 2C show that 300 nM FAUC73 (square crossed bar) induces GIRK currents that do not show $D_3$ receptor tolerance and SRT. In contrast, in the same cell, 300 nM PD128907 (black bar) elicited tolerance and SRT. The cells were held at −65 mV and the duration of agonist application was ~60 seconds.
Figure 2B:
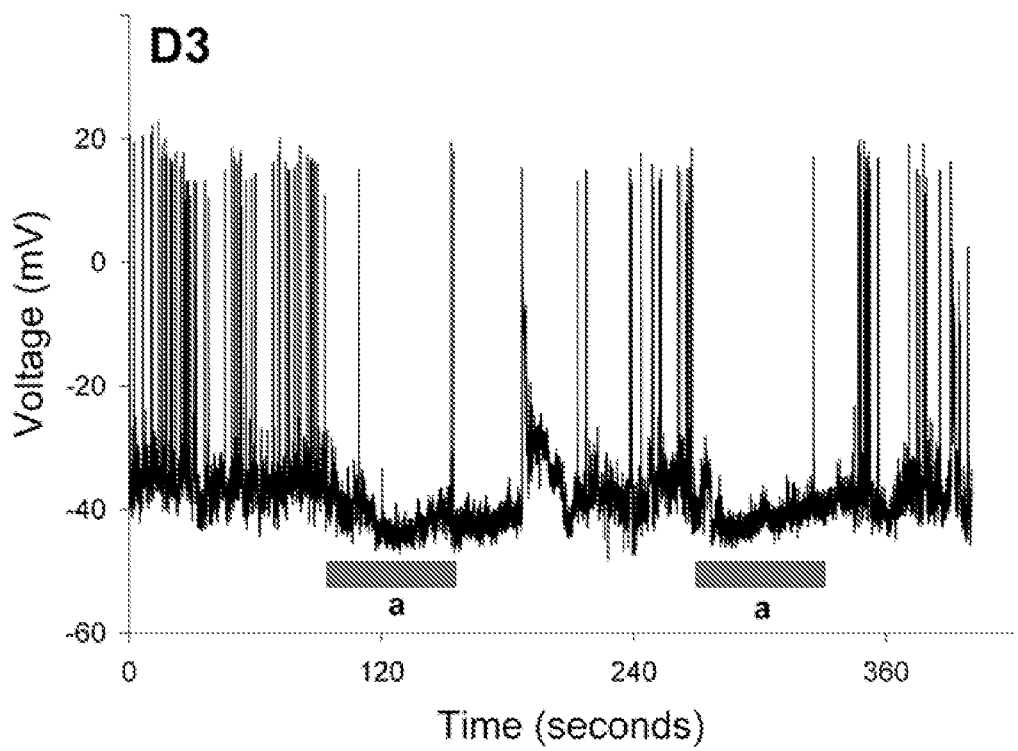
Figure 2C:
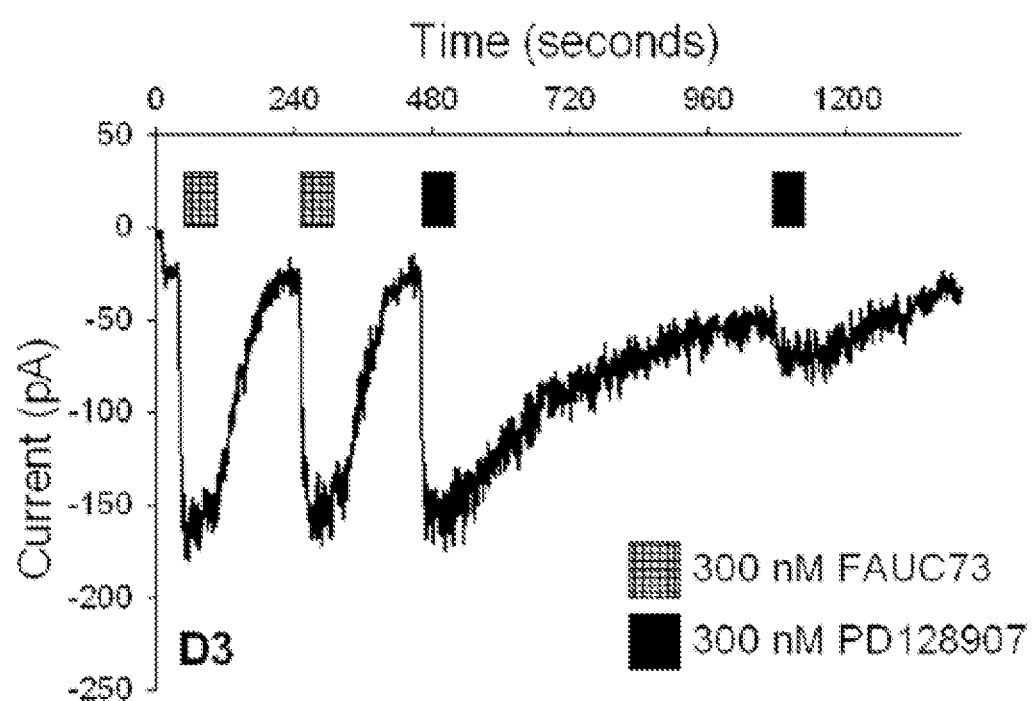

An initial functional screen identified cis-8-hydroxy-3-(n-propyl)-1,2,3a,4,5,9b-hexahydro-1H-benz[e]indole hydrobromide (PBZI). This compound has been reported as a $D_3$ dopamine receptor agonist; nevertheless, the present studies indicate that, unlike traditional $D_3$ receptor agonists, PBZI does not elicit tolerance and SRT properties (FIGS. 2A-2C).

Hybrid Structure Based (HSB) Protocol

Figure 3:
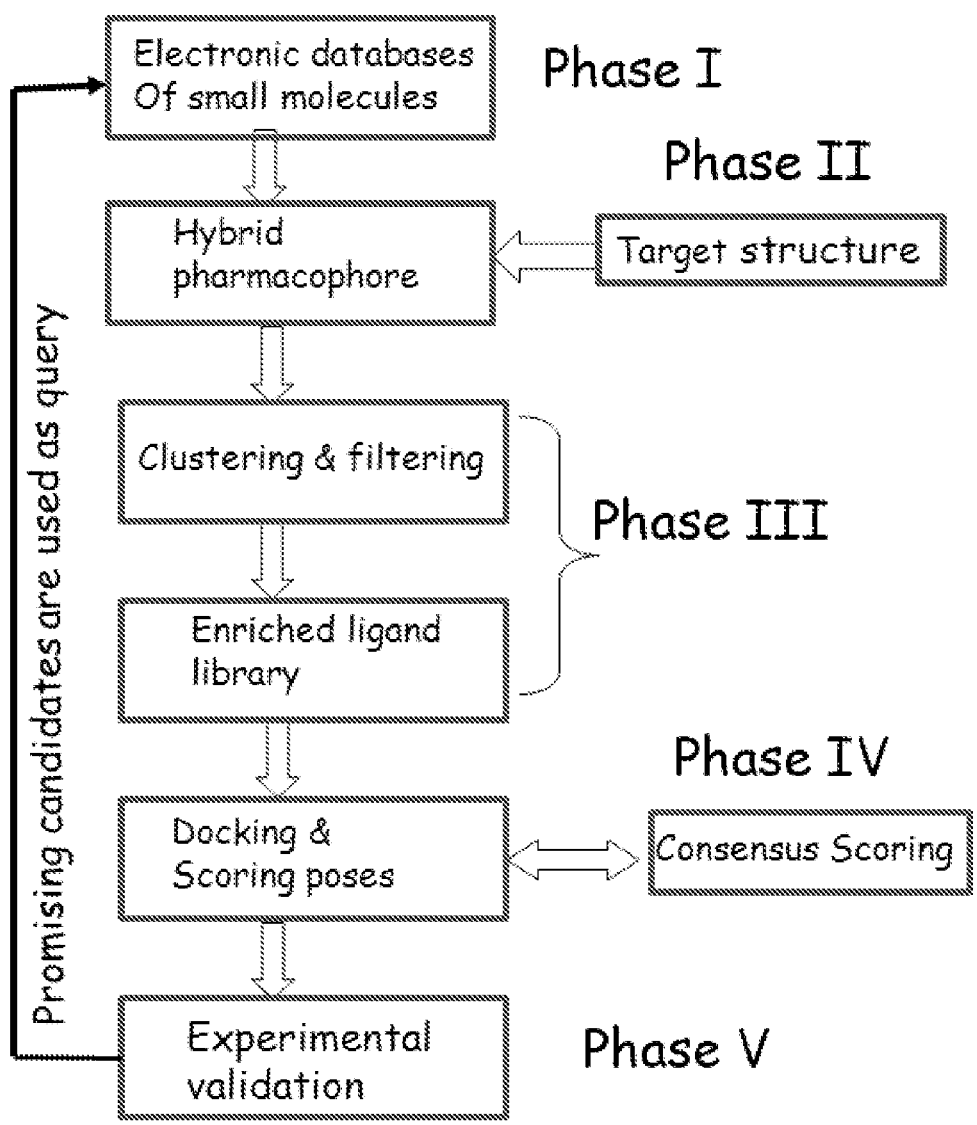
FIG. 3 is a flowchart illustration of the hybrid structure based (HSB) protocol that was used to design these novel $D_3$ agonists.

The Hybrid Structure Based (HSB) protocol (Koratgere & Welsh, 2006, J. Comp. Aided Mol. Des. 20:789-802; FIG. 3) was used to identify additional compounds belonging to the novel class of $D_3$ receptor agonists that do not elicit tolerance and SRT properties. The HSB protocol consists of 5 sub-phases (FIG. 3). Phase I corresponds to building a comprehensive electronic database of vendor available small molecules. Phase II corresponds to developing and screening compounds using a hybrid pharmacophore starting from the 3D structural snapshots from the MD simulation. Phase III corresponds to subjecting compounds that pass the hybrid pharmacophore screening to clustering, filtering, chemical space analysis and classification models to develop the enriched database of small molecules. Phase IV corresponds to docking molecules from the enriched database to the DRD3 receptor, with scores derived from consensus scoring schemes. Phase V corresponds to testing best ranking compounds for their activity against all the dopamine receptors.

Develop Comprehensive Electronic Database of Small Molecules:

A subset of the Zinc database (Irwin & Soichet, 2005, J. Chem. Inf. Models 45:177-82) consisting of compounds from commercial vendors, along with other compounds including natural products, ligands from PDB and FDA approved drugs, form the entire database of nearly 3 million compounds. All compounds were acquired as sdf formatted files, converted into Mol2 format and energy minimized using Tripos force field. Further, all molecules in the database were filtered for redundancy and renamed according to their corresponding vendor listing.

Develop a Combined Ligand-Protein Pharmacophore:

Generating the combined pharmacophore (also called the hybrid pharmacophore) is an important step of the method. Hence, customizing the pharmacophore to capture the essential features of interactions between PBZI and $D_3$ receptor is important.

Such information was obtained from the 3D structural complex of PBZI-$D_3$ receptor complex. The homology model of $D_3$ receptor was built using the crystal structure of beta2 adrenergic receptor (B2AR) with a partial inverse agonist bound to it (2RH1) (Cherezov et al., 2007, Science 318(5854):1258-65). The transmembrane (TM) regions and the loop regions bore significant homology to the corresponding residues from the beta adrenergic crystal structure. The third intracellular loop in the B2AR was longer than the corresponding loop in the $D_3$ receptor and hence a large deletion shown in the alignment (FIG. 4) was not modeled. However, the rest of the third intracellular loop, shown to be very significant for the SRT and receptor tolerance, was modeled using the aligned coordinates from the B2AR structure. Further the entire structure was refined using energy minimization and molecular dynamics simulation with a 2 ns long production run. All simulations were performed using NAMD (Kalé et al., 1999, J. Comput. Physics 151(1):283-312) with CHARMM force field (Brooks et al., 1983, J. Comput. Chem. 4:187-217).

Figure 5:
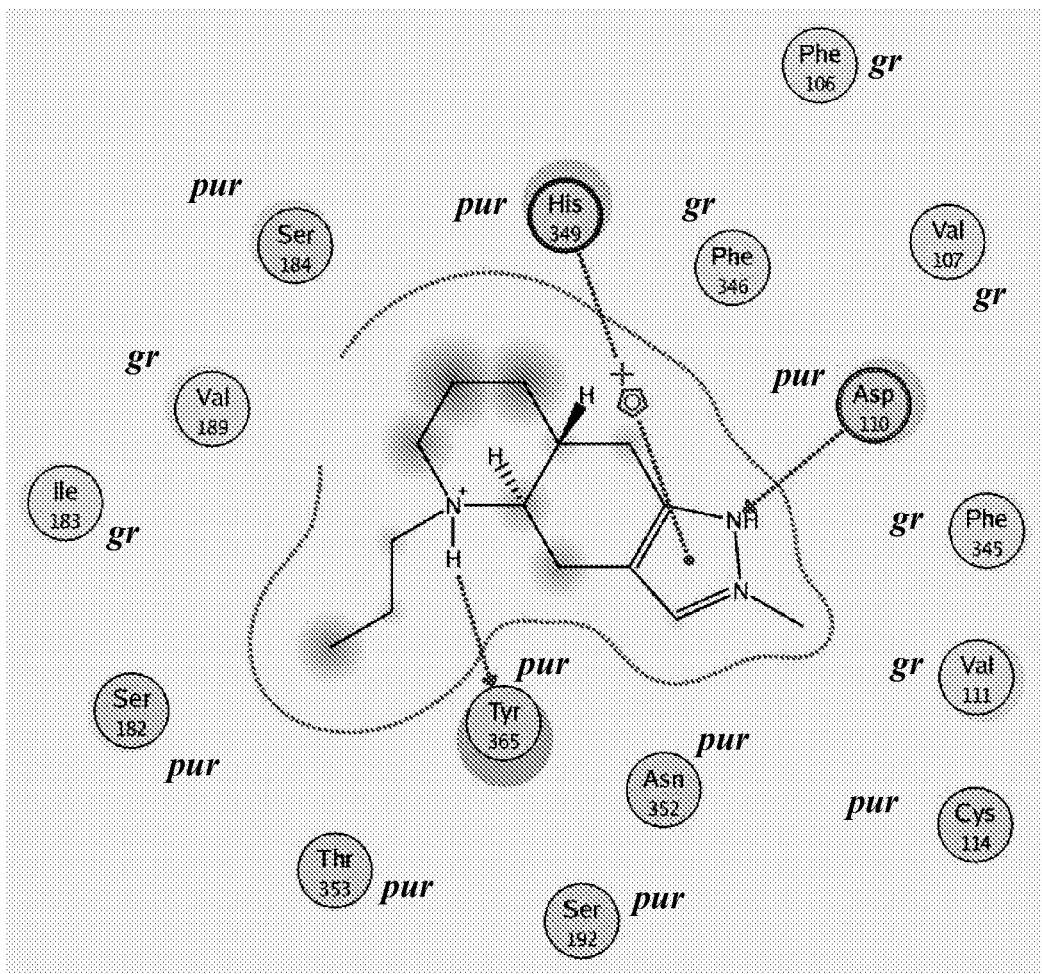
FIG. 5 is a schematic representation of PBZI binding to the $D_3$ receptor with the pharmacophore elements superimposed. Unfilled ovals labeled "gr" represent hydrophobic elements, unfilled ovals labeled "pur" represent hydrogen bond donor-acceptor pairs, and distance constraints are represented by dotted black lines. Hydrogen bonded interactions are shown by arrows, ionic interactions in lines and pi-pi interactions in lines extending across the two six membered rings. Gray spheres and contours indicate matching regions between ligand and receptors.

The refined structure was used for further docking experiments. Dopamine, PD128907 and PBZI were docked using GOLD program (ver4.0) (Jones et al., 1997, J. Mol. Biol. 267:727-48). The docked complexes were energy minimized using NAMD program. Key interactions between PBZI and the $D_3$ receptor were used to build the hybrid pharmacophore (FIG. 5). Various pharmacophore models were generated involving a combination of the four pharmacophore elements that are key to designing $D_3$ receptor agonists, such as the salt bridge with the aspartic acid in TM3 and hydrophobic interactions with the aromatic amino acid cluster from TM5 and TM6. Further, a small interchange of residues between TM2 and TM3 was shown to be instrumental in designing highly selective $D_4$ agonists and antagonist (Kortagere et al., 2004, Mol. Pharmacol. 66:1491-99). These biochemical and functional evidence were integrated into the design of the hybrid pharmacophore, which was then used to screen small molecule databases (which were described above).

A preliminary screening using the hydrophobic core and the two hydrogen bond acceptor-donor pair resulted in 85 compounds that satisfy the pharmacophore and dock to the $D_3$ receptor with high scores. One representative compound 4-(2-chlorophenyl)-butan-2-amine (FIGS. 6A-6D) was used for in vitro and in vivo functional characterization. 4-(2-Chlorophenyl)-butan-2-amine docked very similar to the parent PBZI compound in the $D_3$ receptor, making the required salt bridge interaction with Asp110 and hydrophobic aromatic interactions with aromatic residues such as Phe345 and His349 (FIGS. 6A-6D).

Filtering, Chemical Space Analysis and Clustering Modules:

Filtering Schemes:

Compounds that result from pharmacophore based screening are clustered based on their physicochemical properties, such as shape, log P, volume, TPSA and molecular weight, derived from CHEMAXON program. Lipinski's rule of five is applied as a first filter, and a regression based blood-brain-barrier (BBB) penetration model that may filter out compounds for BBB penetration is the second level of filter (Kortagere et al., 2008, Pharm. Res. 8:1836-45). The BBB regression model is a generalized model, described as:

$$\log BB(pred) = 0.3408 * \log P - 0.0192 * TPSA + 0.2503 * a\_nN + 0.1467 * a\_nO + 0.1069 * \log S - 0.0011 * mass - 0.0001 * volume 0.0602 * \#rot. bonds.$$

where: a_nN is number for nitrogen atoms, a_nO is number of oxygen atoms, TPSA is topological polar surface area, log S is solubility and log P is a water/octanol partition coefficient and measure of hydrophobicity, and #rot. bonds is the number of rotatable bonds.

Chemical Space Analysis and Clustering Techniques:

Chemical space analysis of the compounds is performed to analyze if the compounds belong to one or more chemical classes. Outliers that are chemically divergent against the query structure are removed; however a broad cutoff is used to allow for scaffold hoping. Clustering and QSAR based classification of the compounds is performed using support vector machine (SVM) techniques. Methods and application of the SVM based models to classify compounds that may penetrate BBB and to classify PXR activators have been done with good accuracy.

Hence adopting this method to classify the compounds based on the target and to generate an enrichment of the database is useful to avoid screening undesired molecules. The molecules in the database developed herein do not contain stereoisomers. During the enrichment process, compounds that are chemically identical are removed for redundancy by retaining only a single copy of the molecule.

Develop Customized Scoring Schemes:

The GOLD program is used for preliminary docking. The active site for established ligands is defined as all residues that may encompass the ligand within an 8 Å radius sphere. The "library screening mode" option in GOLD docking program is used for fast docking. Further, given the non-deterministic nature of genetic algorithms, 50 independent docking runs are performed for each ligand. The full set of docked structures is energy minimized using the molecular modeling package SYBYL (Tripos Inc., St Louis, Mo., USA). The docked receptor-ligand complexes is scored using a customizable knowledge based scoring function based on the nature of interaction of every ligand atom with the protein atom. Details of the method and the normalization scheme have been discussed in Kortagere et al. (Pharm. Res. 2009, 4:1001-11) Further, a consensus scoring scheme that involves the Goldscore, Chemscore, contact score and shape weighted scoring scheme is used to rank the compounds. A recent application on classifying PXR compounds using the consensus scheme has been detailed in Kortagere et al. Similar schemes are implemented to derive the best ranking compounds that bind to $D_3$ receptor. The docking program used provides some level receptor flexibility at the binding site. However, a complete induced fit model cannot be achieved using this level of screening as it is computationally expensive and may not well be required. As an alternative, another docking program called Glide, that has been well demonstrated to use induce fit concept on the final 25 best docked molecules instead of at the screening level, may be used. This ensures that (a) the best docked complexes are redocked and rescored; and (b) since no one docking or scoring program may efficiently capture the intricacies of the docking process, by using more than one docking program, it is ensured that the best ranked molecules that are short listed for experimental validation are screened efficiently.

Furthermore, to assess the selectivity of these best ranking compounds to the dopamine $D_3$ receptor, they are docked and scored against the other four dopamine receptors. Only those compounds that score the best against the dopamine $D_3$ receptor are used as lead molecules in the iterative HSB method. Preliminary results have validated the HSB protocol, as a novel compound, 4-(2-chlorophenyl)-butan-2-amine (FIGS. 7A-7B), was identified as a $D_3$ receptor agonist that does NOT elicit the tolerance and SRT properties.

Figure 8:
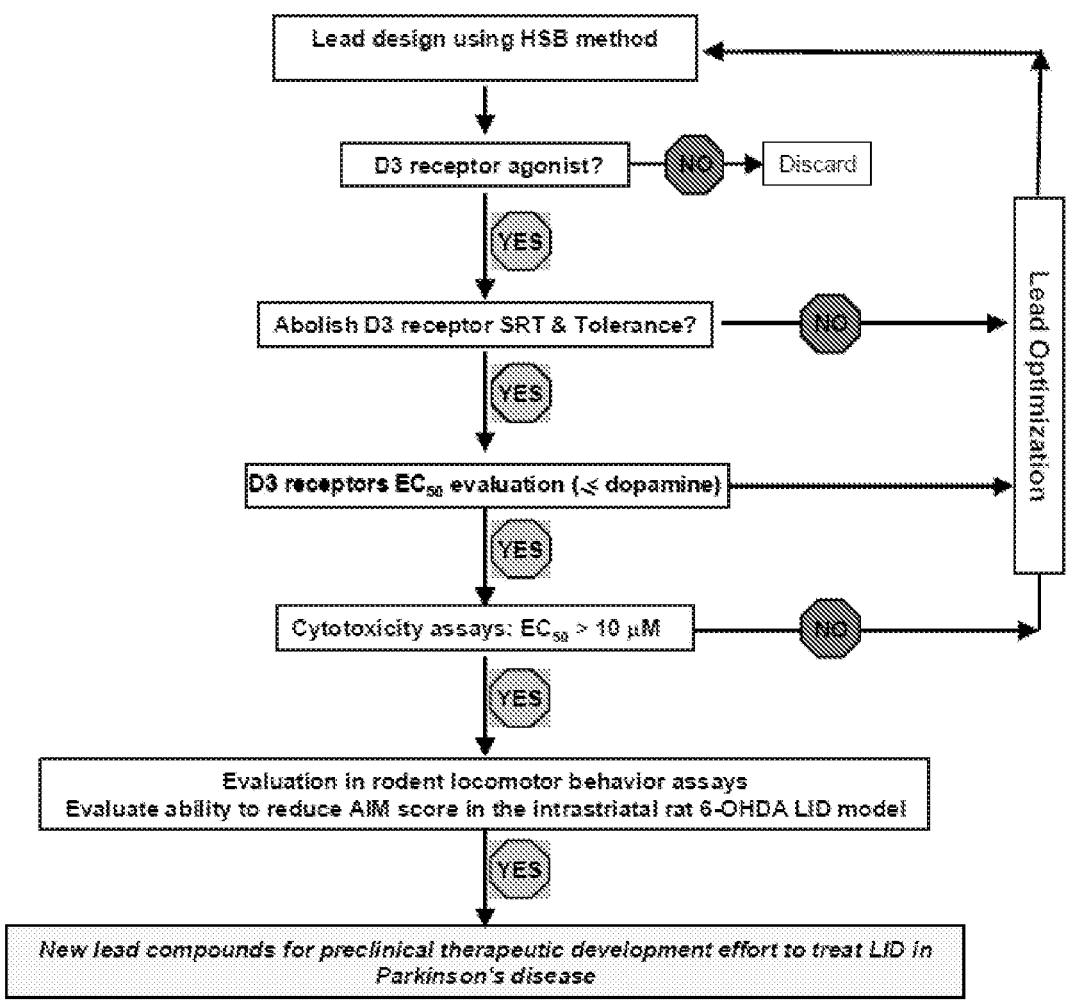
FIG. 8 illustrates a flowchart for the experimental development plan.

Evaluation of the Function, Selectivity and Cytotoxicity Profile of Novel $D_3$ Receptor Agonists in Cell-Based Assays The lead compounds identified above are evaluated in cell based assays to determine their ability to activate $D_3$ receptors without inducing tolerance and SRT properties. The selectivity at various dopamine receptor subtypes are assessed by generating functional dose-response curves from AtT-20 neuroendocrine cell lines stably expressing the various dopamine receptor subtypes. The cytotoxicity is assessed by measuring the effect of lead compounds on proliferation and cell death of three different cell lines representing an endocrine, neuronal and hepatic cell type. Each criterion that determines if a lead compound progresses through the preclinical development protocol is shown in FIG. 8.

Agonism of $D_3$ Dopamine Receptor:

To determine whether a compound is an agonist of the $D_3$ dopamine receptor the AtT-20 neuroendocrine cell line that stably expresses the human $D_3$ receptors is used. In the initial screen, the ability of 300 nM lead compound to activate G-protein coupled inward rectifier potassium (GIRK) channels (FIGS. 1A-1D) is measured using whole cell voltage clamp recording. The protocol has been previously used for performing whole cell voltage clamp and measuring agonist-induced GIRK response. The acute ligand-induced GIRK currents are compared to that elicited by equivalent concentration of native agonist dopamine or full agonist quinpirole. The specificity of the response is determined by measuring GIRK response elicited by the lead compound in non-transfected AtT-20 cells and also in the presence of $D_2$-like dopamine receptor antagonist eticlopride and $D_3$ receptor selective antagonist GR218231 ((+)-(2R)-1,2,3,4-tetrahydro-6-[[(4-methoxyphenyl)sulfonyl]methyl]-N,N-dipropyl-2-naphthalenamine). To be considered for further development, the lead compound should generate a GIRK response that is equal to or greater than that elicited by equivalent concentration (300 nM) of dopamine or quinpirole.

Abolishment of the $D_3$ Receptor Tolerance and SRT

Figure 9A:
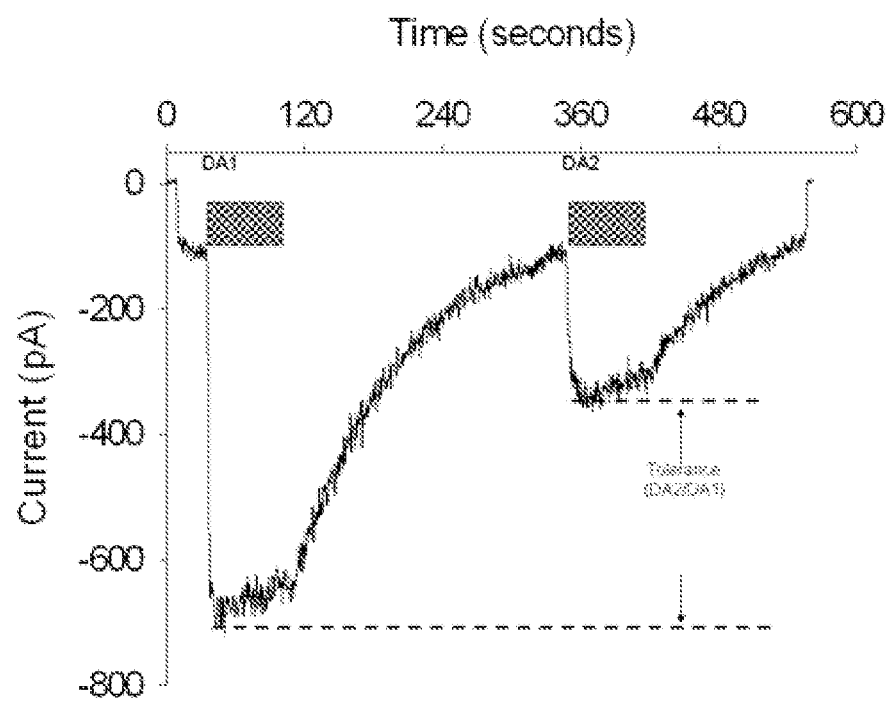
FIGS. 9A-9C illustrate voltage clamp experiments.
Figure 9B:
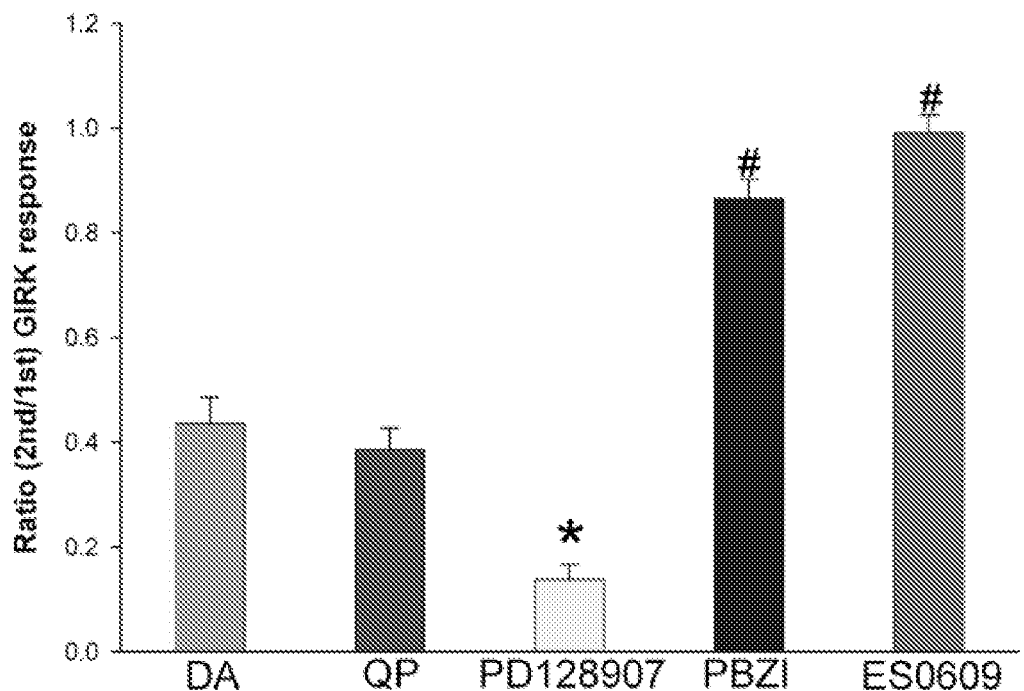
Figure 9C:
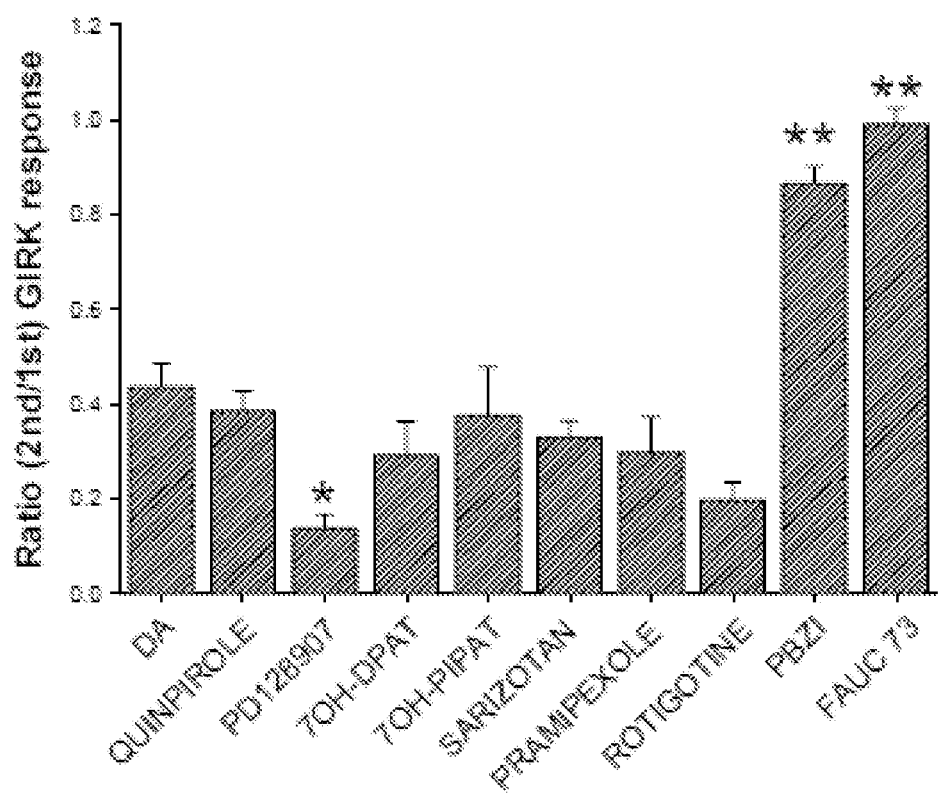

To determine whether a compound abolishes the $D_3$ receptor tolerance and SRT, the $D_3$ receptor-activated GIRK response to two consecutive treatments of the lead compound is measured. As illustrated by FIGS. 9A-9C, the ratio of the second response to first response is close to 1 for agonists that abolish tolerance but is approximately 0.4 for agonists that elicit tolerance (for e.g. dopamine and quinpirole). In one embodiment, for further consideration, the lead compound should have a ratio of second to first GIRK response between 0.7 and 1.0.

Figure 10A:
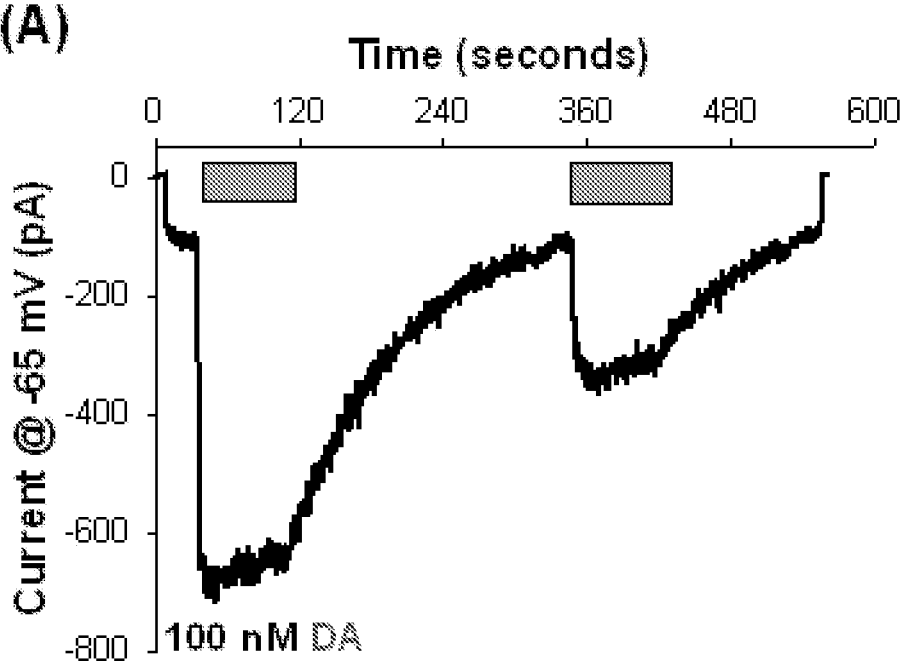
FIGS. 10A-10B illustrate representative voltage clamp recording showing that PBZI (PEUN1) may compete with dopamine (DA) and prevent the development of tolerance and SRT at $D_3$ receptors expressed stably in AtT-20 cells.
Figure 10B:
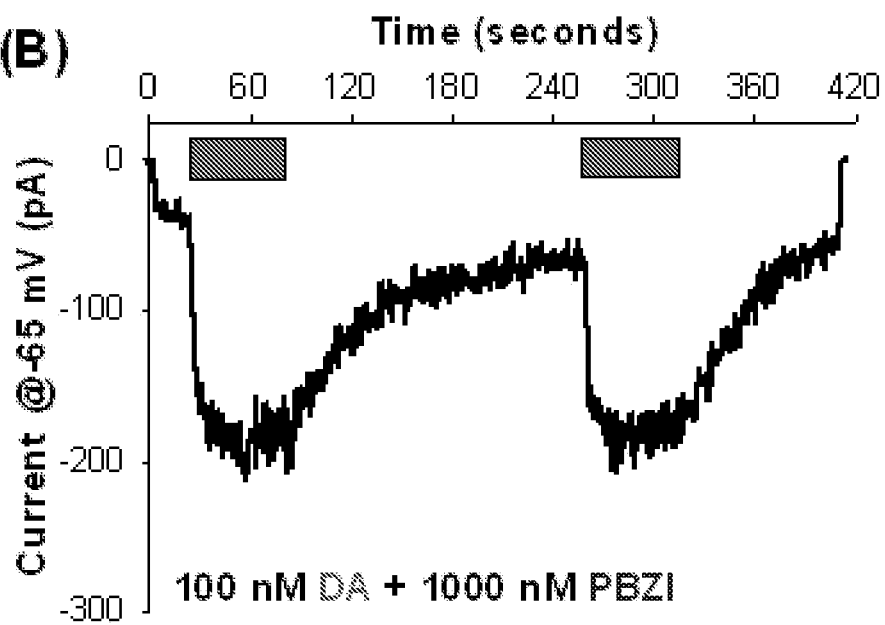

In a second series of experiments, using the coupling to GIRK channels as the assay, the ability of the lead compound to compete with 100 nM, 300 nM and 1000 nM dopamine to block the development of tolerance and SRT at $D_3$ receptors is determined. As illustrated in FIGS. 10A-10B, PBZI (which reduces AIM scores in the LID model) was able to compete effectively with dopamine in this assay.

Determination of the $EC_{50}$ of Lead Compound at Various $D_2$-like Dopamine Receptors:

AtT-20 neuroendocrine cell lines stably expressing the human isoforms of $D_{2S}$, $D_{2L}$, $D_3$, $D_{4.2}$ and $D_{4.4}$ dopamine receptors are available. In addition, AtT-20 cells stably expressing $D_1$ dopamine receptors and 5HT-1A serotonin receptors are also available. Furthermore, non-transfected AtT-20 cells express endogenous somatostatin and muscarinic receptors.

As the initial step, membranes isolated from the cell lines stably expressing the various dopamine receptors are used to perform competitive radioligand binding assays. This procedure yields the $K_i$ of the lead compound for the various dopamine receptor subtypes. As the next step, the various cell lines are used to obtain dose response curves in two functional assays.

In the first assay, whole cell voltage clamp recording is used to measure GIRK response to increasing concentrations of the lead compound (0.01 nM to 3,000 nM dose range). The $EC_{50}$ values for each receptor subtype is determined by fitting the data points using the Hill equation.

Figure 11A:
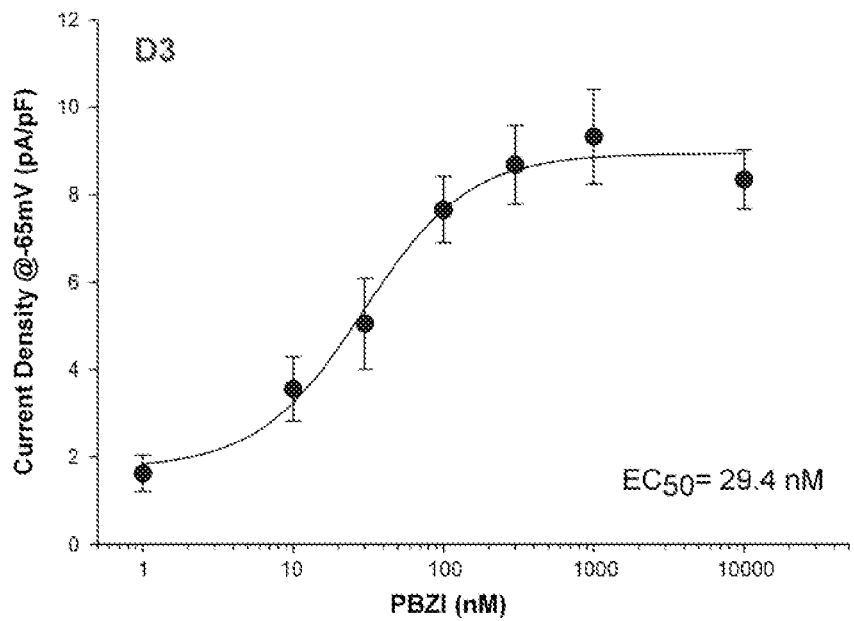
FIGS. 11A-11B illustrate dose response curves for PBZI (FIG. 11A) and 4-(2-chlorophenyl)-butan-2-amine (ES609.
Figure 11B:
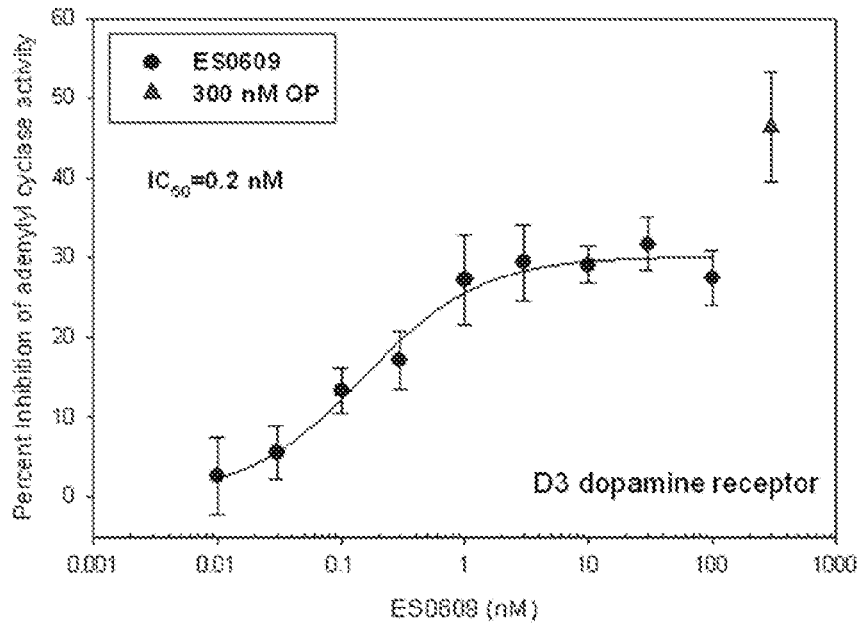

In the second functional assay, the ability of $D_2$-like dopamine receptors to inhibit adenylyl cyclase activity is assessed. The ability of the lead compound to dose-dependently decrease forskolin-induced cAMP levels is measured. The $IC_{50}$ values for each receptor subtype is determined by fitting the data points using the Hill equation. Previously, the $EC_{50}$ and $IC_{50}$ values for dopamine and quinpirole has been determined in these cell lines in both functional assays. In one embodiment, to be advanced, the lead compound has to have an $EC_{50}$ or $IC_{50}$ value that is less than or equal to that of dopamine or quinpirole in either one of these assays. FIGS. 11A-11B illustrates examples of dose response curves for PBZI and 4-(2-chlorophenyl)-butan-2-amine at $D_3$ dopamine receptor.

Assessment of Cytotoxicity of the Lead Compound:

To determine the cytotoxicity of the lead compound, the cell proliferation labeling reagent WST-1 (2-(4-iodophenyl)-3-(4-nitrophenyl)-5-(2,4-disulfophenyl)-2H-tetrazolium, monosodium salt; Roche Applied Science) is used. The effect of the lead compound on the proliferation of three different cell lines (AtT-20 cells as a model for neuroendocrine cells, CAD cells as a model for catecholaminergic neuronal cells and HepG2 as a model for hepatic cells) is determined. Together, the three cell lines provide a preliminary screen for cytotoxicity.

The cells are treated with a wide concentration range of the lead compound (0.01 nM to 100 μM) for 24 hours and then incubated with WST-1 for an additional 4 hours and the absorbance values are determined using a spectrophotometer. The criterion for being selected in the cytotoxicity screen is that the lead compound should exhibit an $EC_{50}$ greater than 10 μM. As the lead compound development advances, the compound is also submitted to in vivo ADMET, toxicity and pharmacokinetic analysis.

Assessment of the Effect of Novel $D_3$ Receptor Agonists in Locomotor Behavior Assays The compounds useful within the invention are evaluated for their ability to reduce AIMs scores in the rat intrastriatal 6-OHDA lesion model of LID.

Assessment of the Effect of the Lead Compound on Locomotor Activity in Balb/c Mice:

Tolerance- and non-tolerance inducing agonists that target dopamine $D_3$ receptors differentially alter locomotor activity. Specifically, tolerance-inducing compounds (e.g., PD128907, also known as (4aR,10bR)-3,4a,4,10b-tetrahydro-4-propyl-2H,5H-[1]benzopyrano-[4,3-b]-1,4-oxazin-9-ol hydrochloride; quinpirole; and PBZI) induce biphasic locomotor effects, characterized by an initial inhibition and a subsequent stimulation of locomotion.

Figure 12A:
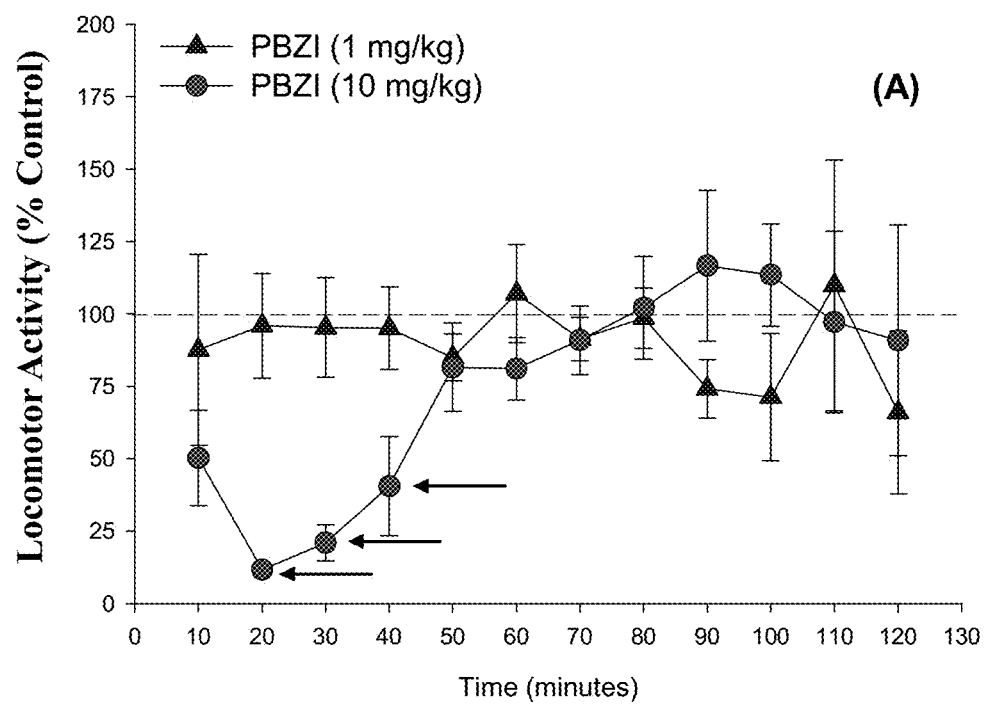
FIGS. 12A-12B illustrate the effects of PBZI and PD128907 on locomotion in Balb/c mice.
Figure 12B:
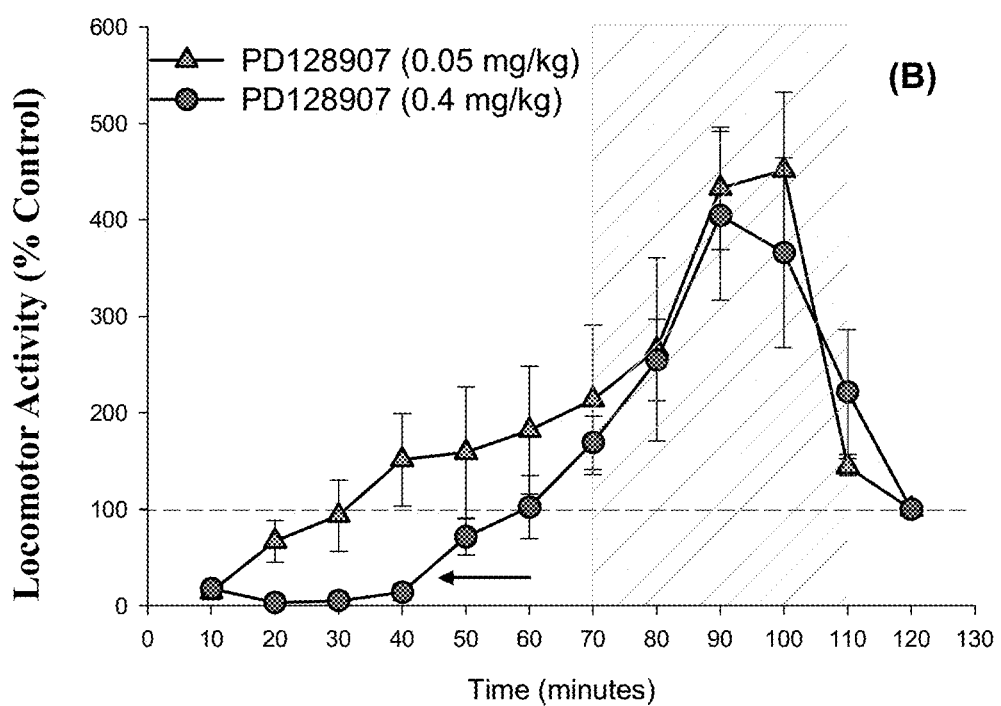

The preliminary results (Example 5) are consistent with studies that have demonstrated that administration of classical $D_2/D_3$ receptor agonists such as quinpirole, PD128907 or 7-hydroxy-N,N-dipropyl-2-aminotetralin (7OH-DPAT) elicited a biphasic locomotor response characterized by an initial inhibition and a subsequent stimulation of locomotion. The studies reported herein indicate that administration of $D_3$ receptor agonists such as PBZI that abolish tolerance and SRT to Balb/c mice only elicit hypoactivity. In contrast, PD128907 elicited tolerance and SRT at $D_3$ dopamine receptors and induces both hypoactivity and hyperactivity (FIGS. 12A-12B). Since PBZI significantly reduced the AIM score in the rat LID model (FIGS. 13A-13B), the agonist-induced locomotor activity assay may be used as a predictor of compounds that successfully reduce dyskinesia in the LID model.

In one embodiment, a goal of the study is to test this hypothesis as it may lead to development of a simple behavioral assay for screening lead compounds that might be beneficial for treating LID. Therefore, three different doses of the lead compound are administered and their effects on locomotor activity are determined. The dosage is determined based on the functional $EC_{50}$ values and binding affinity of the lead compound from the cell-based assays described above. The compound is administered to Balb/c mice and locomotor activity is monitored using the TruScan Automated Behavioral Monitoring system (Coulborn Instruments). In a non-limiting aspect, the lead compound that abolishes $D_3$ receptor tolerance and SRT only elicits hypoactivity in the locomotor assay, consistent with the PBZI results (FIGS. 12A-12B).

Assessment of the Effect of the Lead Compound in the Rat Intrastriatal 6-OHDA Lesion Model:

If the tolerance and SRT properties of the $D_3$ receptor contributes to the expression of LID in the intrastriatal 6-hydroxydopamine (6-OHDA) lesioned rats, administration of non-tolerance-inducing $D_3$ receptor agonists, such as PBZI, prior to levodopa administration should reduce or abolish the symptoms associated with dyskinesia.

The unilateral intrastriatal 6-OHDA lesioned rat model of Parkinson's Disease has been extensively characterized and widely used to test neuroprotective and transplantation strategies to treat Parkinson's Disease. The partial and slowly progressing degeneration of the nigral dopamine neurons and the concomitant development of motor deficits in this rat Parkinson's Disease model appear to mimic the progressive deterioration observed in patients suffering from Parkinson's Disease. Of particular interest is the development of LID in this animal model, which are similar to the abnormal involuntary movements (AIMs) seen clinically.

The intrastriatal 6-OHDA rat Parkinson's Disease model described by Winkler et al., 2002 is herein used. In particular, rats in which unilateral intrastriatal lesion is induced by injection of 6-OHDA (7 μg) at three different sites in the ventrolateral striatum are used. The coordinates for the three injection sites are, in mm: injection site 1: AP: +1.0; ML: −3.0; DV: −5.0; injection site 2: AP: −0.1; ML: −3.7; DV: −5.0; injection site 3: AP: −1.2; ML: −4.5; DV: −5.0. Anterior-posterior (AP) and mediolateral (ML) coordinates are from bregma. The dorso-ventral (DV) coordinates are from dura. The toothbar location is 0.

Figure 14:
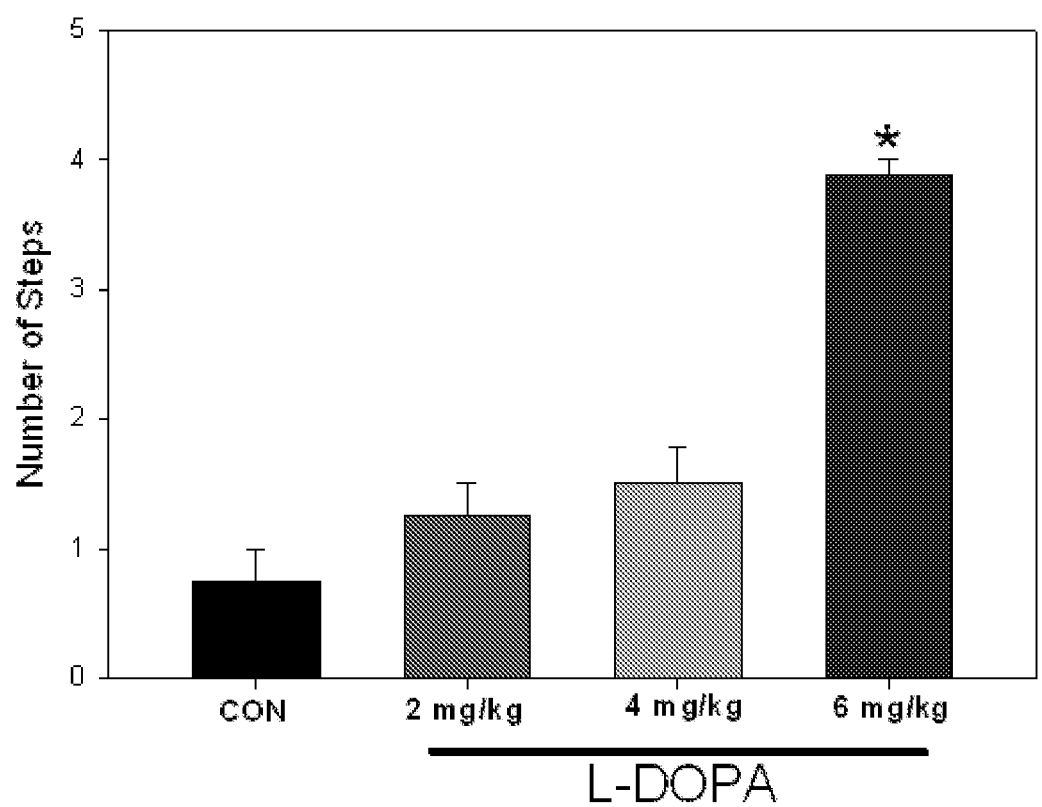
FIG. 14 is a bar graph illustrating the dose dependent improvement in forelimb bradykinesia following levodopa (L-DOPA) injection, measured using the forelimb stepping test. (*, P<0.01, ANOVA, post hoc Holm's test).

The intrastriatal 6-OHDA lesioned and sham lesioned rats are obtained from the Custom Surgical Services division of Charles River Laboratories, Wilmington, Mass., USA. The commercial vendor tests the lesioned animals for amphetamine-induced rotation one week post lesion prior to shipping. A previous study has demonstrated that animals lesioned by the three-site injection exhibit a significant increase in amphetamine-induced rotation after one week. The lesioned animals exhibit bradykinesia/akinesia in the limb contralateral to the lesion. In the experiments, the ability of levodopa to improve bradykinesia/akinesia in the contralateral paw is first determined by performing the forelimb stepping test. The stepping test, subsequently, also provides a way to test if the lead compound interferes with the ability of levodopa to improve bradykinesia/akinesia. The effect of lesion on forelimb bradykinesia/akinesia is measured three weeks post-lesion using the stepping test. Once a significant deficit in stepping ability is established in the paw contralateral to the lesion, increasing doses of levodopa (2, 4 and 6 mg/kg) are administered along with 15 mg/kg benserazide (peripheral DOPA-decarboxylase inhibitor) and stepping ability assessed using the Stepping test, 60 minutes post injection. The dose of levodopa that is selected for the chronic administration phase is the dose that significantly improves the score in the stepping test (FIG. 14).

Seven and half weeks after the lesion, chronic levodopa treatment (6 mg/kg, single dose per day given with 15 mg/kg benserazide) is initiated. Stepping test and AIMs scores are determined on day 1, 8, 10, 17 and 24 after the initiation of chronic levodopa treatment. Upon chronic levodopa administration, the lesioned animals exhibit abnormal involuntary movements (AIMs) that include locomotor, axial, limb, and orolingual components. AIMs are scored using a rating scale based on frequency and severity of the dyskinetic symptoms. It should be noted that the rank order of the various AIMs components in terms of frequency and severity in the rat model is: limb>orolingual=axial>>locomotor. This lesion model has been used to test the effect of PBZI on LID (Example 3).

To determine AIMs score, the rats are placed in a transparent glass cylinder and recorded using a digital video recorder. An experimentally blinded scorer observe for one minute at every $20^{th}$ minute, from 20 minutes before to 180 minutes after the injection of levodopa. Levodopa-induced AIMs score is determined according to the rat dyskinesia scale. 6-OHDA lesioned animals develop LID approximately 10 days after initiation of the chronic levodopa treatment. The ability of PBZI to reduce the levodopa-induced AIMs score was determined by administering PBZI 10 minutes prior to levodopa administration on day 10, 17 and 24 after initiation of the chronic levodopa administration. The stepping test was also performed on these days to assess the effect of PBZI on the ability of levodopa to improve the stepping deficit in the lesioned animals. Two doses of the lead compound are tested. The dosage is determined by the affinity of the compound for the receptor and the results of the locomotor behavior assay described above.

Figure 15:
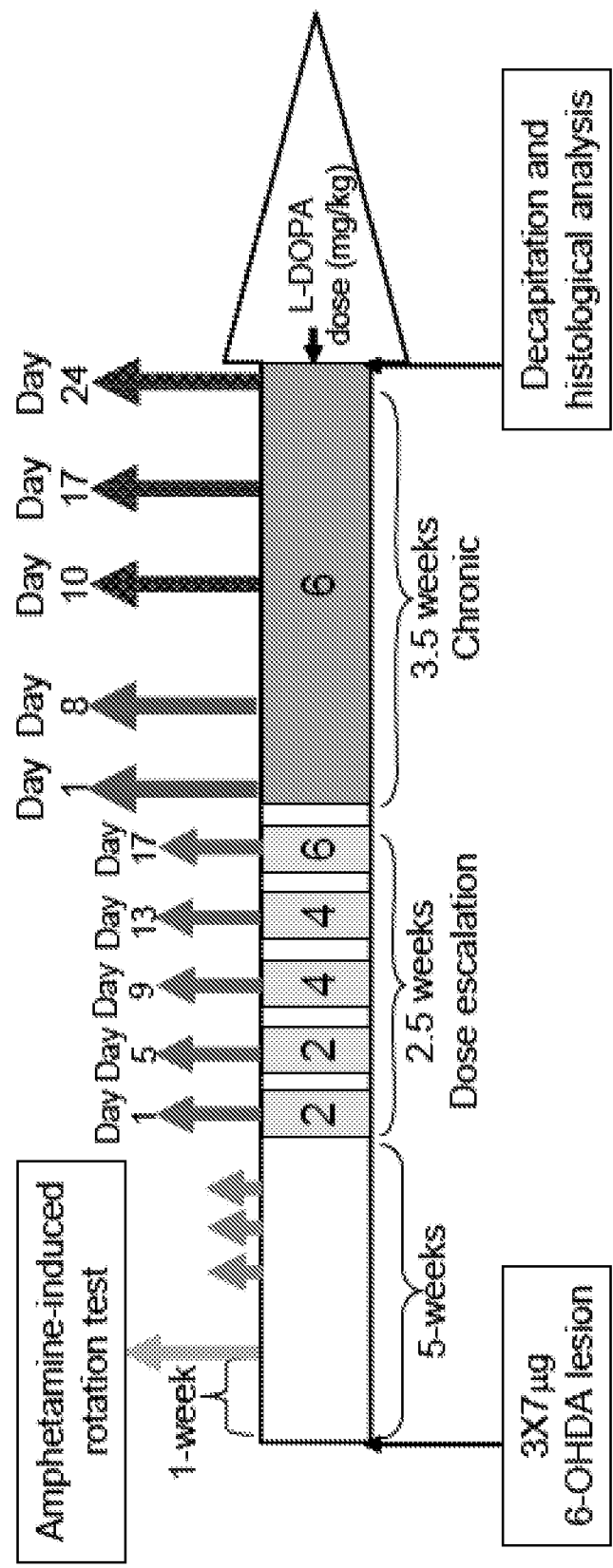
FIG. 15 illustrates the time course of the in vivo experiments.

The time course of the experiment is shown in FIG. 15. One week after the 3-site unilateral intrastriatal 6-OHDA injection, the rats are subjected to the amphetamine-induced rotation test to identify lesioned animals. Three weeks post lesion, the animals are subjected to the stepping test to determine the pre-levodopa stepping deficit. Five weeks post lesion, increasing doses (2 to 6 mg/kg) of levodopa are administered once daily only on indicated days and stepping test performed. Seven and half weeks post lesion, levodopa (6 mg/kg) is administered once daily every day for 3.5 weeks. On day 1 and 8 after initiation of the chronic administration, stepping test and AIMs scores are determined following levodopa injection. On days 10, 17 and 24 stepping test and AIMs scores are determined following co-injection of levodopa and compound. At the end of 11-weeks, the animals are decapitated and brain tissue used for histological analysis: brain sections of animals are stained for tyrosine hydroxylase to assess loss of dopaminergic neurons in the lesioned hemisphere. Brain sections from some animals are assessed for $D_2$ and $D_3$ receptor binding and mRNA expression.

Combination Therapies

The compounds of the present invention are intended to be useful in the methods of present invention in combination with one or more additional compounds useful for treating Parkinson's Disease. These additional compounds may comprise compounds of the present invention or compounds, e.g., commercially available compounds, known to treat, prevent, or reduce the symptoms of Parkinson's Disease.

In non-limiting examples, the compounds of the invention may be used in combination with one or more of the following drugs: levodopa, clozapine, bromocriptine, pergolide, pramipexole, ropinirole, piribedil, cabergoline, apomorphine, and lisuride, a salt thereof and mixtures thereof.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the patient either prior to or after the onset of a LID. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat LID in the patient. An effective amount of the therapeutic compound necessary to achieve a therapeutic effect may vary according to factors such as the state of the disease or disorder in the patient; the age, sex, and weight of the patient; and the ability of the therapeutic compound to treat LID in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of LID in a patient.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin. In one embodiment, the pharmaceutically acceptable carrier is not DMSO alone.

In one embodiment, the compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It will be readily apparent to one skilled in the art that the frequency of administration of the various combination compositions of the invention will vary from individual to individual depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating Parkinson's Disease) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of LID in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a LID in a patient.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds of the invention, and a further layer providing for the immediate release of a medication for treatment of Parkinson's Disease. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In a preferred embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention will depend on the age, sex and weight of the patient, the current medical condition of the patient and the progression of Parkinson's Disease in the patient being treated. The skilled artisan will be able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials:

Unless otherwise noted, all starting materials and resins were obtained from commercial suppliers and used without purification.

Quinpirole (Sigma-Aldrich, St. Louis, Mo.), PD128907 (Tocris, Ellisville, Mo.), 7OH-DPAT (Tocris), pramipexole (Tocris), rotigotine (Tocris), 4-(2-chlorophenyl)-butan-2-amine (ES609; Asinex, Moscow, Russia) and cis-8-Hydroxy-3-(n-propyl)-1,2,3a,4,5,9b-hexahydro-1H-benz[e]indole hydrobromide (PBZI; Sigma-Aldrich) were dissolved in water and used at indicated concentrations. Sarizotan (Merck KGaA, Gibbstown, N.J.), FAUC73 (Sigma-Aldrich) and 7OH-PIPAT (Tocris) were dissolved in DMSO. A 10 mM stock of dopamine (Sigma-Aldrich) was freshly dissolved in 100 mM ascorbic acid and used at a final concentration of 100 nM.

Cell Culture:

AtT-20 mouse pituitary cells were grown in Ham's F10 medium with 5% FBS, 10% heat-inactivated horse serum, 2 mM glutamine and 50 μg/ml gentamicin (Invitrogen, Carlsbad, Calif.). AtT-20 cells stabling expressing the human $D_{2S}$, $D_{2L}$, $D_3$, and $D_{4.2}$ and receptor were maintained in the above F10 culture media supplemented with 500 μg/ml G418 (Invitrogen). For electrophysiological characterization, cells were plated onto glass coverslips coated with 40 μg/ml poly L-lysine (Sigma-Aldrich). The generation and characterization of the AtT-20 cells stably expressing various human dopamine receptors have been previously reported (Kuzhikandathil & Oxford, 2000, J. Gen. Physiol. 115:697-706; Kuzhikandathil et al., 1998, Mol. Cell Neurosci. 12:390-402; Kuzhikandathil & Bartoszyk, 2006, Neuropharm. 51:873-884; Westrich & Kuzhikandathil, 2007, Biochim. Biophys. Acta-MCR 1773:1747-1758; Kuzhikandathil et al., 2004, Mol. Cell Neurosci. 26:144-155; Westrich et al., 2010, Biochem. Pharmacol. 79:897-907).

Measurement of cAMP:

Cyclic AMP (cAMP) levels were assessed using the cAMP Biotrak Enzymeimmunoassay (EIA) kit (GE Healthcare, Piscataway, N.J., USA) as described previously (Kuzhikandathil & Bartoszyk, 2006, Neuropharm. 51:873-884). The cAMP levels in each treated sample were assayed in triplicate and the entire experiment repeated three independent times.

Electrophysiology:

Agonist-activated currents were measured by the whole-cell patch clamp technique in voltage clamp and current clamp mode as described previously (Kuzhikandathil & Oxford, 2000, J. Gen. Physiol. 115:697-706; Kuzhikandathil et al., 1998, Mol. Cell Neurosci. 12:390-402; Kuzhikandathil & Bartoszyk, 2006, Neuropharm. 51:873-884; Westrich & Kuzhikandathil, 2007, Biochim. Biophys. Acta-MCR 1773:1747-1758; Kuzhikandathil et al., 2004, Mol. Cell Neurosci. 26:144-155; Westrich et al., 2010, Biochem. Pharmacol. 79:897-907). Drug solutions were delivered to cells via a multi-barreled micropipette array. The current responses were normalized to the cell capacitance, to account for variation in cell size.

Statistics:

Analysis of variance (ANOVA) and the Holm-Sidak multiple pair-wise comparison tests and Student's t-test was performed with the SigmaPlot® 11 software (SPSS Inc.). Data were considered statistically significant when the probability value (P) was less than 0.05.

Computational Modeling (HSB Method):

The HSB protocol for designing small molecule inhibitors to G-protein coupled receptors has been described (Kortagere & Welsh, 2006, J. Compu.t Aided Mo.l Des. 20(12): 789-8026). Briefly, the method involved creating a focused library of small molecules derived from commercial vendors. All molecules in the database were converted to the UNITY format and screened using UNITY module integrated in SYBYL (SYBYL 8.0, Tripos International).

To create a 3D pharmacophore based on the interactions of PBZI in $D_3$ receptor binding site, a homology model of $D_3$ receptor was created using the crystal structure of the beta adrenergic (β2-AR) receptor in complex with a partial inverse agonist (PDB code: 2RH1) (Cherezov et al., 2007, Science 318(5854):1258-1265) as a template with the homology modeling program Modeller (ver 9.4) (Sali et al., 1993, J. Mol. Biol. 234(3):779-815; Westrich et al., 2010, Biochem. Pharmacol. 79:897-907; Kortagere et al., 2011, Biochem. Pharmacol. 81(1):157-163). PBZI has a fairly rigid conformation owing to its tricyclic structure. A conformational analysis using stochastic search method adopted in MOE was utilized to obtain the best conformation of the alkyl tail region extending from the amine group. All the conformations obtained were clustered based on energy and a representative member from the most populated cluster was chosen for further optimization using the AM1 semi-empirical quantum chemical method adopted in MOE. A similar procedure was used for other ligands in this study. The optimized conformations were used for further docking experiments. PBZI was docked to the 3D structure of the refined $D_3$ structure using docking program GOLD (ver 4.1) (Jones et al., 1995, J. Mol. Biol. 245(1):43-53). Twenty independent runs were performed and the docked complexes were scored using Goldscore (Jones et al., 1995, J. Mol. Biol. 245(1):43-53), chemscore (Eldridge et al., 1997, J. Comput. Aided Mol. De.s 11(5):425-445) and customized scoring scheme (Kortagere & Welsh, 2006, J. Comput. Aided Mol. Des. 20(12):789-802).

Figure 6A:
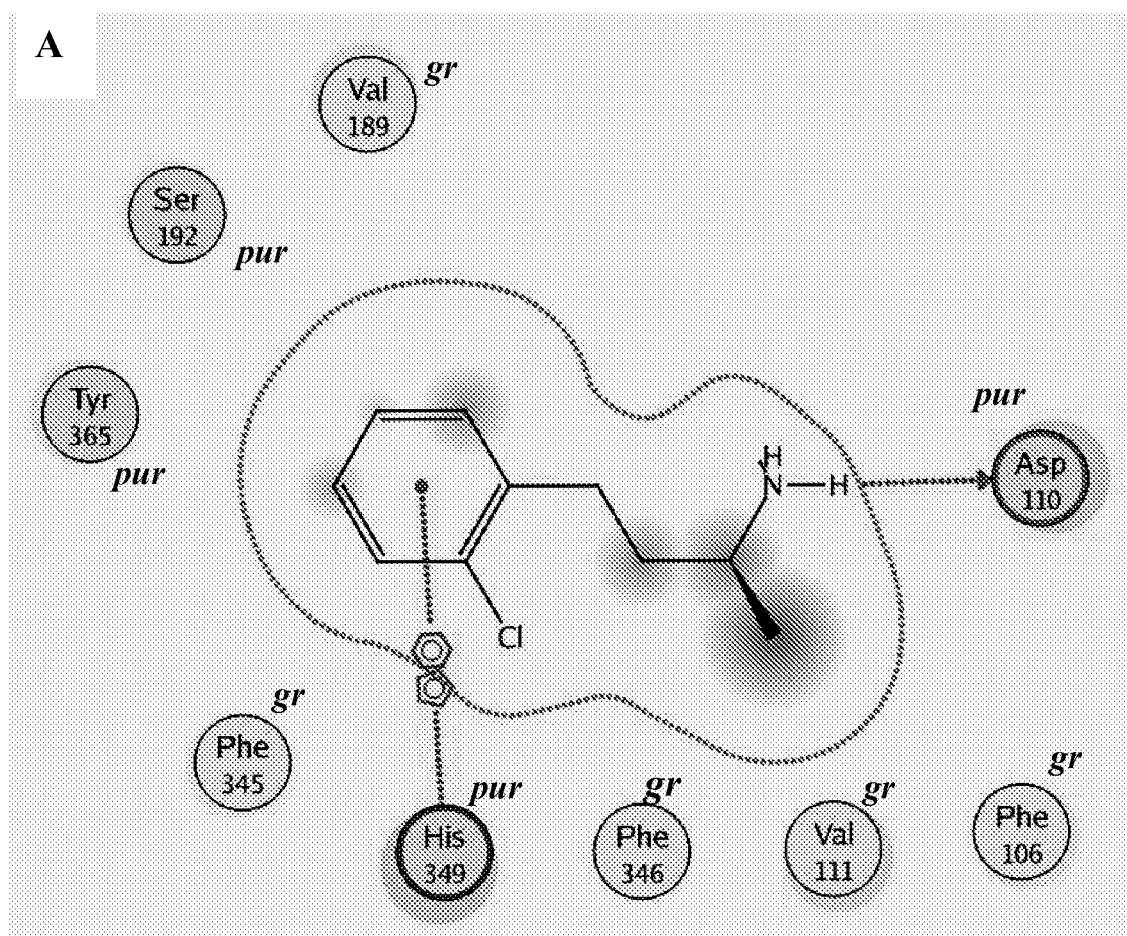
FIGS. 6A-6D are a series of schemes illustrating the mode of interaction of ES609 (FIG. 6A), PD128907 (FIG. 6B), PBZI (FIG. 6C), and Dopamine (FIG. 6D). The binding site residues are colored by their nature, with hydrophobic residues in green (labeled gr), polar residues in purple (labeled pur), and charged residues highlighted with bold contours. Gray spheres and contours indicate matching regions between ligand and receptors. Hydrogen bonded interactions are shown by arrows, ionic interactions in lines and pi-pi interactions in lines extending across the two six membered rings. The figures were generated using the LIGX module of MOE program. The 3D pharmacophore used to screen the molecules is overlaid on the PBZI structure (FIG. 6C) with open red circles representing hydrophilic interactions (labeled red), blue open circles representing hydrophobic and aromatic interactions (labeled b) and black dotted lines representing distance between the pharmacophore elements.
Figure 6B:
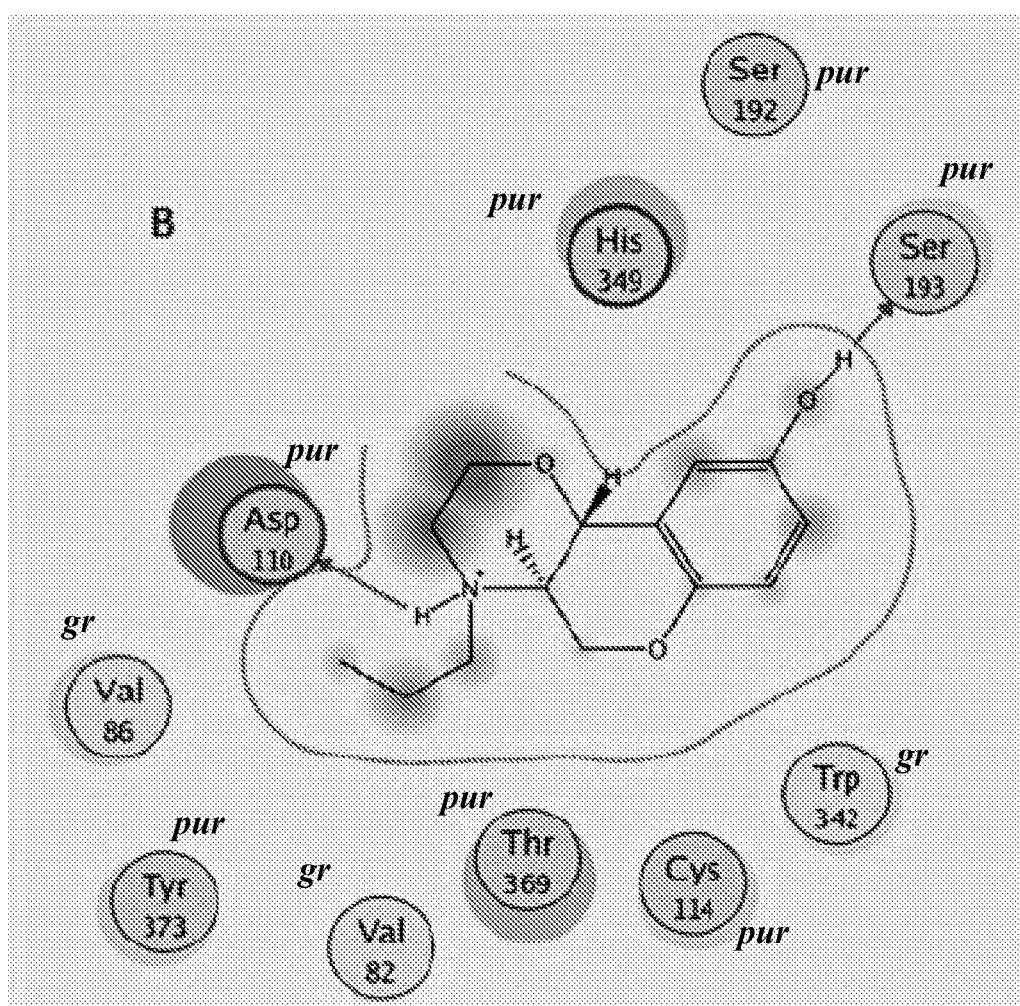
Figure 6C:
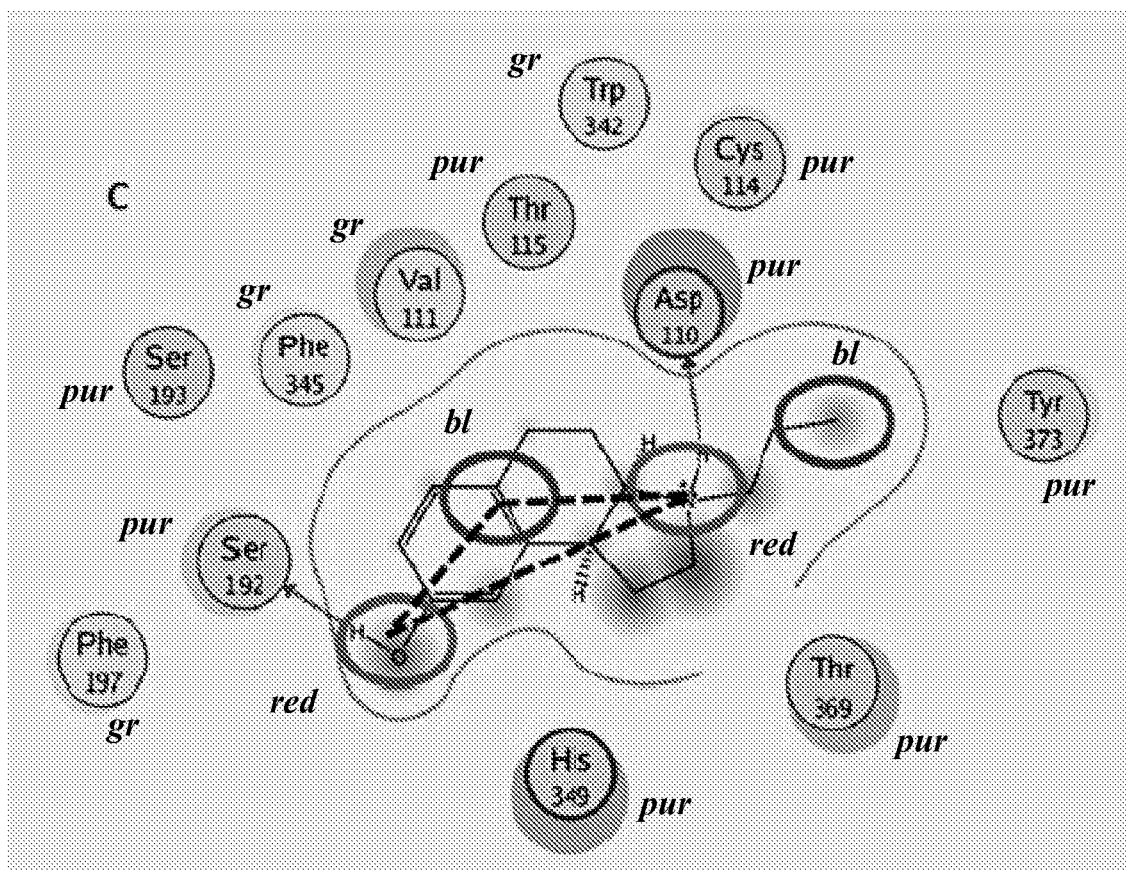

To obtain a more realistic conformation of the agonist bound model, the model was immersed into an explicit water-POPC lipid bilayer-water model membrane system using the Desmond module (Kevin et al., 2006, Proceedings of the ACM/IEEE Conference on Supercomputing (SC06), New York, N.Y., IEEE) of the Schrodinger suite program. The model membrane was pre-aligned to the β2-AR crystal structure to adopt its orientation to the $D_3$ receptor-PBZI model. Default conditions for bilayer composition including those of $Na^+$ and $Cl^-$ ions were selected and the entire simulation was performed using the default all atom OPLS force field. A four step protocol consisting of routines for pre-relaxation, minimization, heating, equilibration and production run of 3 ns was followed to completely refine the model (Chien et al., 2010, Science 330(6007):1091-1115). Throughout the simulations, the interactions of PBZI with residues from TM3 and TM5 were maintained using low levels of constraints. However all constraints were removed during the production run to completely relax the ligand in the protein environment. Key interactions between PBZI and $D_3$ receptor, namely salt bridge with Asp110, hydrogen bonded interaction with Ser192, aromatic ring interactions with His349, hydrophobic interactions with Val111 and other aromatic residues from TM6 were used to build a four point hybrid pharmacophore as shown in FIG. 6C. Electronic libraries of vendor-available small molecules were screened to identify hits that correspond to the pharmacophore.

Finally, the hits were filtered using Lipinski's Rule of 5 (Lipinski et al., 2001, Adv. Drug Deliv. Rev. 46(1-3):3-26), blood brain barrier (BBB) penetration (Kortagere et al., 2008, Pharm. Res. 25(8):1836-1845) and off-target screening against Pregnane xenobiotic receptors (Kortagere et al., 2009, Pharm. Res. 26(4):1001-1011) and hERG channels (Chekmarev et al., 2008, Chem. Res. Toxicol. 21(6):1304-1314). The resulting 290 hits were docked to the binding site of $D_3$ receptor using GOLD program and scored using a variety of scoring functions as described previously for docking of PBZI. Fifteen best ranking hits were obtained from the vendors and functionally evaluated.

Example 1: In Vitro Characterization of Compounds

PBZI and 4-(2-chlorophenyl)-butan-2-amine were characterized for their interactions with dopamine receptors. Both compounds activated G-protein coupled inward rectifier potassium (GIRK) channels via $D_3$ dopamine receptors (FIGS. 2A-2C) and inhibited adenylyl cyclase activity (FIGS. 11A-11B). The in vitro functional data for both compounds are shown in Table 1. Of most interest was the observation that unlike traditional $D_2/D_3$ receptor agonists, PBZI and 4-(2-chlorophenyl)-butan-2-amine abolished the tolerance and SRT properties of the D3R (FIGS. 2A-2C). These two compounds represent a new class of $D_3$ dopamine receptor agonists that abolishes the tolerance and SRT properties of the $D_3$ receptor while being a full agonist.

distinct agonists were screened for their ability to induce tolerance and SRT, using the $D_3$ receptor-GIRK channel signaling pathway as an assay. The selected agonists included the endogenous ligand dopamine, ligands that exhibited selectivity for $D_3$, and compounds used clinically to treat Parkinson's disease. The results in FIG. 9C suggest that, while most agonists induced tolerance, two agonists, cis-8OH-PBZI and FAUC73, abolished the tolerance property. Interestingly, PD128907 induced enhanced tolerance that was significantly different than the other agonists.

FIGS. 2A and 2C illustrate representative voltage clamp recordings of AtT-20 cells stably expressing the human $D_3$ dopamine receptor and treated with agonists that either induce tolerance or do not induce tolerance. PBZI (FIG. 2A) and FAUC73 (FIG. 2C) abolished both tolerance and SRT properties; however in the same cell, quinpirole (FIG. 2A) or PD128907 (FIG. 2C) induced severe tolerance and SRT. Control experiments in parental AtT-20 cells as well as pretreatment with $D_2/D_3$ antagonist, eticlopride (100 nM), showed that the agonistic effect of PBZI and FAUC73 are

TABLE 1

Characterization of PBZI & 4-(2-chlorophenyl)-butan-2-amine effect on $D_2$-like receptor signaling function in AtT-20 stable cell lines)

| PBZI | $D_{2S}$ dopamine receptor | $D_{2L}$ dopamine receptor | $D_3$ dopamine receptor | $D_{4.2}$ dopamine receptor |
|---|---|---|---|---|
| Adenylyl cyclase inhibition | partial agonist ($EC_{50}$ = 140 nM) | full agonist ($EC_{50}$ = 67 nM) | full agonist ($EC_{50}$ = 35 nM) | no response |
| GIRK channel activation | partial agonist ($EC_{50}$ = 53 nM) | full agonist ($EC_{50}$ ND) | full agonist ($EC_{50}$ = 30 nM) | partial agonist ($EC_{50}$ ND) |

| 4-(2-chlorophenyl)-butan-2-amine (ES0609) | $D_{2S}$ dopamine receptor | $D_{2L}$ dopamine receptor | $D_3$ dopamine receptor | $D_{4.2}$ dopamine receptor |
|---|---|---|---|---|
| Adenylyl cyclase inhibition | Partial agonist ($EC_{50}$ = 2.4 nM) | No response | Full agonist ($EC_{50}$ = 0.15 nM) | Partial agonist ($EC_{50}$ = 0.82 nM) |
| GIRK channel activation | Partial agonist ($EC_{50}$ = ND) | Partial agonist ($EC_{50}$ = ND) | Full agonist ($EC_{50}$ = 30 nM) | no response |

ND: not determined

Example 2: Ligand Dependent $D_3$ Receptor Tolerance and SRT Properties

FIG. 9A illustrates the $D_3$ dopamine receptor-induced activation of native GIRK channels when the receptor is stimulated with the endogenous agonist, dopamine. The tolerance property of $D_3$ receptor is quantified as the ratio of $2^{nd}$ to $1^{st}$ agonist-induced response. The $D_3$ receptor tolerance property is also observed in the $D_3$ receptor-adenylyl cyclase and -mitogen activated protein kinase pathways (Kuzhikandathil & Bartoszyk, 2006, Neuropharm. 51:873-884; Westrich & Kuzhikandathil, 2007, Biochim. Biophys. Acta-MCR 1773:1747-1758). In addition, FIG. 9A shows the $D_3$ receptor SRT property, which is the delayed termination of the agonist-induced response after agonist removal. Tolerant $D_3$ receptor adopts a distinct conformation (Westrich et al., 2010, Biochem. Pharmacol. 79:897-907), suggesting that tolerance and SRT properties might be modulated by functionally-selective agonists that alter this distinct conformational state. To identify agonists that might modulate $D_3$ receptor tolerance and SRT properties, ten specific for $D_3$ receptors. Furthermore, the ability to abolish tolerance and SRT was not concentration dependent-PBZI tested at doses from 100 nM to 10 µM did not induce tolerance. Together, these results suggest that the $D_3$ receptor tolerance and SRT properties are ligand-dependent. Of the two tolerance- and SRT-abolishing compounds, PBZI is water soluble and more extensively characterized, in vitro and in vivo.

Example 3: In Vivo Characterization of Compounds: In Vivo Behavioral Response

To determine the in vivo behavioral effect of the novel class of $D_3$ dopamine receptor agonists, the effects of PBZI and a classical tolerance and SRT inducing $D_3$ dopamine receptor agonist, PD128907 ((4aR,10bR)-3,4a,4,10b-tetra-hydro-4-propyl-2H,5H-[1]benzopyrano-[4,3-b]-1,4-oxazin-9-ol hydrochloride), were compared. FIGS. 12A-12B illustrate that PD128907 elicited a biphasic locomotor response in a novel open field activity test. In contrast, PBZI (which does not elicit tolerance and SRT) induced only a monophasic locomotor response. This novel result thus identified a potential behavioral screen for the new class of $D_3$ dopamine receptor agonist described herein.

Example 4: In Vivo Characterization of Compounds: Intrastriatal 6-OHDA Rat Parkinson's Disease Model In order to further evaluate the therapeutic potential of the novel class of $D_3$ receptor agonists, the hypothesis that up regulation of $D_3$ receptor in the striatum contributes to the development of levodopa-induced dyskinesia (LID) in Parkinson's disease was tested. The unilateral intrastriatal 6-OHDA lesioned rat model of Parkinson's Disease has been extensively characterized and widely used to test neuroprotective and transplantation strategies to treat Parkinson's Disease (Winkler et al., 2002, Neurobiol. Dis. 10(2):165-86). The partial and slowly progressing degeneration of the nigral dopamine neurons and the concomitant development of motor deficits in this rat Parkinson's Disease model appeared to mimic the progressive deterioration observed in patients suffering from Parkinson's Disease (Winkler et al., 2002, Neurobiol. Dis. 10(2):165-86). Of particular interest is the development of LID in this animal model, wherein the movements are similar to the abnormal involuntary movements (AIMs) seen clinically.

The intrastriatal 6-OHDA rat Parkinson's Disease model described by Winkler and co-workers was used to test the effect of PBZI and ES0609 on LID (Winkler et al., 2002, Neurobiol. Dis. 10(2):165-86). To determine AIMs score, the rats were placed in transparent glass cylinder and recorded using a digital video recorder. 6-OHDA lesioned animals develop LID approximately 10 days after initiation of the chronic levodopa treatment. The ability of PBZI or 4-(2-chlorophenyl)-butan-2-amine to reduce the levodopa-induced AIMs score was determined by administering the novel $D_3$ receptor agonists 10 minutes prior to levodopa administration on day 10, 17 and 24 after initiation of the chronic levodopa administration. The stepping test was also performed on these days to assess the effect of these new agonists on the ability of levodopa to improve the stepping deficit in the lesioned animals.

Example 5: In Vivo Characterization of Compounds: Reduction of Dyskinesia

Figure 13A:
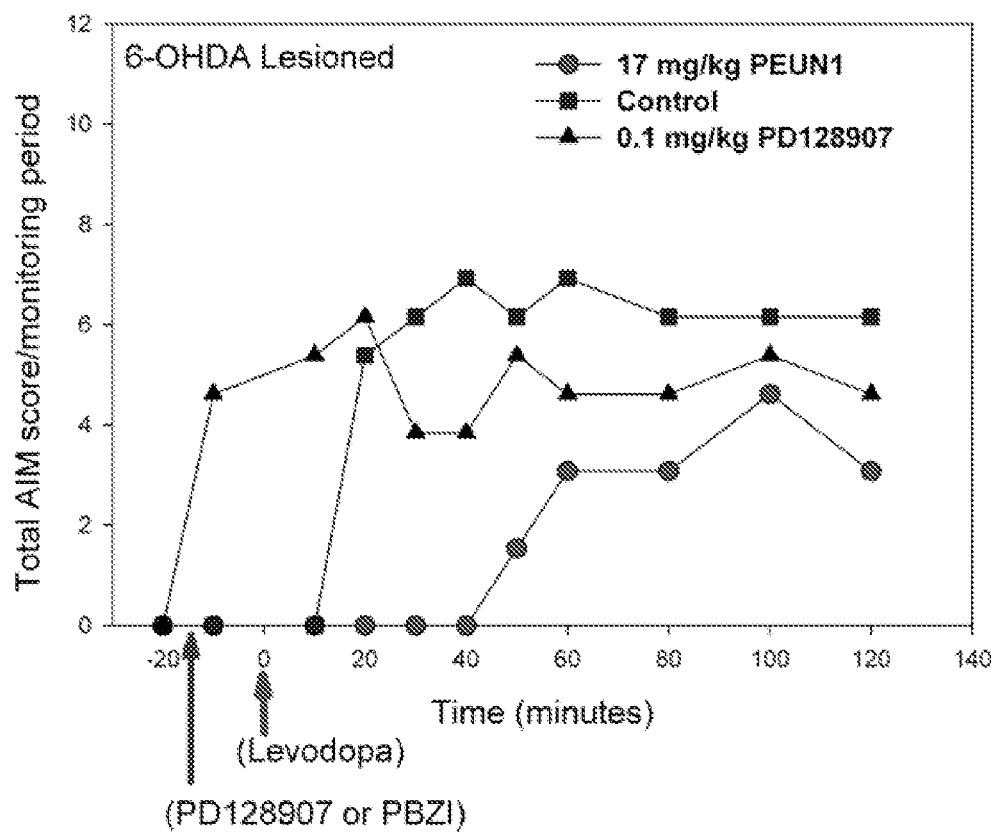
FIGS. 13A-13B illustrate the comparison of PBZI, PD128907 (tolerance-inducing $D_3$ agonist) and control saline on 6 mg/kg levodopa-induced dyskinesia. The drugs were administered 10 minutes prior to levodopa injection. PD128907 increased AIMs score even before the levodopa was administered. PBZI delayed and reduced the dyskinesia induced by levodopa (FIG. 13A).

The ability of a tolerance inducing (PD128907) and the non-tolerance inducing $D_3$ receptor agonists (PBZI or 4-(2-chlorophenyl)-butan-2-amine) to reduce dyskinesia associated with chronic levodopa treatment was tested in the rat model. Control (saline), PD128907 (0.1 mg/kg, sc), PBZI (17 mg/kg, sc) or 4-(2-chlorophenyl)-butan-2-amine (20 mg/kg) were administered ten minutes before levodopa treatment. FIG. 13A illustrates the effect of control, PD128907 (a tolerance inducing $D_2/D_3$ agonist) and PBZI (a non tolerance inducing $D_3/D_3$ agonist) on the total AIMs score (includes locomotor, axial, limb and orolingual) over time of a day 17 (chronic L-DOPA phase) lesioned animal. Interestingly, the administration of PD128907 to the lesioned animals in of itself induced dyskinesia, even before levodopa administration. This is consistent with clinical reports that LID may also be elicited by dopamine receptor agonists used in the treatment of Parkinson's Disease.

Figure 13B:
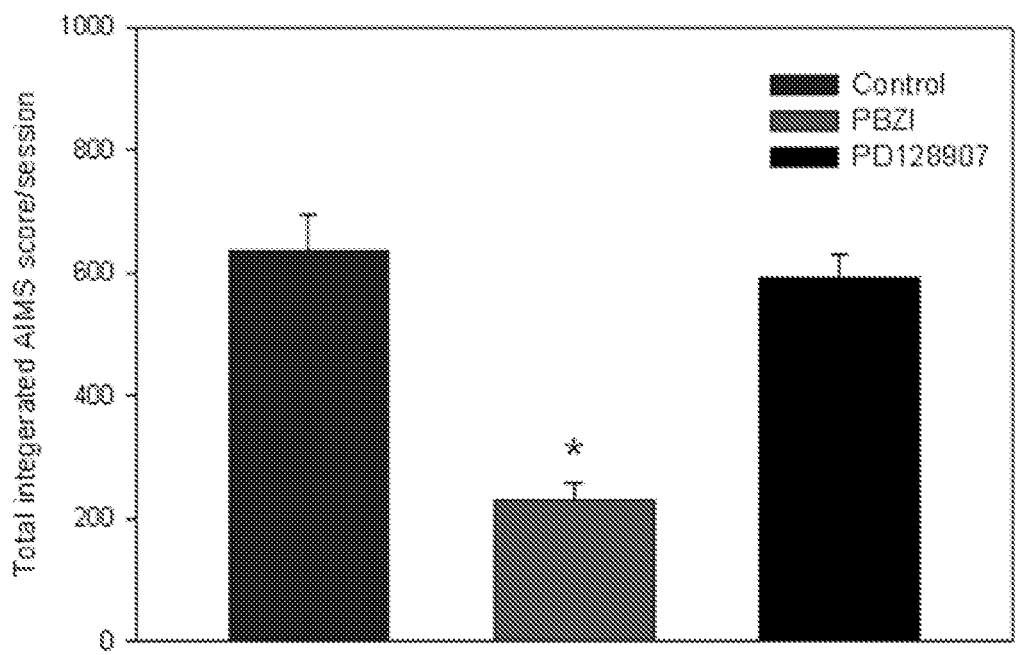

The results in FIG. 13A suggest that PBZI itself did not induce dyskinesia, and delayed the onset of levodopa induced dyskinesia. The cumulative data obtained by calculating the area under the curve in FIG. 13B illustrates that PBZI significantly reduces (by ~300%) the total integrated AIMs score. Stepping test data obtained during co-administration of PBZI and levodopa suggest that PBZI did not attenuate the beneficial effect of levodopa on bradykinesia/akinesia. These results suggest that PBZI and its analogs are promising candidates for preclinical development as new therapeutics for the treatment of LID in Parkinson's disease.

Example 6: In Vivo Characterization of Compounds: Locomotor Behavior in Mice

The effects of PBZI on locomotor behavior in Balb/c mice were evaluated. The specific objectives of this experiment were: (a) to determine whether PBZI would induce a decrease in locomotion in Balb/c mice; (b) to evaluate PBZI's effects over a longer test session; and (c) to determine if PD128907 elicited a biphasic locomotor effect in Balb/c mice.

A total of 12 young adult, male Balb/c mice were obtained form Charles River, Inc. (Wilmington, Mass.), and housed in groups of four in standard cages. The animals were maintained on a 12 hour light/12 hour dark cycle and permitted ad lib access to food and water. Experiments were conducted during the animal's light phase. The strain of mouse was selected based on the previous work evaluating the relationship between dopaminergic compounds and motor activity in Balb/c mice. The mice received a single injection of PBZI (0, 1, or 10 mg/kg, sc), and immediately thereafter were individually placed into a test arena (TruScan arena, Coulbourn Instruments Inc.) for 2-hr in normal illumination. For PD128907, separate groups of Balb/c mice received subcutaneous injections of saline (n=4) or 0.05 or 0.4 mg/kg PD128907 (n=4, for each). Locomotion ('distance traveled') scores of drug-injected animals were collapsed across 10-min intervals and for comparison purposes were normalized to saline injected animals (FIG. 12A). The experiment was conducted on three separate occasions. Locomotion varied significantly as a function of a Dose X Time interaction (F (2,4)=5.40, p=0.002). Newman-Keuls multiple ($\alpha$=0.05) of the main effects comprising this interaction revealed that locomotion was significantly reduced (by approximately 90%) within 20-min in mice receiving 10 mg/kg of PBZI compared with mice in the other groups. Of further importance, there were no between-group differences during the other time intervals. This effect persisted for 40-min post-injection in Balb/c mice.

On the contrary, PD128907, as reported previously for other strains of mice, elicited a biphasic effect in Balb/c mice. A hypoactivity was observed in the first 40-min post-injection followed by hyperactivity during the 70 to 110 minute post-injection period (FIG. 12B). The biphasic effect of PD128907 was observed at a dose of 0.05 mg/kg or higher. While the lower dose of PD128907 (0.05 mg/kg) elicited hypoactivity of a shorter duration (20 minutes), it elicited the same duration and magnitude of hyperactivity. The difference in dose required to elicit hypoactivity is likely due to the differences in $D_3$ dopamine receptor binding affinity for PBZI (K=22 nM) and PD128907 (K=2.3 nM). With both PBZI and PD128907, the locomotor activity returned to control saline levels by 120 minutes post-injection. These results clearly demonstrate that agonists that induce $D_3$ receptor tolerance (PD128907) elicit a biphasic locomotor response. However, agonists that do not induce $D_3$ receptor tolerance (PBZI) elicit a monophasic hypoactive locomotor response.

Figure 16A:
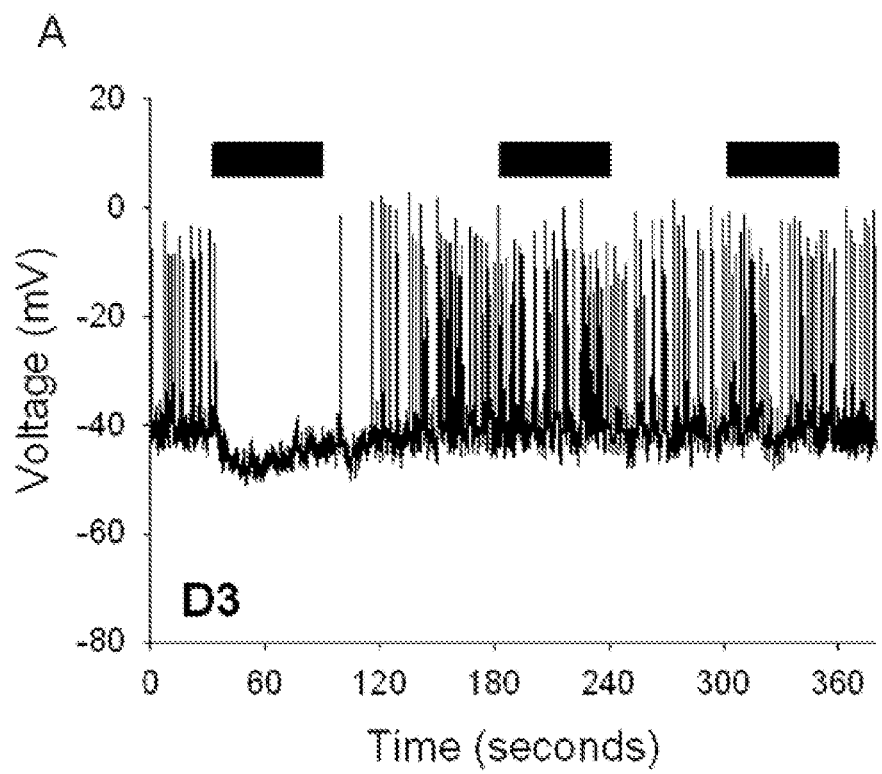
FIGS. 16A-16B illustrate the finding that activation of $D_3$ receptor by dopamine and PBZI modulates neuronal firing differently.
Figure 16B:
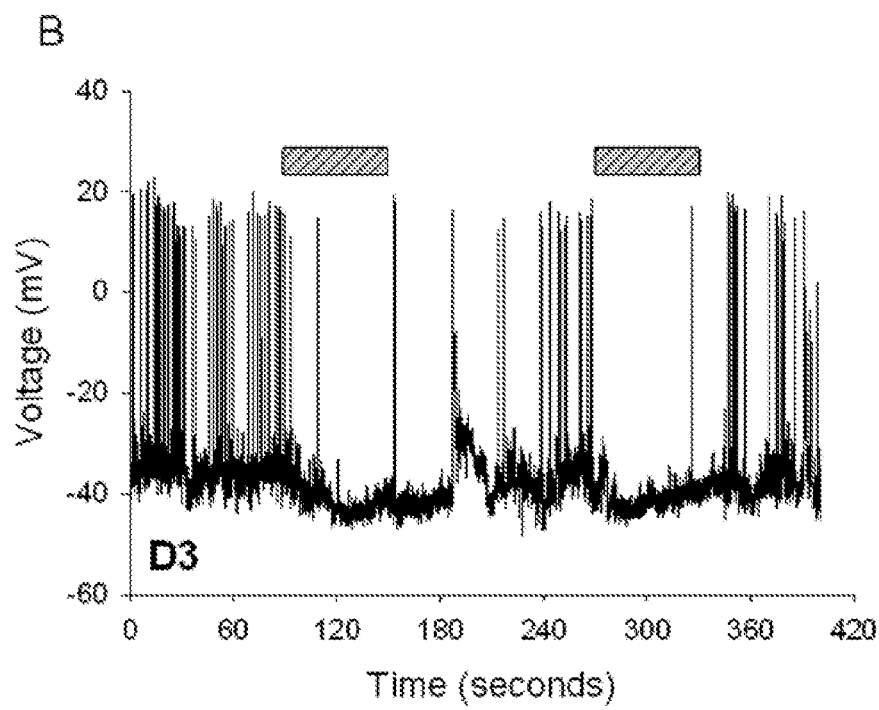

Example 7: Effect of $D_3$ Receptor Signaling Properties on Cellular Function and Signaling Pathways The stably-expressed $D_3$ receptor couples to endogenous GIRK channels in AtT-20 neuroendocrine cells and modulates spontaneous action potentials and secretion (Kuzhikandathil & Oxford, 1999, J. Neurosci. 19(5):1698-1707; Kuzhikandathil & Oxford, 2000, J. Gen. Physiol. 115:697-706; Kuzhikandathil et al., 1998, Mol. Cell Neurosci. 12:390-402). Activation of the stably expressed human $D_3$ dopamine receptor by dopamine inhibited spontaneous action potentials during the first application, but not upon subsequent applications (FIG. 16A). In contrast, the activation of the $D_3$ receptor by the tolerance and SRT abolishing agonist, PBZI, inhibited spontaneous action potentials during the first application and subsequent applications (FIG. 16B). This result suggests that the modulation of neuronal firing by $D_3$ receptor agonists that induce tolerance is very different from those that do not induce tolerance. The latter class of agonists converts the $D_3$ receptor to the functional equivalent of a $D_2$ receptor.

Example 8: Identification of a Novel Agonist that does not Induce Tolerance and SRT by Using a D3 Receptor-PBZI Pharmacophore Model The results in FIGS. 9C, 2A and 2C showed that PD128907 induces severe tolerance and SRT; interestingly, PBZI, which does not induce tolerance and SRT shares a few core structural elements with PD128907 (FIGS. 6A-6D). The stark difference in the ability of PD128907 and PBZI to induce tolerance and SRT suggested that comparative modeling studies of these compounds docked in the $D_3$ receptor homology model might yield information to develop a pharmacophore model to screen for additional compounds that abolish tolerance and SRT properties.

To further understand the difference in signaling properties induced by PD128907 and PBZI, they were docked to the binding site of the $D_3$ receptor. The docking was defined by salt bridge interactions of the protonatable amine with Asp110, hydrogen bond interactions with conserved serine residues in transmembrane (TM) 5 and aromatic interactions with residues from TM6 and TM7. The ligand bound complexes were minimized and further refined using molecular dynamics (MD) simulations. A structural super positioning of the refined complexes yielded a root mean square deviation (rmsd) of 3.5 Å with well-marked differences in the TM bundle as well as the loop regions, leading to the hypothesis that each of these agonists elicit a unique conformational change in the receptor as previously observed for quinpirole. PD128907 forms a conserved salt bridge with Asp110, hydrogen bonds with Ser193 on TM5 and aromatic interactions with His349, Trp342 and Tyr373. Since the tetrahydropyran ring of PD128907 is more electronegative than the equivalent hexahydrobenzo group of PBZI, the latter probably has fewer interactions with the hydrophobic groups in TM3 as well as other aromatic residues in TM6. PBZI forms the conserved salt bridge with Asp110, hydrogen bonds with Ser192 in TM5 and has favorable pi-pi interactions with His349 and Phe345. In addition, due to the hydrophobic nature of hexahydrobenzo group, it forms favorable interactions with Val111 in TM3, Phe197 in TM5, Trp342 in TM6 and Tyr373 in TM7.

In order to verify if these interactions of PBZI with the $D_3$ receptor were significant, a three dimensional pharmacophore incorporating the hydrophobic elements, salt bridge interaction and aromatic-pi interactions was designed. Using this three dimensional pharmacophore, a three million compound library was screened using the HSB method for small molecules that could mimic the pharmacophore features of PBZI. The hits from the screen were then subjected to filtering schemes that include Lipinski's drug-like properties, Pregnane xenobiotic receptor activation and more importantly blood brain barrier (BBB) penetration. The 290 hits that resulted from the filtering schemes were docked to the binding site of D3 receptor and scored using a variety of scoring schemes. The scoring schemes were customized to rank only those molecules that formed a salt bridge interaction with Asp110 and had favorable interactions with aromatic cluster formed by TM5, TM6 and TM7.

Figure 6D:
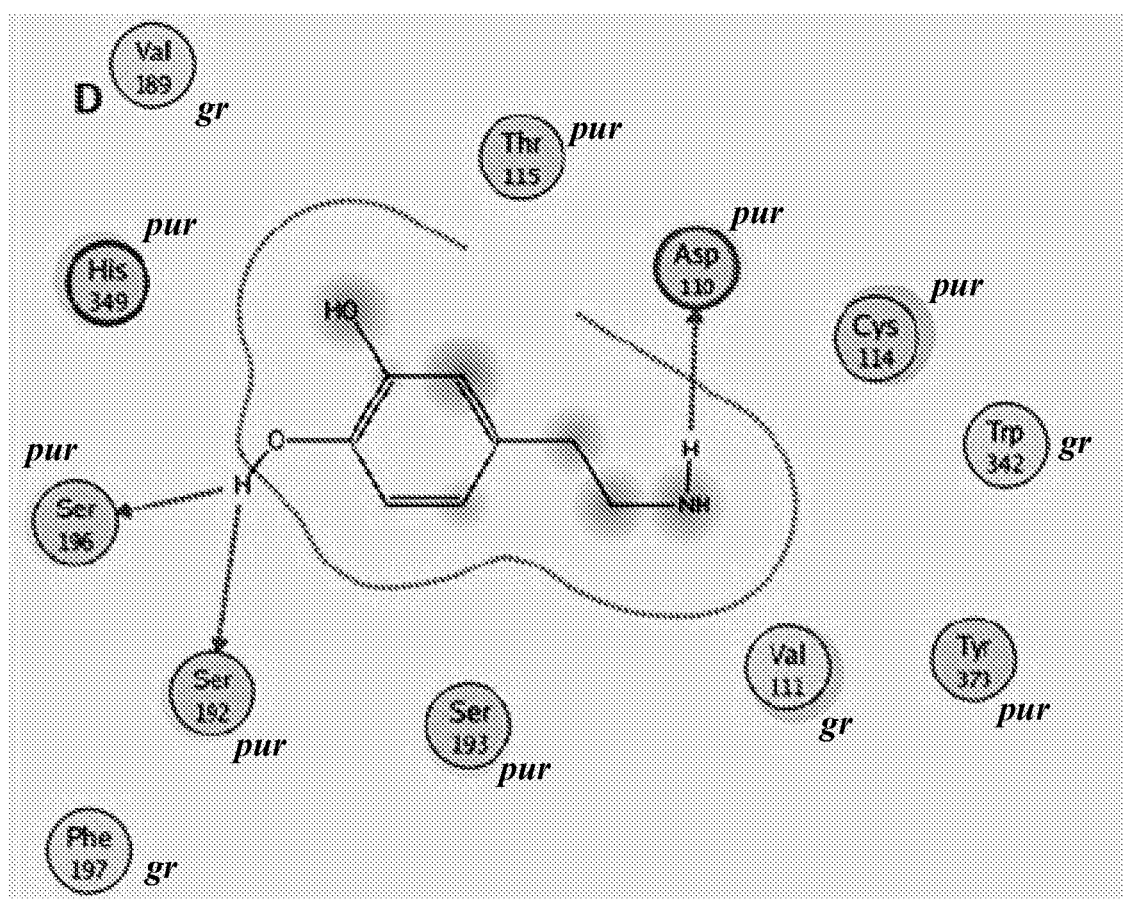
Figure 7A:
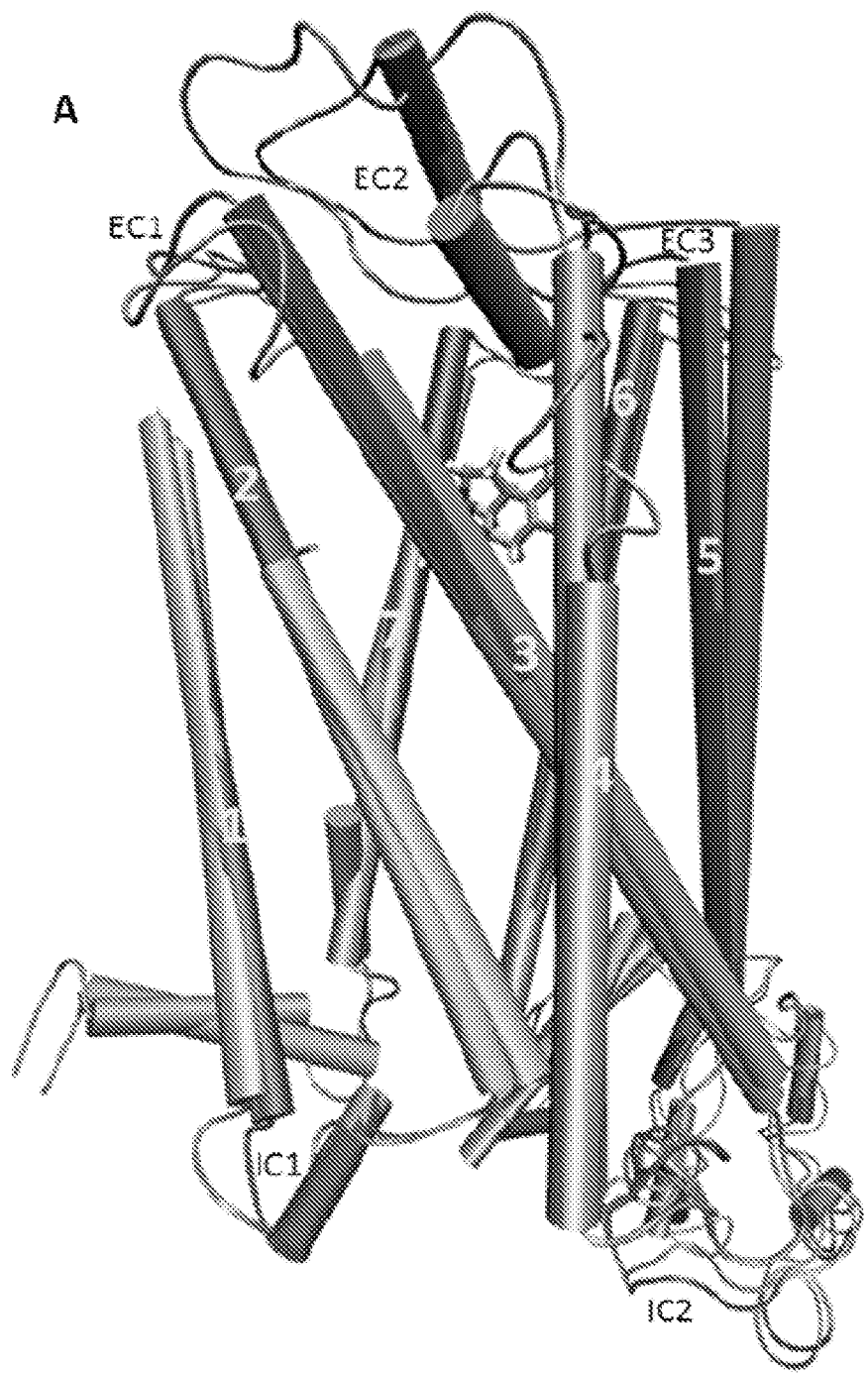
FIGS. 7A-7B are a set of molecular models illustrating that the HSB method allows for the identification of residues and conformations involved in $D_3$ receptor tolerance and SRT properties.
Figure 7B:
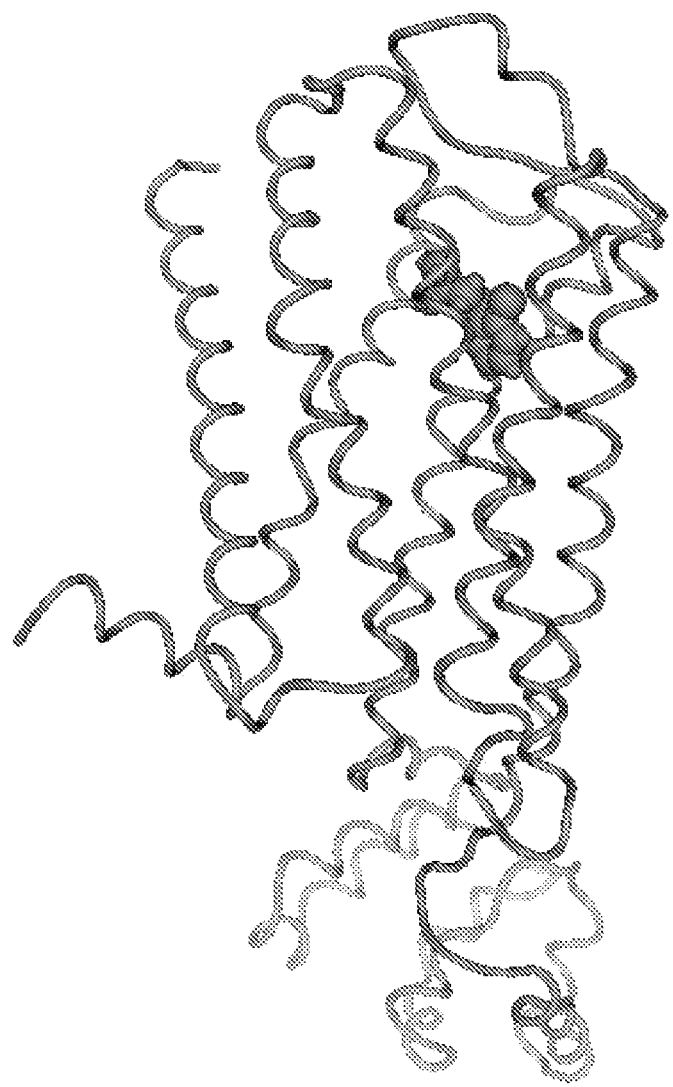
Figure 17A:
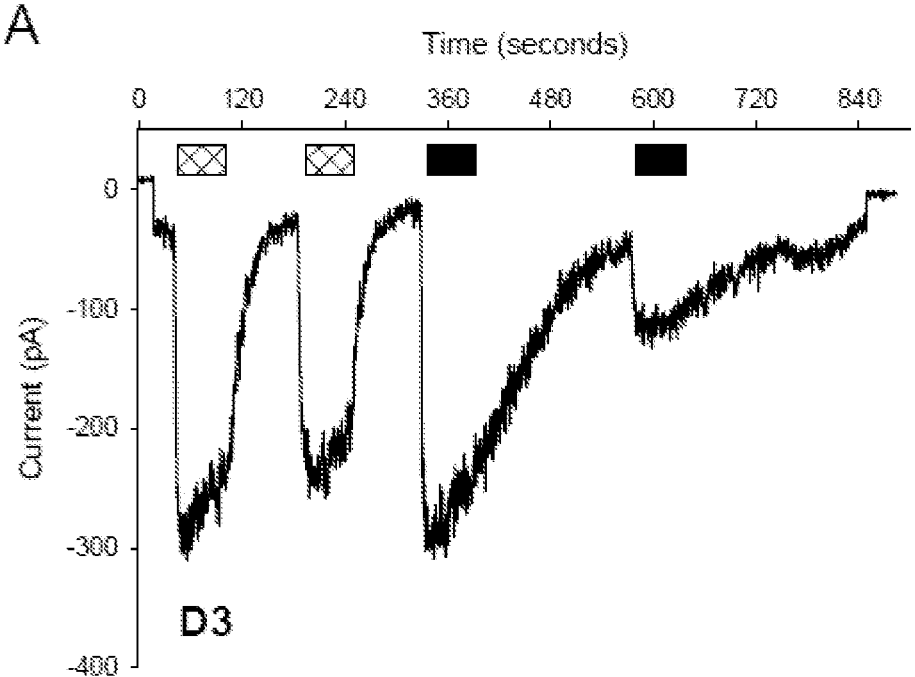
FIGS. 17A-17D are a set of graphs illustrating that the novel $D_3$ receptor agonist, ES609, abolishes tolerance and SRT properties.
Figure 17B:
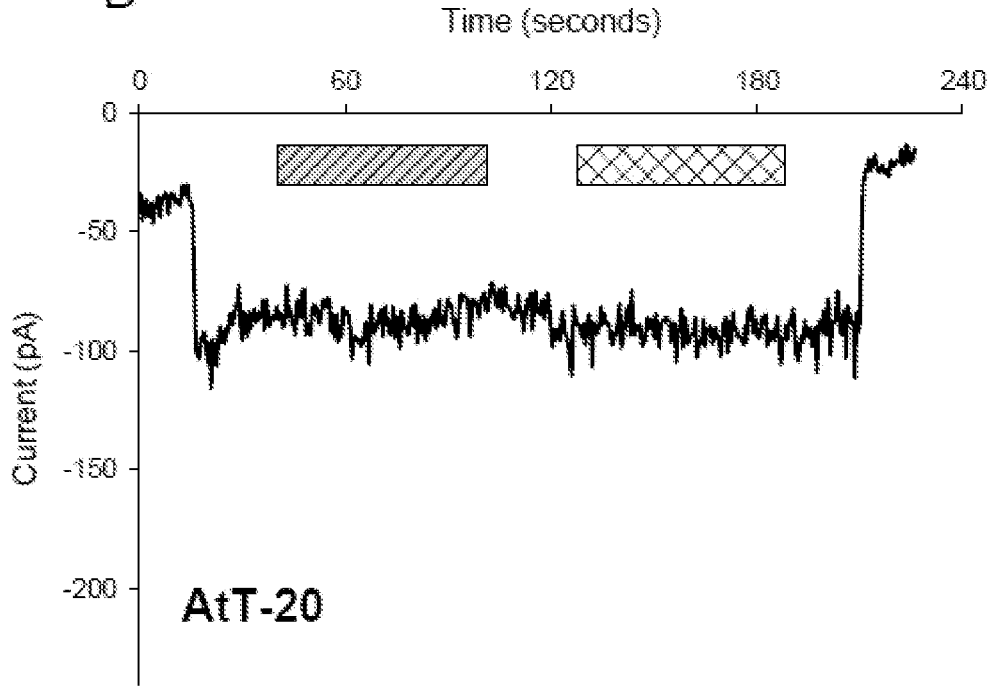
Figure 17C:
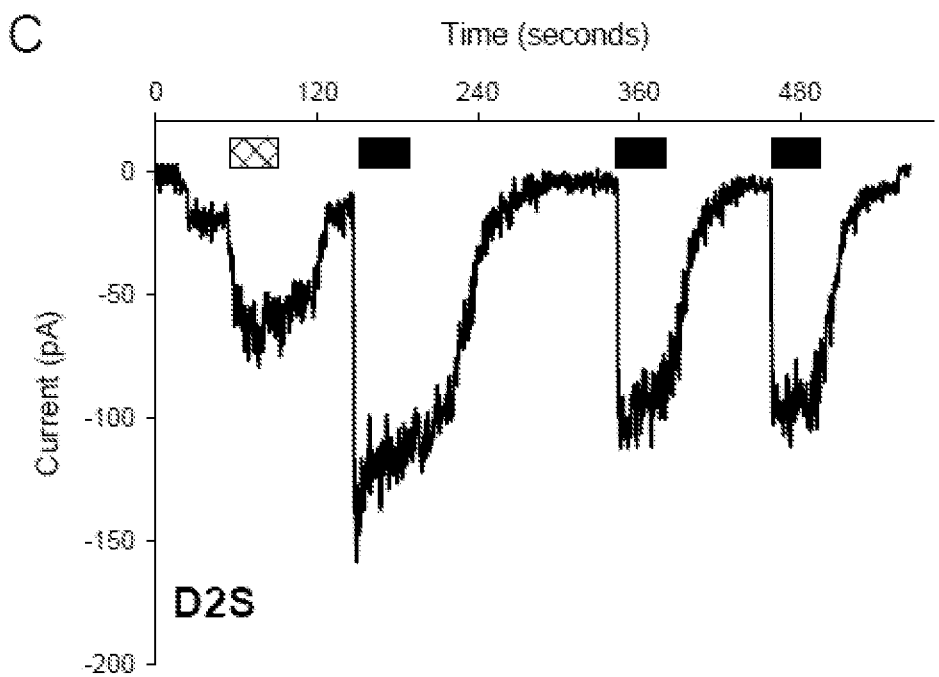
Figure 17D:
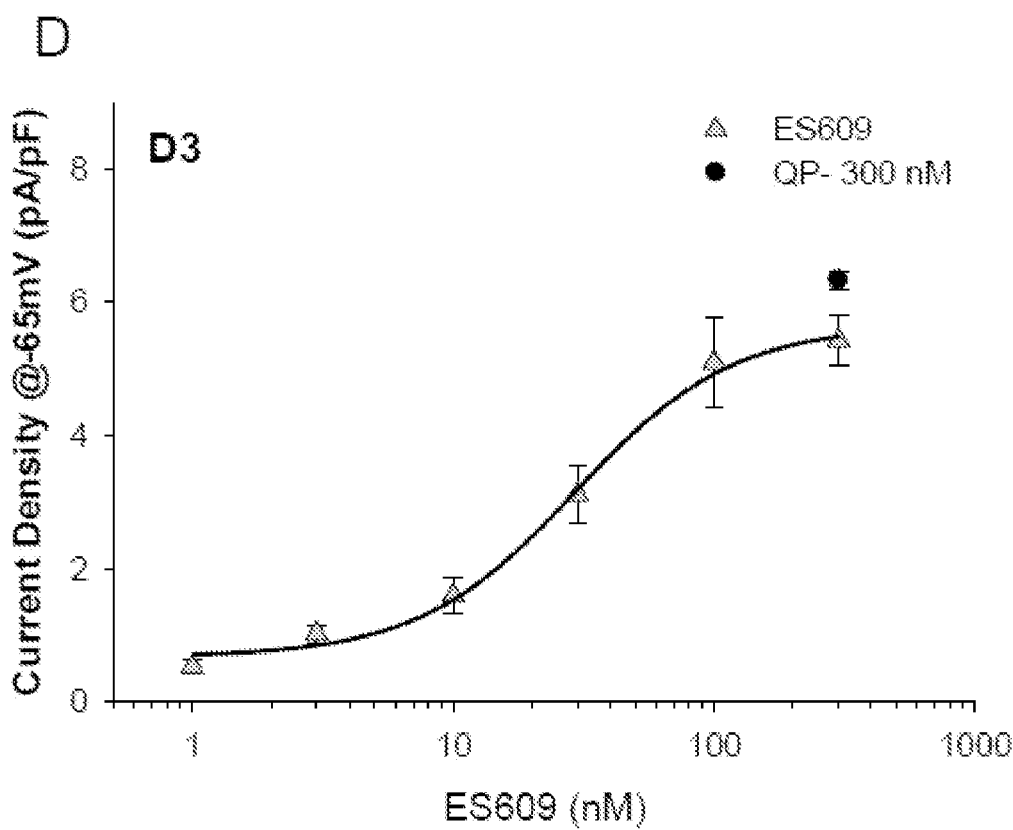
Figure 18:
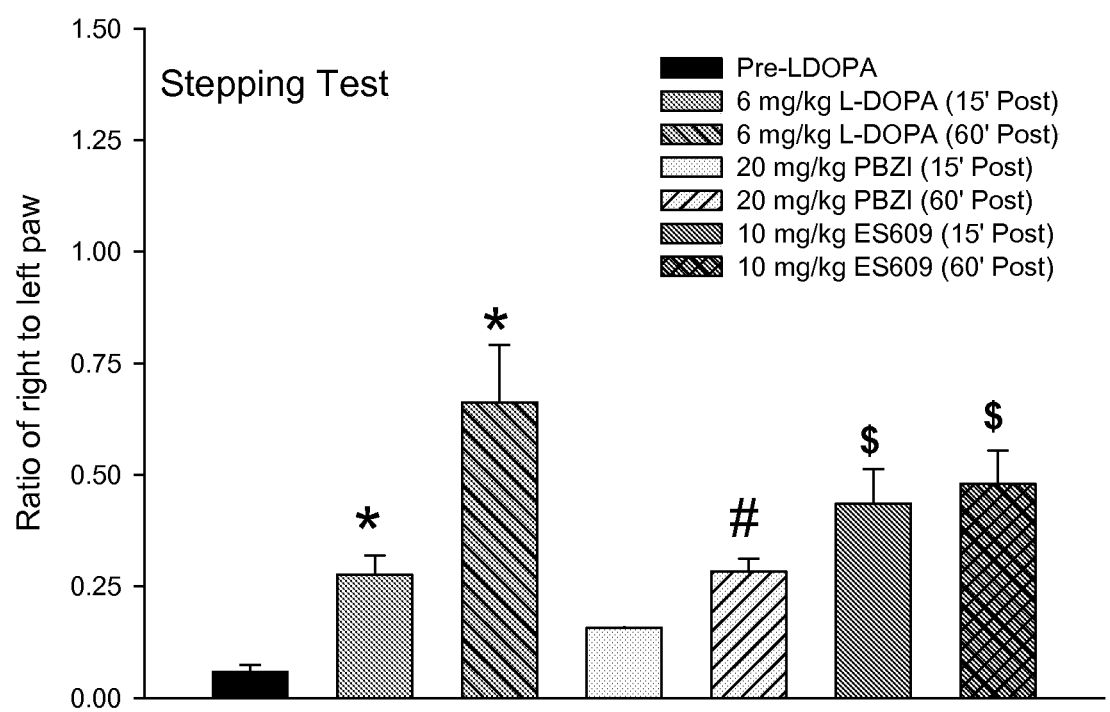
FIG. 18 is a bar graph illustrating the finding that PBZI and ES609 improve motor deficits in a rat PD model.
Figure 19A:
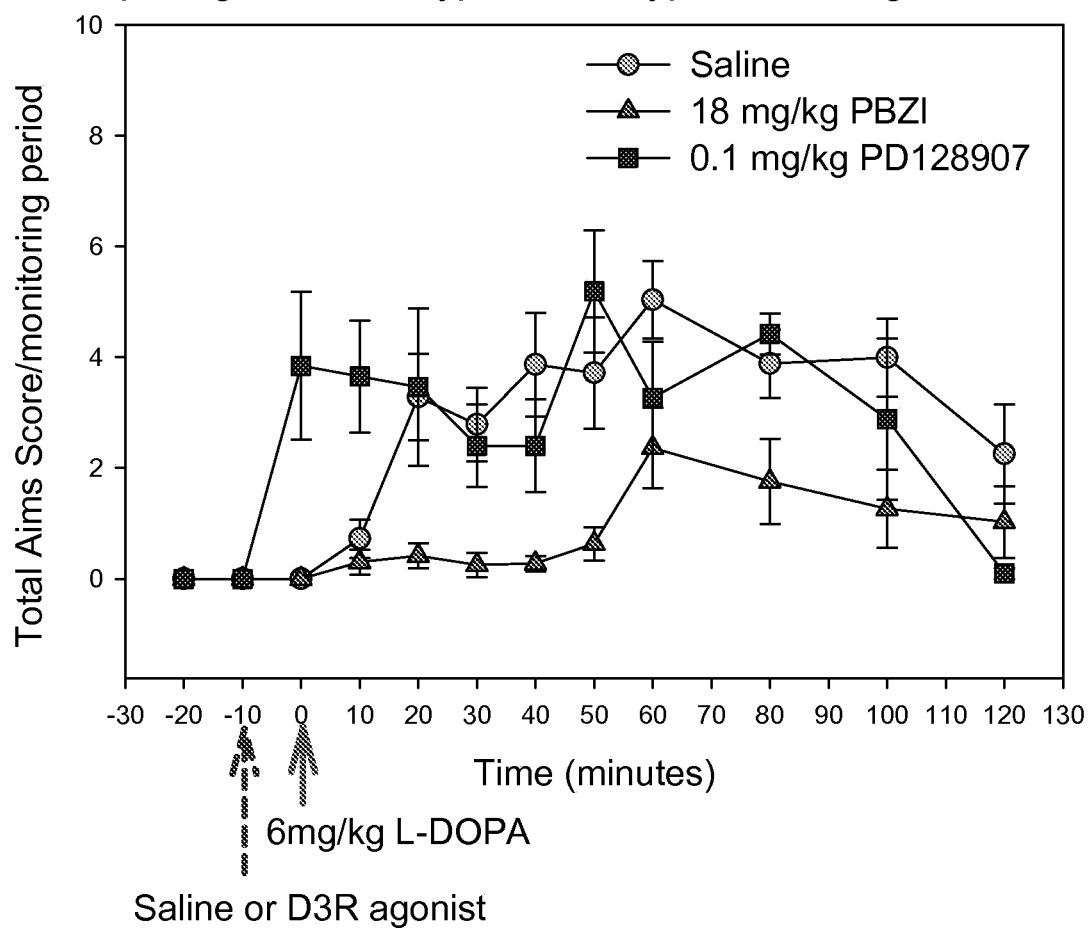
FIGS. 19A-19B are a pair of graphs illustrating the finding that PBZI & ES609 improve levodopa-induced dyskinesia in a rat PD model.
Figure 19B:
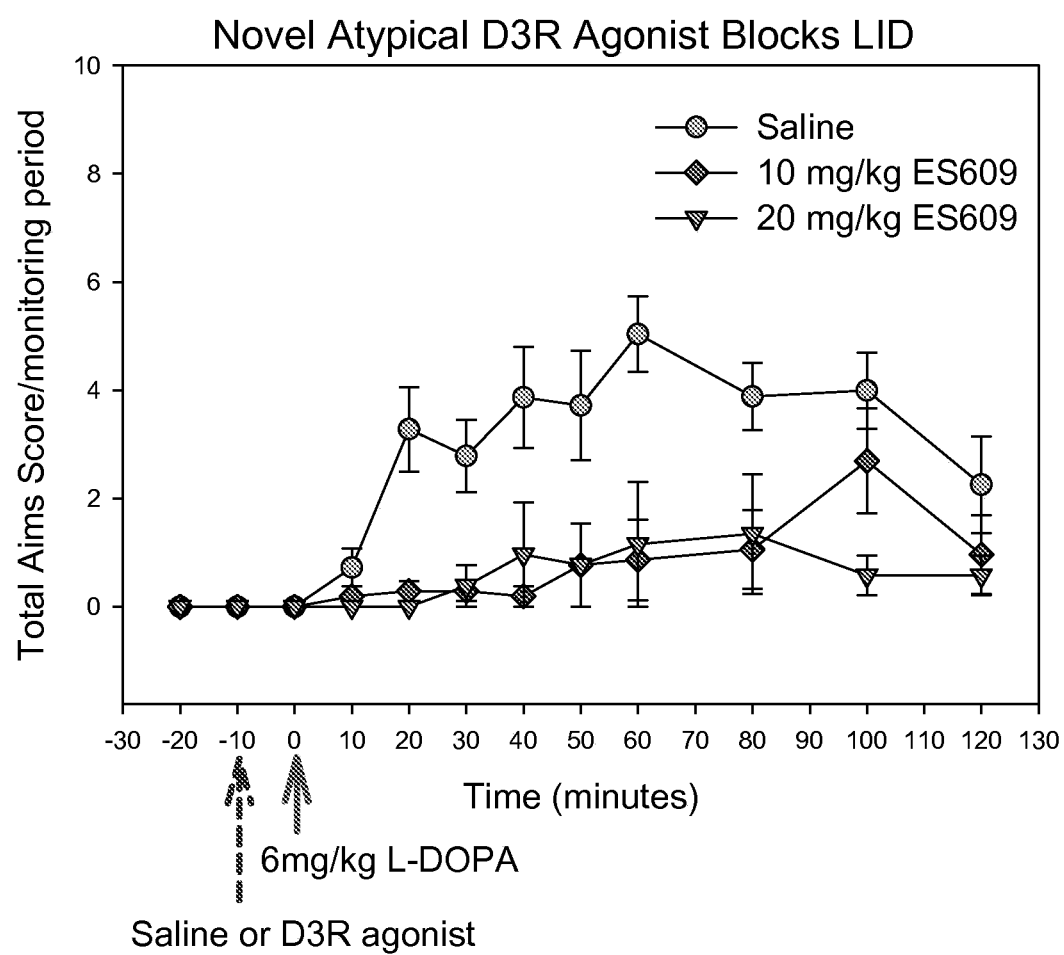
Figure 20:
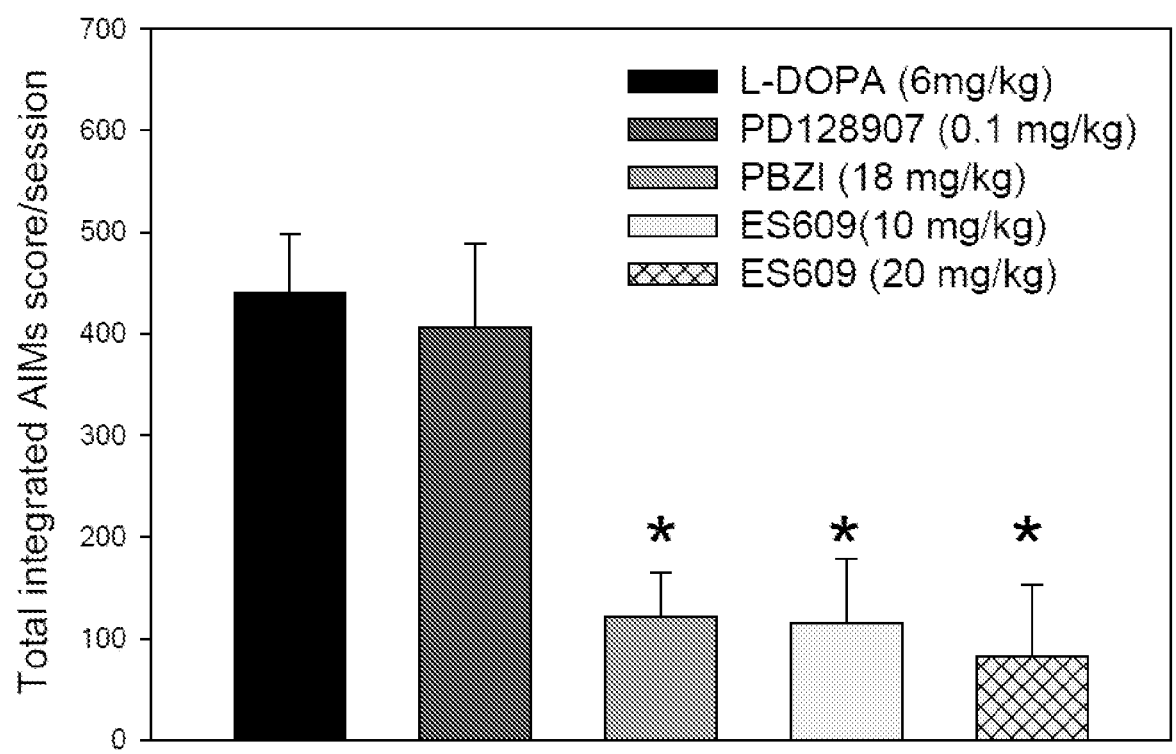
FIG. 20 is a bar graph illustrating the finding that atypical (but not typical) $D_3$ receptor agonists prevent L-DOPA induced dyskinesia.
Figure 21A:
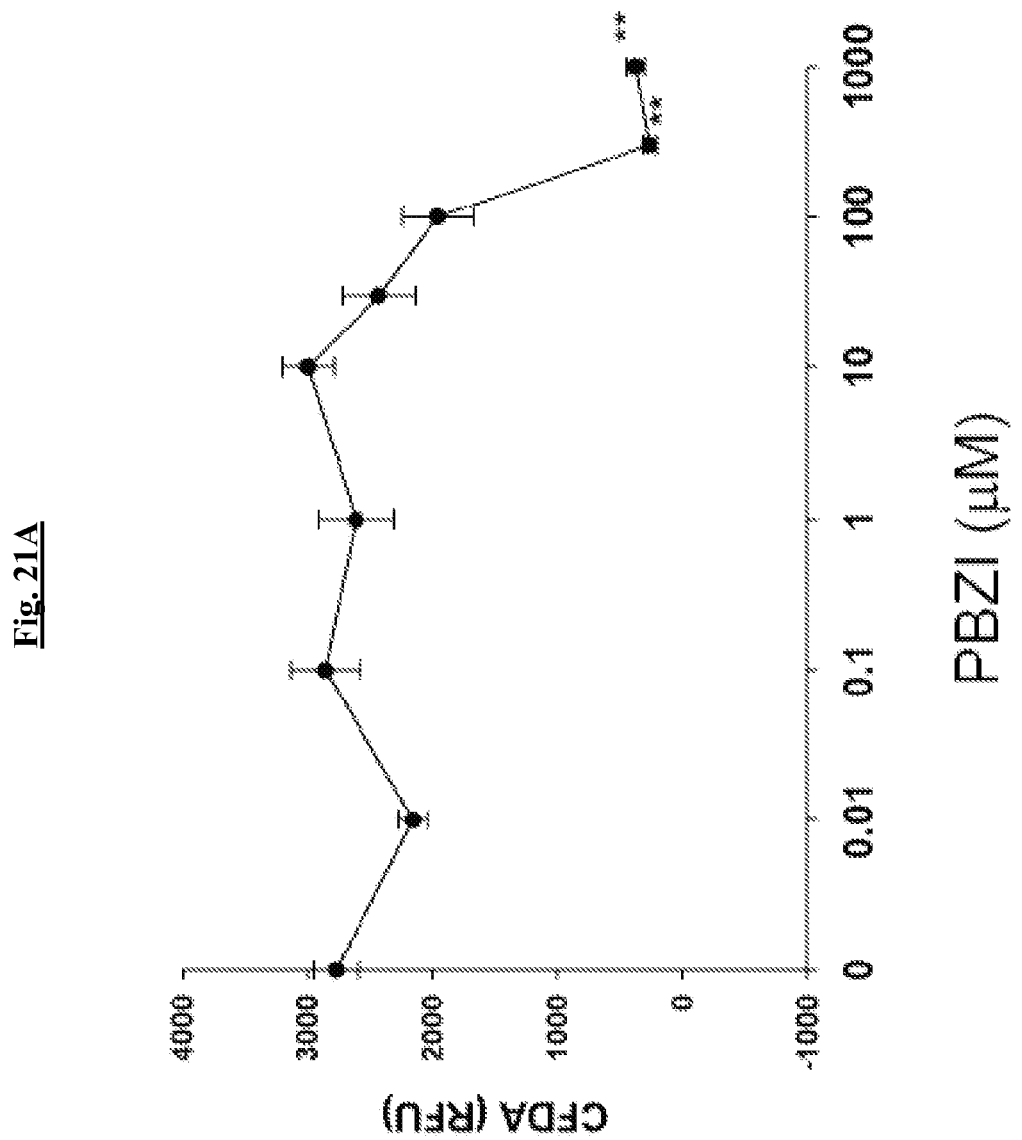
FIGS. 21A-21B are a set of graphs illustrating the effect of PBZI and ES609 on neuron viability in hippocampal cultures (from Day 2 to Day 5 in culture).
Figure 21B:
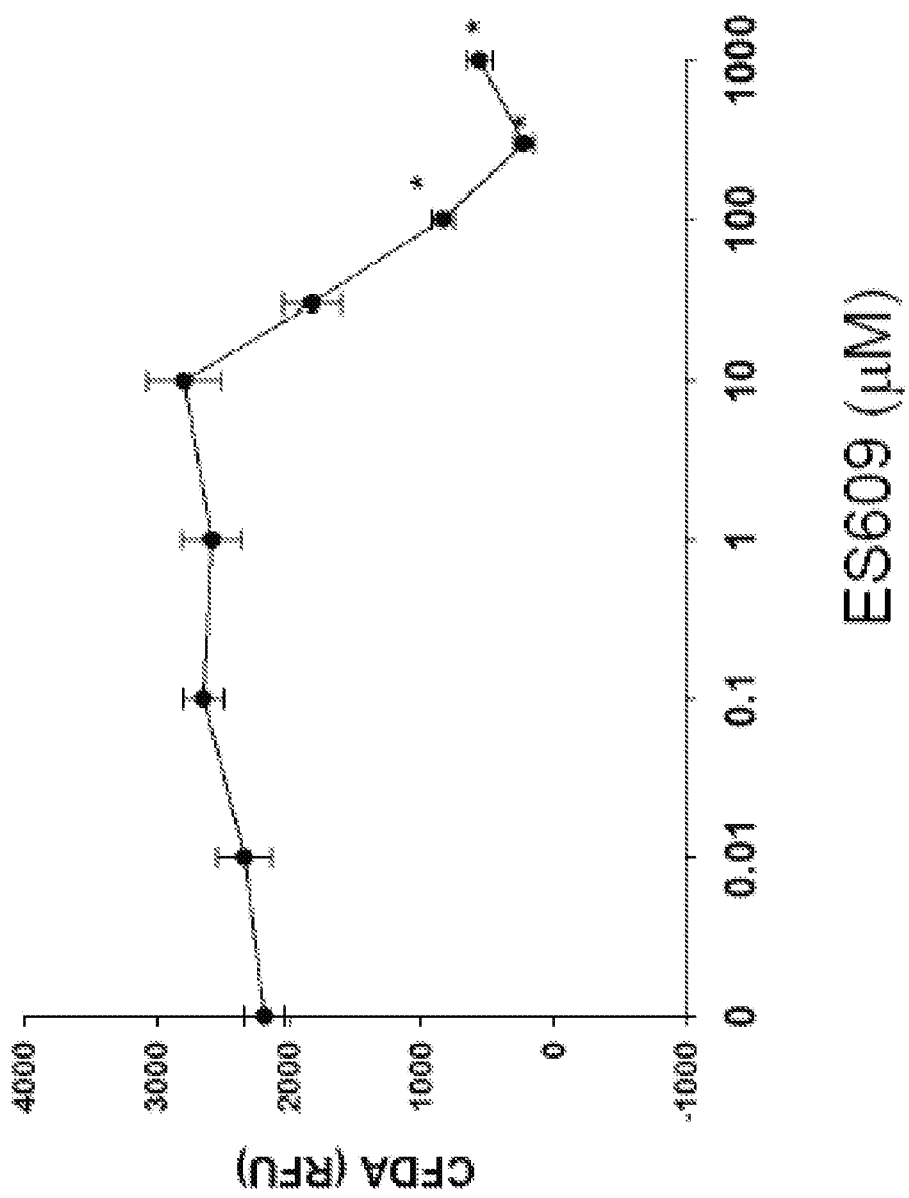
Figure 22A:
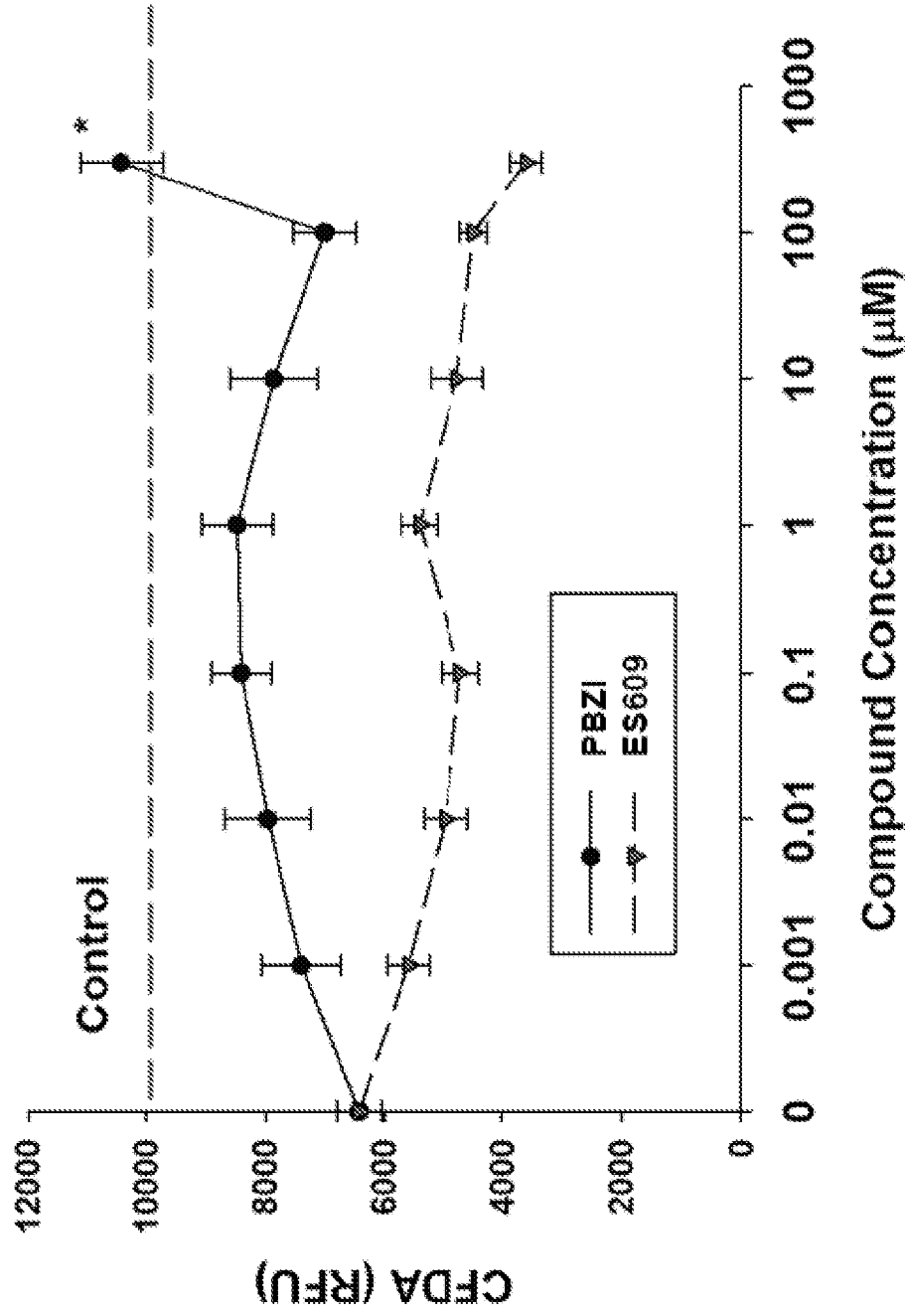
FIGS. 22A-22B are a set of graphs illustrating the effect of PBZI & ES609 on neuroprotection of hippocampal cells treated with 10 mM hydrogen peroxide for 4 hours.
Figure 22B:
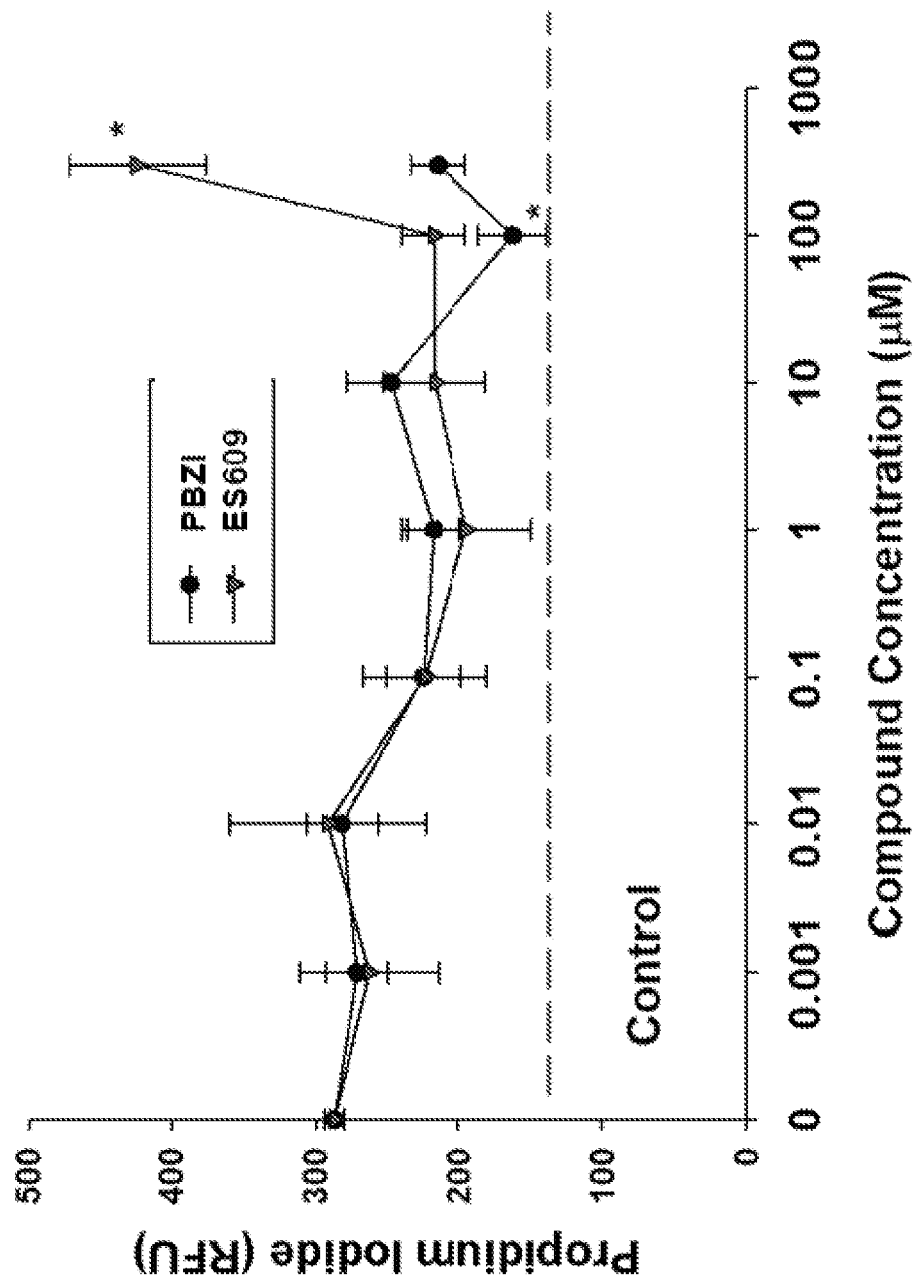
Figure 23A:
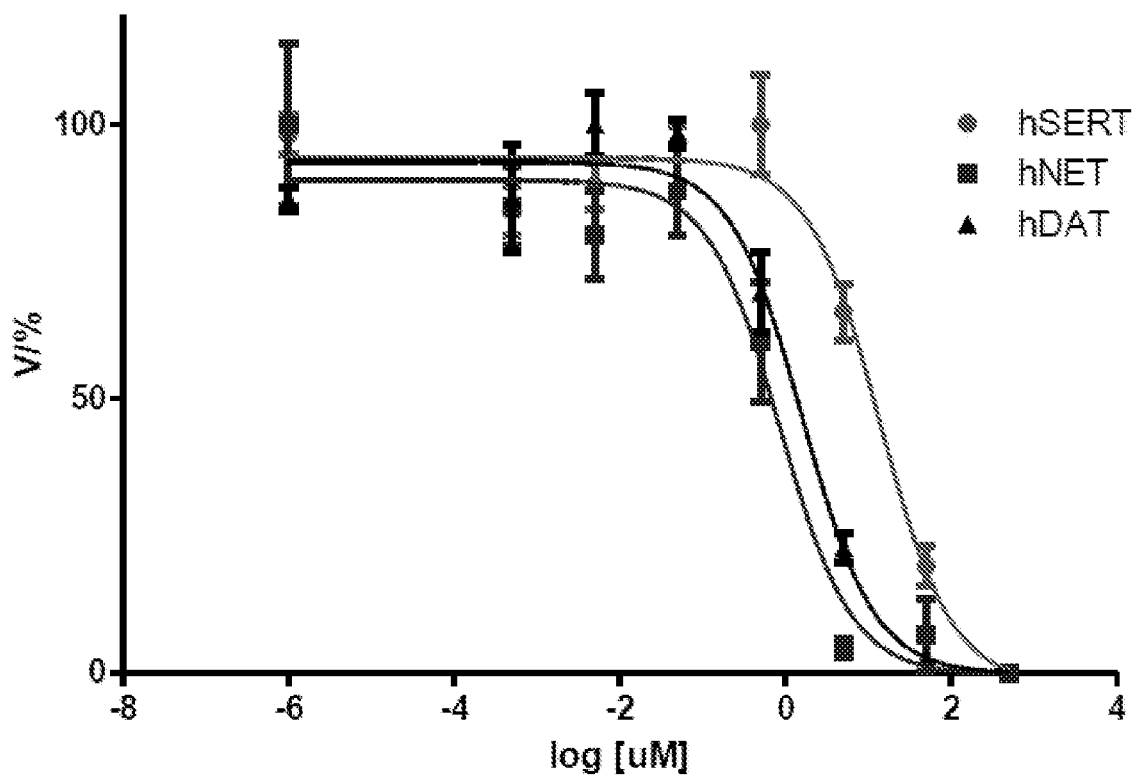
FIGS. 23A-23B are a set of graphs illustrating the finding that ES609 inhibits monoamine transporter uptake activity.
Figure 23B:
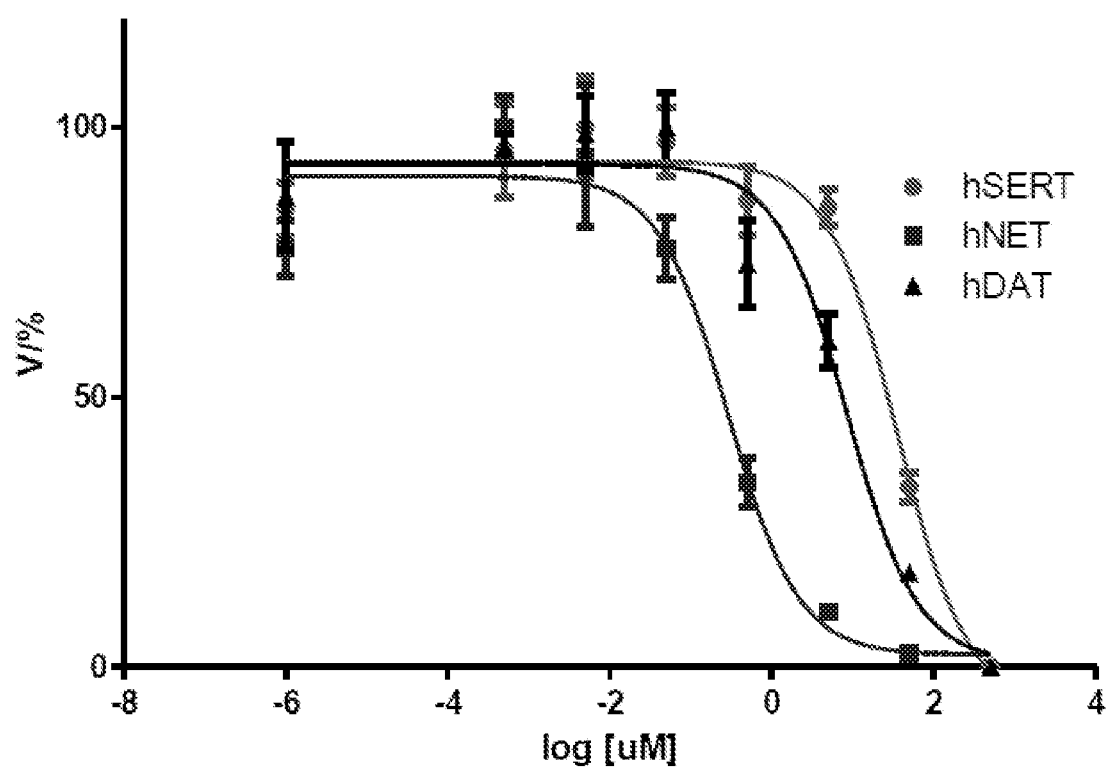

The fifteen compounds identified by the HSB in silico screen were evaluated for their ability to activate D3 receptors and induce GIRK response, tolerance and SRT. The functional studies identified a novel $D_3$ receptor agonist, ES609 (4-(2-chlorophenyl)-butan-2-amine), which did not induce tolerance and SRT. FIGS. 17A-17D show representative traces and cumulative data for ES609 and suggests that, as in the case of PBZI and FAUC73, ES609 also abolishes D3 receptor tolerance and SRT properties (FIG. 17A). Control experiments showed that ES 609 did not elicit GIRK currents in parental AtT-20 cells (FIG. 17B) and the currents induced in AtT-20 cells stably expressing the D3 receptor were blocked by pretreatment with the antagonist, eticlopride. Docking experiments confirmed that ES609 follows the interaction pattern of PBZI, with favorable pi-stacking interactions with His349 and salt bridge with Asp110 (FIG. 6A). Further refinement of the D3 receptor-ES609 complex using MD simulation studies showed that ES609 elicits a similar conformation as that of PBZI. ES609-bound D3 receptor structure super positioned on to the PBZI-bound D3 receptor structure with a rmsd of 1.2 Å (FIG. 7A). The results show that while ES609 shares the same core structure as that of dopamine (FIG. 6D), its interaction pattern as well as the conformational change it elicits in the $D_3$ receptor are similar to those of PBZI.

Example 9: Functional Characterization of PBZI and ES609

To compare the functional effects of the new class of $D_3$ receptor agonists, PBZI (Table 2) and ES609 (Table 3) were tested on AtT-20 cells stably expressing human $D_3$, $D_{2S}$, $D_{2L}$ or $D_{4.2}$. Functional efficacy was determined by assessing the ability of PBZI and ES609 to inhibit adenylyl cyclase or activate GIRK channels coupled to these "$D_2$-like" dopamine receptors. The $EC_{50}$ values of PBZI and ES609 for inhibiting adenylyl cyclase and activating GIRK channels were in the range of 0.2 nM to 30 nM for $D_3$ receptors. By comparing to responses elicited by a saturating concentration (300 nM) of the full agonist, quinpirole, the results showed that PBZI and ES609 are full agonists at $D_3$ receptors in both the adenylyl cyclase and GIRK channel assays. In contrast, both compounds were partial agonists at the $D_{2S}$ dopamine receptor. At $D_{2L}$ dopamine receptors, PBZI was a full agonist in both assays; in contrast, ES609 did not elicit any response in the adenylyl cyclase assay and was a partial agonist in the GIRK channel assay. At $D_{4.2}$ dopamine receptors, PBZI elicited no response and ES609 was a partial agonist in the adenylyl cyclase assay. In the GIRK channel assay, PBZI was a partial agonist at D4.2 receptors, while ES609 elicited no response. Together these results suggest that both PBZI and ES609, are full agonists at $D_3$ receptor, and were either partial agonists or elicited no responses at other $D_2$-like dopamine receptors.

TABLE 2

Cis-8OH-PBZI induced inhibition of adenylyl cyclase and activation of GIRK channels in AtT-20 cells stably expressing the individual dopamine receptor subtypes

| $D_2$-like dopamine receptors | Adenylyl cyclase inhibition $EC_{50}$ (nM) | Adenylyl cyclase inhibition Ratio of PBZI to quinpirole response (at 300 nM) | GIRK channel activation $EC_{50}$ (nM) | GIRK channel activation Ratio of PBZI to quinpirole response (at 300 nM) |
|---|---|---|---|---|
| $D_{2S}$ | >150 | 0.29* | 53 ± 19.8 | 0.48* |
| $D_{2L}$ | 67 ± 15 | 0.83 | ND | 0.75 |
| $D_3$ | 35 ± 2.8 | 0.97 | 29 ± 16.1 | 1.3 |
| $D_{4.2}$ | No response | 0† | ND | 0.35* |

*$P < 0.05$, statistically significant, Student's t-test.
†no adenylyl cyclase inhibition in the presence of 300 nM PBZI; but 300 nM quinpirole elicits ~70% inhibition.
ND—not determined; a full dose-response experiment to determine EC50 was not performed; data was obtained for a single concentration (300 nM) of PBZI.
± Standard Error of Mean.

TABLE 3

ES609 induced inhibition of adenylyl cyclase and activation of GIRK channels in AtT-20 cells stably expressing the individual dopamine receptor subtypes

| D2-like dopamine receptors | Adenylyl cyclase inhibition $EC_{50}$ (nM) | Adenylyl cyclase inhibition Ratio of ES609 to quinpirole response (at 300 nM) | GIRK channel activation $EC_{50}$ (nM) | GIRK channel activation Ratio of ES609 to quinpirole response (at 300 nM) |
|---|---|---|---|---|
| $D_{2S}$ | 2.4 ± 0.2 | 0.29* | ND | 0.30* |
| $D_{2L}$ | No response | 0† | ND | 0.32* |
| $D_3$ | 0.15 ± 0.06 | 0.71 | 30 ± 7.7 | 0.86 |
| $D_{4.2}$ | 0.82 ± 0.3 | 0.60* | No response | 0†† |

*$P < 0.05$, statistically significant, Student's t-test.
†no adenylyl cyclase inhibition in the presence of 300 nM ES609; but 300 nM quinpirole elicits ~80% inhibition.
††300 nM ES609 elicits no GIRK response; but, 300 nM quinpirole elicits a full GIRK response.
ND—not determined; a full dose-response experiment to determine $EC_{50}$ was not performed; data was obtained for a single concentration (300 nM) of ES609.
± Standard Error of Mean.

The results described herein demonstrate that the $D_3$ receptor tolerance and SRT properties are ligand-dependent and help identify a new class of atypical $D_3$ receptor agonists that do not induce these properties. PBZI, a water soluble compound that is structurally similar to PD128907 but does not induce tolerance and SRT, was identified. Previous binding studies have shown that for $D_2$-like receptors, PBZI has a Ki of 27 nM for $D_3$, 1800 nM for $D_{2S}$ and 280 nM for $D_{4.2}$ (Scheideler et al., 1997, Eur. J. Pharmacol. 339(2-3): 261-270). Binding at $D_1$-like receptors and a panel of other neurotransmitter receptors, ion channels and transporters were negligible. Thus PBZI exhibited $D_3$ receptor selectivity in receptor binding assay. This is consistent with the result from the functional studies, which shows that PBZI is a full agonist at $D_3$ receptors and a partial agonist at the D2S dopamine receptors (Table 2). The partial agonistic effect at $D_{2S}$ receptors is also consistent with previous in vitro results. In vivo, animals administered PBZI show specific increases in c-fos expression in medial prefrontal cortex and the shell region of nucleus accumbens, regions with high D3 receptor expression. Effect of PBZI on $D_{2L}$ receptors had not been previously determined. The results described herein show that PBZI is a full agonist at the $D_{2L}$ dopamine receptor (Table 2). Based on the pre- and post-synaptic location of D2S and D2L receptors, respectively, PBZI would be predicted to primarily have postsynaptic effects. This is supported by previous in vivo studies as well (Fink-Jensen et al., 1998, Eur. J. Pharmacol. 342(2-3):153-161).

The classical $D_2$-like receptor agonist, PD128907, is selective for $D_3$ receptor with a Ki of 0.4 nM for $D_3$, 202 nM for $D_{2S}$ and 114 nM for $D_{4.2}$ (Scheideler et al., 1997, Eur. J. Pharmacol. 339(2-3):261-270); however the studies described herein showed that it induces severe tolerance and SRT. Interestingly, the chemical structure of PD128907 is similar to PBZI. Although PD128907 and PBZI share a similar core structure and function as full agonists at $D_3$ receptor, they have dramatically different effects on the tolerance and SRT properties. The results described herein suggest that the functional differences between PBZI and PD128907 are due to the different conformation these agonists induce in the $D_3$ receptor. The majority of these conformational changes are confined to the regions closest to the binding site and extracellular loop (EC) 2 loop region. Comparison of the PBZI- and PD128907-bound structures suggests that the maximum shift occurs in TM4, which is coupled with large movements of EC2. In addition, the conformational changes are also observed in intracellular loop (IC) 2 which has previously shown to be important for mediating the tolerance property (Westrich et al., 2010, Biochem. Pharmacol. 79:897-907). Other significant conformational changes include a downward shift along the length of the TM6 helix and an unwinding of the first turn of the TM3 helix in the PD128907-bound form.

In this study, by carefully monitoring the nature of interactions and the conformational effects produced by the binding of PBZI and PD128907 in computational models, a novel atypical D3 receptor agonist, ES609, which exhibits selectivity and abolishes the tolerance and SRT properties, was designed. The HSB method may be used to identify additional atypical $D_3$ receptor agonists. ES609 was designed based on the nature of interactions of PBZI with $D_3$ receptor. The hypothesis was to increase the strength of the pi-pi interactions with the aromatic core by introducing electron withdrawing groups on the ligand. Thus the halogen group at ortho position in ES609 was highly suitable to the design, along with the added hydrophobicity proximal to the protonatable amine (FIG. 6D). The latter strengthened the interactions with hydrophobic groups on TM3 similar to the interactions of FAUC73 with residues in TM3. His349 may play a major role in promoting ligand biased signaling in D2L receptor. These results are consistent with the findings that strengthening the pi-pi interactions with His349 and other members of the aromatic core may contribute favorably to the atypical properties of PBZI, FAUC73 and ES609. Studies are geared towards understanding the specific role of EC2 and TM4 in promoting functional selectivity and to further understand the complete structure-activity-relationship of these atypical agonists in complex with $D_3$ receptor. Functionally, ES609 and PBZI have similar efficacy for activating $D_3$ receptor coupled signal transduction pathways. However in contrast to PBZI, ES609 is either a partial agonist or elicits no response at other $D_2$-like receptors ($D_{2S}$, $D_{2L}$ and $D_{4.2}$) when tested in two different signaling pathways. The selectivity exhibited by ES609 suggests that its structure could serve as a template for designing future selective D3 receptor agonists. The functional affinity of ES609, defined by it $EC_{50}$, is similar to other $D_2$-like dopamine receptor agonists in the two signaling pathways that we studied. Furthermore, its small molecular weight and water solubility makes it ideally suited for in vivo studies. Given that PBZI and ES609 have similar signaling properties in vitro, they are expected to have a similar effect in vivo.

The new class of atypical $D_3$ receptor agonists described here represents a novel variation to the concept of functional selectivity. Traditionally, functional selectivity is ascribed to the ability of different ligands to elicit varying responses in different signal transduction pathways coupled to the same receptor. The ability of ligands to activate different pathways coupled to the same receptor to different degree is due to the different conformations that the ligand engenders in the receptor. Given that the $D_3$ receptor tolerance and SRT properties are determined by distinct conformations states, the identification of ligands that alters these conformation states is predicted to modulate the two properties. Consistent with this prediction, in this study a group of ligands that alter the two D3 receptor properties was identified. The results described herein indicate that the functional selectivity concept may not be limited to selective activation of different pathways coupled to the same receptor but could also be expanded to include ligands that modulate the signaling properties in a single pathway. If these properties span multiple signaling pathways, as is the case here, ectopic expression or alterations in these specific properties could underlie the pathology of various disorders. In this context, these receptor properties, exemplified by the tolerance and SRT properties of the D3 receptor, might represent a novel drug target. The studies described herein allow the identification of a new class of agonists that specifically target these two $D_3$ receptor signaling properties.

The ectopic expression of $D_3$ receptor tolerance and SRT properties in the striatum of animals with levodopa-induced dyskinesia has been proposed to contribute to the dyskinetic behavior. The atypical $D_3$ receptor agonists by abolishing tolerance and SRT might improve the levodopa-induced dyskinetic symptoms. Changes in $D_3$ receptor expression taken in the context of tolerance and SRT properties might provide explanations for some of the behavioral phenotypes observed in neurological disorders such as schizophrenia, psychosis, chronic cocaine use, stress, and depression. The ectopic expression changes of $D_3$ receptor likely affects the ratio of $D_3/D_2$ receptor expression in many of these disorders, leading to the observed pathology. The new class of atypical $D_3$ receptor agonists described here, by converting the $D_3$ receptor signaling to functional equivalent of a $D_2$ receptor, might provide a novel therapeutic approach to treat these disorders.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating or ameliorating levodopa-induced dyskinesia in a patient suffering from Parkinson's Disease, the method comprising administering to the patient a therapeutically effective amount of at least one compound selected from the group consisting of:

a compound of formula (IIa) or (IIb):

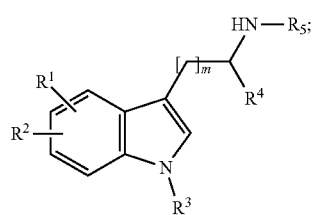
(IIa)

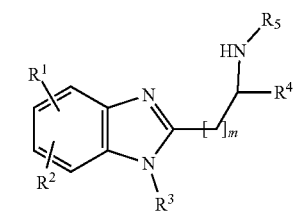
(IIb)

wherein in formula (IIa) or (IIb):
R$^1$ is independently selected from the group consisting of H, cyano halogen, C$_1$-C$_6$ alkoxy, nitro, and C$_1$-C$_6$ alkyl;
R$^2$ is independently selected from the group consisting of cyano, halogen, C$_1$-C$_6$ alkoxy, nitro, and C$_1$-C$_6$ alkyl;
R$^3$ and R$^4$ are independently selected from the group consisting of H and methyl;
R$^5$ is selected from the group consisting of H and C$_1$-C$_6$ alkyl; and,
m is 1;
2,7-diamino-5-(4-fluorophenyl)-4-oxo-3,4,5,6-tetrahydropyrido[2,3-d]pyrimidine-6-carbonitrile; (Z)-2-(1H-benzo[d]imidazol-2-yl)-N'-hydroxy-3-(4-methoxyphenyl)propanimidamide;
or a salt thereof, or any mixtures thereof.

2. The method of claim 1, wherein the at least one compound is selected from the group consisting of:
2-(5-chloro-1-methyl-1H-indol-3-yl)ethanamine;
1-(5-fluoro-1-methyl-1H-indol-3-yl)propan-2-amine;
1-(5-methoxy-1-methyl-1H-indol-3-yl)propan-2-amine;
2,7-diamino-5-(4-fluorophenyl)-4-oxo-3,4,5,6-tetrahydropyrido[2,3-d]pyrimidine-6-carbonitrile; (Z)-2-(1H-benzo[d]imidazol-2-yl)-N'-hydroxy-3-(4-methoxyphenyl)propanimidamide;
or a salt thereof, or any mixtures thereof.

3. The method of claim 1, wherein the patient is further administered a drug selected from the group consisting of levodopa, clozapine, bromocriptine, pergolide, pramipexole, ropinirole, piribedil, cabergoline, apomorphine, and lisuride, or a salt thereof, or any mixtures thereof.

4. The method of claim 1, wherein the at least one compound is co-administered to the patient with levodopa.

5. The method of claim 1, wherein the at least one compound is administered to the patient a given period of time before levodopa is administered to the patient.

6. The method of claim 5, wherein the given period of time varies from about 2 minutes to about 24 hours.

7. The method of claim 1, wherein the patient is human.

8. A method of treating and ameliorating Parkinson's Disease in a patient, the method comprising administering to the patient a therapeutically effective amount of at least one compound selected from the group consisting of:

a compound of formula (IIa) or (IIb):

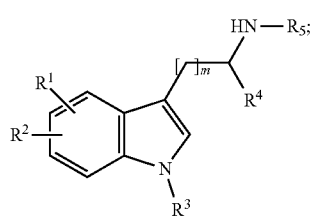
(IIa)

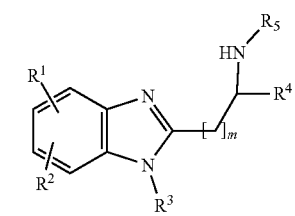
(IIb)

wherein in formula (IIa) or (IIb):
R$^1$ is independently selected from the group consisting of H, cyano halogen, C$_1$-C$_6$ alkoxy, nitro, and C$_1$-C$_6$ alkyl;
R$^2$ is independently selected from the group consisting of cyano, halogen, C$_1$-C$_6$ alkoxy, nitro, and C$_1$-C$_6$ alkyl;
R$^3$ and R$^4$ are independently selected from the group consisting of H and methyl;
R$^5$ is selected from the group consisting of H and C$_1$-C$_6$ alkyl; and,
m is 1;
2,7-diamino-5-(4-fluorophenyl)-4-oxo-3,4,5,6-tetrahydropyrido[2,3-d]pyrimidine-6-carbonitrile; (Z)-2-(1H-benzo[d]imidazol-2-yl)-N'-hydroxy-3-(4-methoxyphenyl)propanimidamide;
or a thereof, or any mixtures thereof.

9. The method of claim 8, wherein the at least one compound is selected from the group consisting of:
- 1-(5-fluoro-1-methyl-1H-indol-3-yl)propan-2-amine;
- 1-(5-methoxy-1-methyl-1H-indol-3-yl)propan-2-amine;
- 2,7-diamino-5-(4-fluorophenyl)-4-oxo-3,4,5,6-tetrahydropyrido[2,3-d]pyrimidine-6-carbonitrile; (Z)-2-(1H-benzo[d]imidazol-2-yl)-N'-hydroxy-3-(4-methoxyphenyl)propanimidamide;
- or a salt thereof, or any mixtures thereof.

10. The method of claim 8, wherein the at least one compound is formulated as a pharmaceutical composition further comprising at least one drug selected from the group consisting of levodopa, clozapine, bromocriptine, pergolide, pramipexole, ropinirole, piribedil, cabergoline, apomorphine, lisuride, a salt thereof, or any mixtures thereof.

11. The method of claim 8, wherein the patient is further administered at least one drug selected from the group consisting of levodopa, clozapine, bromocriptine, pergolide, pramipexole, ropinirole, piribedil, cabergoline, apomorphine, lisuride, a salt thereof, or any mixtures thereof.

\* \* \* \* \*

SEQUENCE LISTING

```
<160> NUMBER OF SEQ ID NOS: 2

<210> SEQ ID NO 1
<211> LENGTH: 400
<212> TYPE: PRT
<213> ORGANISM: Homo sapiens

<400> SEQUENCE: 1

Met Ala Ser Leu Ser Gln Leu Ser His Leu Asn Tyr Thr Cys Gly
1               5                   10                  15

Ala Glu Asn Ser Thr Gly Ala Ser Gln Ala Arg Pro His Ala Tyr Tyr
                20                  25                  30

Ala Leu Ser Tyr Cys Ala Leu Ile Leu Ala Ile Val Phe Gly Asn Gly
            35                  40                  45

Leu Val Cys Met Ala Val Leu Lys Glu Arg Ala Leu Gln Thr Thr Thr
        50                  55                  60
```

Asn Tyr Leu Val Val Ser Leu Ala Val Ala Asp Leu Leu Val Ala Thr
65                  70                  75                  80

Leu Val Met Pro Trp Val Val Tyr Leu Glu Val Thr Gly Gly Val Trp
            85                  90                  95

Asn Phe Ser Arg Ile Cys Cys Asp Val Phe Val Thr Leu Asp Val Met
            100                 105                 110

Met Cys Thr Ala Ser Ile Leu Asn Leu Cys Ala Ile Ser Ile Asp Arg
            115                 120                 125

Tyr Thr Ala Val Val Met Pro Val His Tyr Gln His Gly Thr Gly Gln
130                 135                 140

Ser Ser Cys Arg Arg Val Ala Leu Met Ile Thr Ala Val Trp Val Leu
145                 150                 155                 160

Ala Phe Ala Val Ser Cys Pro Leu Leu Phe Gly Phe Asn Thr Thr Gly
            165                 170                 175

Asp Pro Thr Val Cys Ser Ile Ser Asn Pro Asp Phe Val Ile Tyr Ser
            180                 185                 190

Ser Val Val Ser Phe Tyr Leu Pro Phe Gly Val Thr Val Leu Val Tyr
            195                 200                 205

Ala Arg Ile Tyr Val Val Leu Lys Gln Arg Arg Arg Lys Arg Ile Leu
210                 215                 220

Thr Arg Gln Asn Ser Gln Cys Asn Ser Val Arg Pro Gly Phe Pro Gln
225                 230                 235                 240

Gln Thr Leu Ser Pro Asp Pro Ala His Leu Glu Leu Lys Arg Tyr Tyr
            245                 250                 255

Ser Ile Cys Gln Asp Thr Ala Leu Gly Gly Pro Gly Phe Gln Glu Arg
            260                 265                 270

Gly Gly Glu Leu Lys Arg Glu Glu Lys Thr Arg Asn Ser Leu Ser Pro
            275                 280                 285

Thr Ile Ala Pro Lys Leu Ser Leu Glu Val Arg Lys Leu Ser Asn Gly
290                 295                 300

Arg Leu Ser Thr Ser Leu Lys Leu Gly Pro Leu Gln Pro Arg Gly Val
305                 310                 315                 320

Pro Leu Arg Glu Lys Lys Ala Thr Gln Met Val Ala Ile Val Leu Gly
            325                 330                 335

Ala Phe Ile Val Cys Trp Leu Pro Phe Phe Leu Thr His Val Leu Asn
            340                 345                 350

Thr His Cys Gln Thr Cys His Val Ser Pro Glu Leu Tyr Ser Ala Thr
            355                 360                 365

Thr Trp Leu Gly Tyr Val Asn Ser Ala Leu Asn Pro Val Ile Tyr Thr
            370                 375                 380

Thr Phe Asn Ile Glu Phe Arg Lys Ala Phe Leu Lys Ile Leu Ser Cys
385                 390                 395                 400

<210> SEQ ID NO 2
<211> LENGTH: 500
<212> TYPE: PRT
<213> ORGANISM: Homo sapiens

<400> SEQUENCE: 2

Asp Tyr Lys Asp Asp Asp Ala Met Gly Gln Pro Gly Asn Gly Ser Ala
1               5                   10                  15

Phe Leu Leu Ala Pro Asn Arg Ser His Ala Pro Asp His Asp Val Thr
            20                  25                  30

Gln Gln Arg Asp Glu Val Trp Val Val Gly Met Gly Ile Val Met Ser

```
                35                  40                  45
Leu Ile Val Leu Ala Ile Val Phe Gly Asn Val Leu Val Ile Thr Ala
 50                  55                  60
Ile Ala Lys Phe Glu Arg Leu Gln Thr Val Thr Asn Tyr Phe Ile Thr
 65                  70                  75                  80
Ser Leu Ala Cys Ala Asp Leu Val Met Gly Leu Ala Val Val Pro Phe
                 85                  90                  95
Gly Ala Ala His Ile Leu Met Lys Met Trp Thr Phe Gly Asn Phe Trp
                100                 105                 110
Cys Glu Phe Trp Thr Ser Ile Asp Val Leu Cys Val Thr Ala Ser Ile
                115                 120                 125
Glu Thr Leu Cys Val Ile Ala Val Asp Arg Tyr Phe Ala Ile Thr Ser
                130                 135                 140
Pro Phe Lys Tyr Gln Ser Leu Leu Thr Lys Asn Lys Ala Arg Val Ile
145                 150                 155                 160
Ile Leu Met Val Trp Ile Val Ser Gly Leu Thr Ser Phe Leu Pro Ile
                165                 170                 175
Gln Met His Trp Tyr Arg Ala Thr His Gln Glu Ala Ile Asn Cys Tyr
                180                 185                 190
Ala Glu Glu Thr Cys Cys Asp Phe Phe Thr Asn Gln Ala Tyr Ala Ile
                195                 200                 205
Ala Ser Ser Ile Val Ser Phe Tyr Val Pro Leu Val Ile Met Val Phe
                210                 215                 220
Val Tyr Ser Arg Val Phe Gln Glu Ala Lys Arg Gln Leu Asn Ile Phe
225                 230                 235                 240
Glu Met Leu Arg Ile Asp Glu Gly Leu Arg Leu Lys Ile Tyr Lys Asp
                245                 250                 255
Thr Glu Gly Tyr Tyr Thr Ile Gly Ile Gly His Leu Leu Thr Lys Ser
                260                 265                 270
Pro Ser Leu Asn Ala Ala Lys Ser Glu Leu Asp Lys Ala Ile Gly Arg
                275                 280                 285
Asn Thr Asn Gly Val Ile Thr Lys Asp Glu Ala Glu Lys Leu Phe Asn
290                 295                 300
Gln Asp Val Asp Ala Ala Val Arg Gly Ile Leu Arg Asn Ala Lys Leu
305                 310                 315                 320
Lys Pro Val Tyr Asp Ser Leu Asp Ala Val Arg Arg Ala Ala Leu Ile
                325                 330                 335
Asn Met Val Phe Gln Met Gly Glu Thr Gly Val Ala Gly Phe Thr Asn
                340                 345                 350
Ser Leu Arg Met Leu Gln Gln Lys Arg Trp Asp Glu Ala Ala Val Asn
                355                 360                 365
Leu Ala Lys Ser Arg Trp Tyr Asn Gln Thr Pro Asn Arg Ala Lys Arg
                370                 375                 380
Val Ile Thr Thr Phe Arg Thr Gly Thr Trp Asp Ala Tyr Lys Phe Cys
385                 390                 395                 400
Leu Lys Glu His Lys Ala Leu Lys Thr Leu Gly Ile Ile Met Gly Thr
                405                 410                 415
Phe Thr Leu Cys Trp Leu Pro Phe Phe Ile Val Asn Ile Val His Val
                420                 425                 430
Ile Gln Asp Asn Leu Ile Arg Lys Glu Val Tyr Ile Leu Leu Asn Trp
                435                 440                 445
Ile Gly Tyr Val Asn Ser Gly Phe Asn Pro Leu Ile Tyr Cys Arg Ser
                450                 455                 460
```

```
Pro Asp Phe Arg Ile Ala Phe Gln Glu Leu Leu Cys Leu Arg Arg Ser
465                 470                 475                 480

Ser Leu Lys Ala Tyr Gly Asn Gly Tyr Ser Ser Asn Gly Asn Thr Gly
                485             490                 495

Glu Gln Ser Gly
            500
```